US009457046B2

(12) United States Patent
Ferdinandy et al.

(10) Patent No.: US 9,457,046 B2
(45) Date of Patent: Oct. 4, 2016

(54) COMPOUNDS FOR THE TREATMENT OF ISCHEMIC INJURY

(71) Applicant: PHARMAHUNGARY 2000 KFT, Szeged (HU)

(72) Inventors: Péter Ferdinandy, Budapest (HU); Zoltán Varga, Gyermely (HU); Támas Csont, Szeged (HU); Anikó Görbe, Szeged (HU)

(73) Assignee: PharmalHungary 2000 Kft., Szeged (HU)

( * ) Notice: Subject to any disclaimer, the term of this patent is extended or adjusted under 35 U.S.C. 154(b) by 0 days.

(21) Appl. No.: 14/351,279

(22) PCT Filed: Oct. 17, 2012

(86) PCT No.: PCT/HU2012/000107
§ 371 (c)(1),
(2) Date: Apr. 11, 2014

(87) PCT Pub. No.: WO2013/057527
PCT Pub. Date: Apr. 25, 2013

(65) Prior Publication Data
US 2014/0256792 A1 Sep. 11, 2014

(30) Foreign Application Priority Data
Oct. 17, 2011 (EP) .................................. 11462021

(51) Int. Cl.
A61K 48/00 (2006.01)
C07H 21/02 (2006.01)
A61K 31/713 (2006.01)
C12N 15/113 (2010.01)

(52) U.S. Cl.
CPC ........... *A61K 31/713* (2013.01); *C12N 15/113* (2013.01); *C12N 2310/113* (2013.01); *C12N 2310/141* (2013.01)

(58) Field of Classification Search
None
See application file for complete search history.

(56) References Cited

U.S. PATENT DOCUMENTS

| 2009/0005336 | A1 | 1/2009 | Wang | |
| 2009/0281167 | A1* | 11/2009 | Shen et al. | 514/44 A |
| 2010/0010073 | A1 | 1/2010 | Thum et al. | |
| 2010/0173288 | A1* | 7/2010 | Zhang et al. | 435/6 |
| 2010/0202973 | A1* | 8/2010 | Pivarcsi et al. | 424/9.2 |
| 2010/0317713 | A1 | 12/2010 | Olson et al. | |

FOREIGN PATENT DOCUMENTS

| CA | 2609142 A1 | 1/2007 |
| CN | 101643791 A | 2/2010 |
| EP | 2275545 A1 | 1/2011 |
| WO | 2006137941 A2 | 12/2006 |
| WO | 2009062169 A2 | 5/2009 |
| WO | 2009132351 A2 | 10/2009 |
| WO | 2010091204 A1 | 8/2010 |
| WO | 2010103015 A1 | 9/2010 |
| WO | 2010120969 A1 | 10/2010 |
| WO | 2010129672 A1 | 11/2010 |
| WO | 2010135570 A1 | 11/2010 |
| WO | 2011084460 A1 | 7/2011 |
| WO | WO 2012020307 | * 2/2012 |

OTHER PUBLICATIONS miRBase entry for miR-478b downloaded from http://www.mirbase.org/cgi-bin/mirna_entry.pl?acc=MI0003530 on Apr. 24, 2015.*
miRBase entry for miR-139-5p doownloaded from http://www.mirbase.org/cgi-bin/mirna_entry.pl?acc=MI0000261 on Jul. 27, 2015.*
Bostjancic E et al. MicroRNA microarray expression profiling in human myocardial infarction Dis Markers. 2009 255-268 27.
Cheng Y et al. Ischaemic preconditioning-regulated miR-21 protects heart against ischaemia/reperfusion injury via anti-apoptosis through its target PDCD4, Cardiovascular Research 2010 431-439 87.
Csonka C et al. Effect of postconditioning on the gene expression pattern of rat hearts: a DNA microarray study. Journal of Molecular and Cellular Cardiology Abstracts 2008 817 44.
Dong S et al. MiRNA expression signature and the role of miRNA-21 in the early phase of acute myocardial infarction J Biol Chem 2009 29514-29525 284.
Fasanaro P. et al. miRNA: Emerging therapeutic targets in acute ischemic diseases. Pharmacology and Therapeutics 2010 92-104 125.
Ferdinandy P et al. Interaction of cardiovascular risk factors with myocardial ischemia-reperfusion injury, preconditioning, and postconditioning Pharmacol Rev. 2007 418-458 59.
Frost RJ and Van Rooij E. miRNAs as therapeutic targets in ischemic heart disease J Cardiovasc Transl Res. 2010 280-289 3.
Godwin JG et al. Identification of a microRNA signature of renal ischemia reperfusion injury. Proc Natl Acad Sci U S A. 2010 14339-14344 107(32).
He B et al. Role of miR-1 and miR-133a in myocardial ischemic postconditioning. Journal of Biomedical Science 2011 1-10 18(22).
Lusardi TA et al. Ischemic preconditioning regulates expression of microRNAs and a predicted target, MeCP2, in mouse cortex, Journal of Cerebral Blood Flow & Metabolism 2010 744-756 30.
Meder B et al. MicroRNA signatures in total peripheral blood as novel biomarkers for acute myocardial infarction. Basic Res Cardiol. 2011 13-23 106(1).

(Continued)

Primary Examiner — Richard Schnizer
(74) Attorney, Agent, or Firm — Jason D. Voight

(57) ABSTRACT

The present invention relates to microRNA (miRNA) compounds for use in the treatment of consequences of acute ischemia/reperfusion, a method for preparing miRNA compounds by using test ischemic-reperfusion, test preconditioning and test postconditioning of biological samples, use of the miRNA compounds in the preparation of pharmaceutical compositions having cytoprotective and/or anti-ischemic effect in ischemic cardiac diseases.

10 Claims, 16 Drawing Sheets

(56) References Cited

OTHER PUBLICATIONS

Obad S et al. Silencing of microRNA families by seed-targeting tiny LNAs. Nature Genetics 2011 371-378 43.

Onody A. et al. Effect of classic preconditioning on the gene expression pattern of rat hearts: a DNA microarray study. FEBS Letters 2003 35-40 536.

Ren XP et al. MicroRNA-320 is involved in the regulation of cardiac ischemia/reperfusion injury by targeting heat-shock protein 20 Circulation. 2009 2357-2366 119.

Rooij E Van et al. Control of stress-dependent cardiac growth and gene expression by a miRNA Science 2007 575-579 316.

Sepramaniam S. et al. MicroRNA 320a Functions as a Novel Endogenous Modulator of Aquaporins 1 and 4 as Well as a Potential Therapeutic Target in Cerebral Ischemia. The Journal of Biological Chemistry 2010 29223-29230 285(38).

Small EM et al. MicroRNAs add a new dimension to cardiovascular disease. Circulation 2010 1022-1032 121.

Wang X et al. MiRNA-494 targeting both proapoptotic and antiapoptotic proteins protects against ischemia/reperfusion-induced cardiac injury Circulation. 2010 1308-1318 122.

Xu Cheng-Fu et al. Regulation of Hepatic MicroRNA Expression in Response to Ischemic Preconditioning following Ischemia/Reperfusion Injury in Mice. Journal of Integrative Biology 2009 513-520 13(6).

Yin KJ et al. miR-497 regulates neuronal death in mouse brain after transient focal cerebral ischemia. Neurobiol Dis. 2010 17-26 38(1).

* cited by examiner

Panel A

Panel B

Panel C

Panel A

Panel B

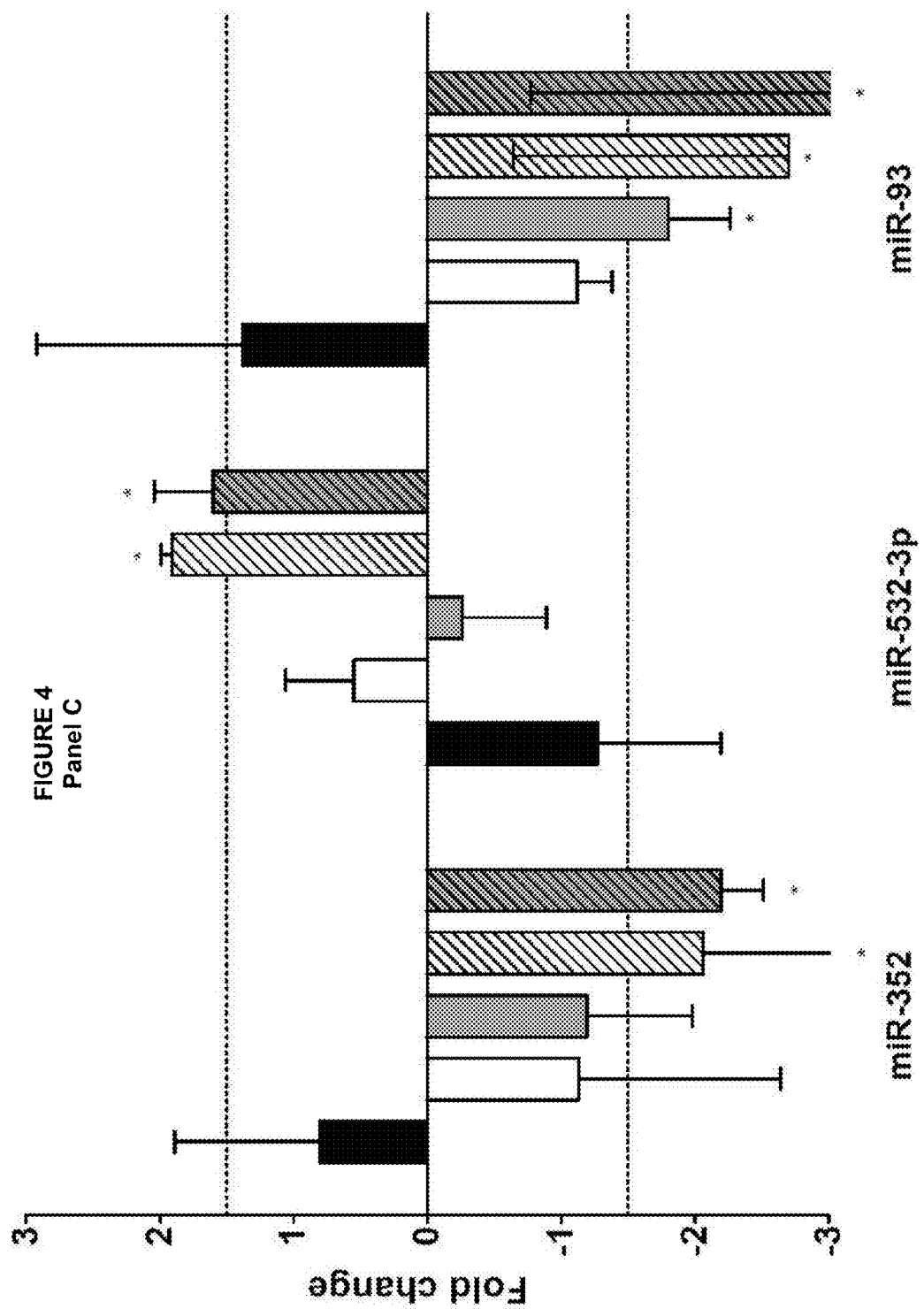

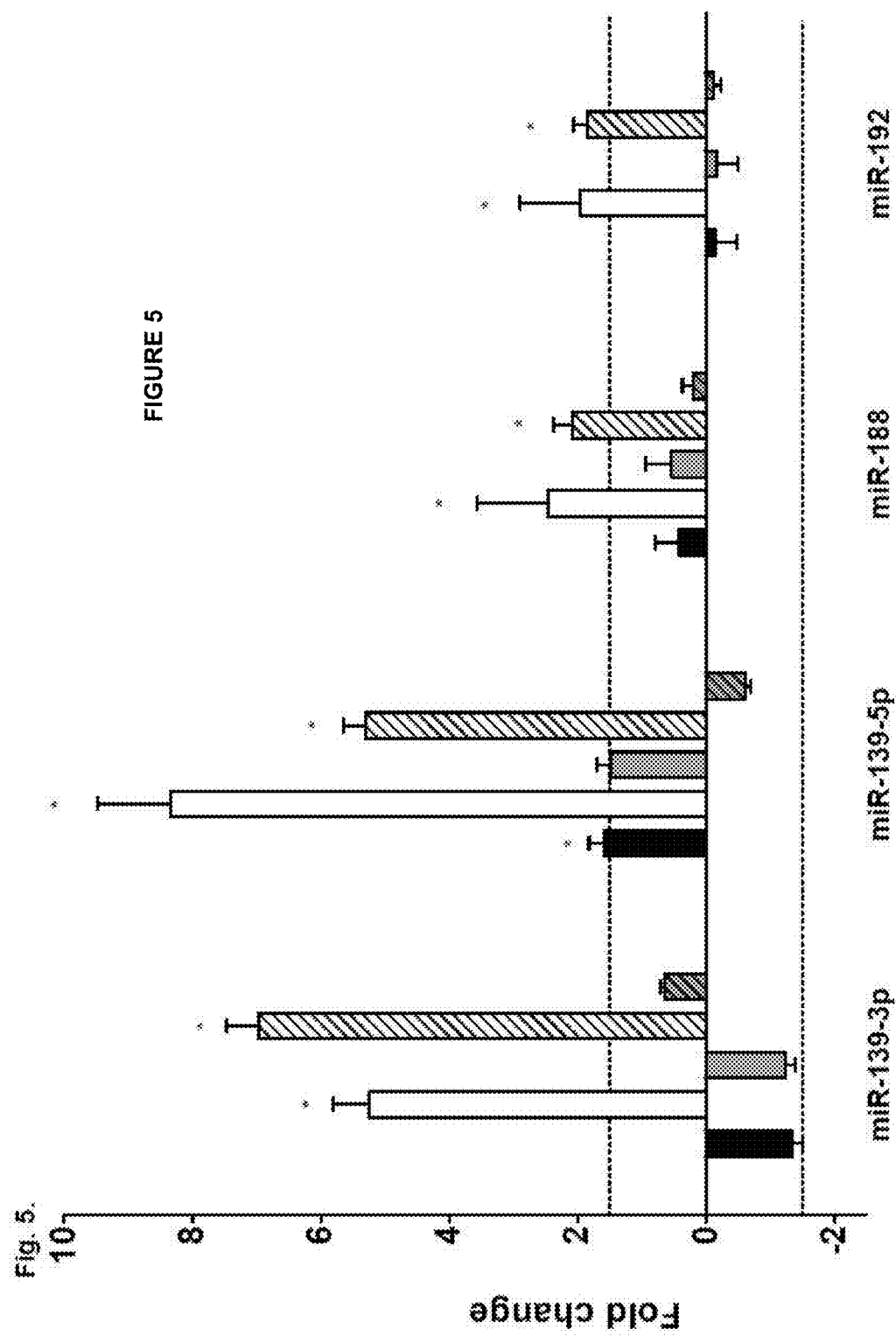

Panel A

Panel B

Panel A

Panel B

Panel A

Panel B

COMPOUNDS FOR THE TREATMENT OF ISCHEMIC INJURY

This is the national stage of International Application PCT/HU2012/000107, filed Oct. 17, 2012.

FIELD OF THE INVENTION

The present invention relates to a method for preparing specific microRNA (miRNA) compounds by using test ischemia-reperfusion, test preconditioning and test postconditioning of biological samples, the microRNA compounds and pharmaceutical composition comprising them for use in a prophylaxis and/or treatment of cells or tissues to protect them against consequences of acute ischemia-reperfusion injury in a patient predisposed to or attacked by ischemic, use of the miRNA compounds and nucleic acid encoding them in diagnosis and in the preparation of pharmaceutical compositions and methods for treatment of a patient in need of protecting cells or tissues against consequences of acute ischemia-reperfusion injury.

BACKGROUND ART

MicroRNAs

MicroRNAs (miRNAs) are small (about 18 to about 25 nucleotides in length, preferably 19-23 nucleotides in length) non-protein coding RNA molecules that are currently being recognized as endogenous physiological regulators of gene expression [Bartel D P 2004]. Recently it has been well established that miRNAs play an essential role in the posttranscriptional regulation of gene expression by repression or activation of translation/transcription ("RNA interference") [Lim L P et al. 2005; Buchan J R et al. 2007]. While the total number of different human miRNAs is estimated to be up to 1000, representing by large 1-2% of the whole genome, approximately 300-500 have been studied to date [Small E M et al. 2010]. Whereas in many cases the target genes and consequently the associated biological functions have not been identified, it is estimated that miRNAs regulate up to 30% of the genes of the whole genome. The large number of miRNAs and the even higher number of target genes suggest an important role of miRNAs in the onset and progression of a wide range of diseases. MiRNA activity can be antagonized in various ways, e.g. by anti-sense miRNAs, termed antagomirs or miRNA inhibitors, thus a disease-related up-regulation of a particular miRNA can be normalized, as a treatment, via the administration of the miRNA inhibitors in vitro and in vivo in terms of their expression. Effect of miRNAs can be achieved with compounds which are miRNA agonists, e.g. miRNA mimics, thus in case of a disease-related down-regulation of a particular miRNA can be normalized in vitro and in vivo via exogenously administered miRNA agonist, e.g. miRNA mimics. Besides this, medicaments can be developed which normalize the expression of a disease-related miRNA.

MiRNAs are known to play important roles in many physiological and pathological processes at the cellular level in several organs and/or tissues. For example, in the heart, these include ischemia-reperfusion injury, cardiac fibrosis, hypertrophic response, myocyte contractility, cardiac development, and arrhythmogenesis [van Rooij E et al. 2007]. Recently, several groups reported the involvement of miR-NAs in the pathophysiology of myocardial infarction [Ren X P et al. 2009; Dong S et al. 2009]. The importance of miRNAs in cardiac pathologies suggests their promising therapeutic and/or diagnostic potential [Frost R J et al., 2010; Fasanaro P et al. 2010]. However, the role of miRNAs in the ischemic myocardium, particularly in the early phase of myocardial ischemia-reperfusion injury and in endogenous cardioprotective maneuvers such as ischemic pre- and postconditioning is not known.

Ischemic Heart Disease and Cardioprotection

Ischemic heart disease is the leading cause of death in the industrialized world. Ischemic heart disease includes acute myocardial infarction (MI) in which death of myocardial tissue thereby acute heart failure and arrthythmias occur, as well as chronic myocardial infarction causing cardiac tissue remodeling and heart failure. MI occurs when a coronary artery becomes occluded and can no longer supply blood to the myocardial tissue. This is most commonly due to occlusion (blockage) of a coronary artery following the rupture of a vulnerable atherosclerotic plaque, which is an unstable collection of lipids (fatty acids) and white blood cells (especially macrophages) in the wall of an artery. Occlusion of coronary artery can occur by other mechanisms as well, e.g. by mechanical occlusion of the artery e.g. during cardiac surgery, or by sudden constriction of arteries e.g. due to pathological increase of sympathetic tone.

When an acute myocardial infarction occurs, the tissue that is no longer receiving adequate blood flow and dies within a few hours. Within seconds after the coronary occlusion of a myocardial infarction, the under-perfused myocardial cells no longer contract, leading to abnormal wall motion, high wall stresses within and surrounding the infarct, depressed ventricular function, and occurrence of arrhythmias. Within weeks after the cell death in the affected myocardial tissue, myocardial cells are replaced with scar tissue. Therefore, we can clearly distinguish between acute myocardial infarction (characterized by rapid cell death) and chronic infarction (characterized by development of scar tissue, and remodeling of the myocardial tissue).

There are warning signs and symptoms, which usually precede an acute myocardial infarction. The pain associated with an acute myocardial infarction can feel like a bad heartburn. Patients having acute infarction may feel a pressure or crushing pain in the chest, sometimes with sweating, dizziness, nausea or vomiting. They may also experience pain that extends from the chest into the jaw, left arm or left shoulder. Feeling tightness in the chest, having shortness of breath for more than a couple of seconds or having a sudden overwhelming fatigue episode is very common a warning sign.

The treatment of acute myocardial infarction has entered a new era where mortality can be approximately halved by procedures which allow the rapid return of blood flow to the ischemic zone of the myocardium, i.e. reperfusion therapy. Reperfusion, however, may lead to further complications such as diminished cardiac contractile function (stunning) and arrhythmias. Moreover, there is experimental evidence that irreversible cell injury leading to cell necrosis and apoptosis may be enhanced by reperfusion. Therefore, development of anti-ischemic agents to delay the onset of necrosis and limit the total extent of infarction during ischemia-reperfusion thereby improving myocardial function and decrease the incidence of arrhythmias are of great clinical importance, [see for a review: Ferdinandy P et al. 2007]

Earlier pharmacological approaches to attenuate the consequences of ischemia-reperfusion injury have been of limited experimental efficacy or have failed to translate into useful clinical treatments. However, more recently the heart has been shown to possess a remarkable ability to adapt to ischemia-reperfusion stress and this molecular plasticity of the heart in ischemia-reperfusion has been the focus of intense research in the hope that the underlying mechanisms may be amenable to therapeutic exploitation.

Recently, several studies have suggested that miRNAs contribute to ischemia-reperfusion injury by altering key signaling elements, thus making them potential therapeutic targets. Studies using various in vivo, ex vivo, and in vitro models have suggested the possible involvement of miR-1, miR-21, miR-29, miR-92a, miR-133, miR-199a, and miR-320 in ischemia-reperfusion injury and/or remodeling after myocardial infarction [see for example, Ye Y. et al. 2011, Ren X P et al. 2009]. Sepramaniam S. et al. (2010) have shown that antimiR-320a could bring about a reduction of infarct volume incerebral ischemic with a concomitant increase in aquaporins 1 and 4 mRNA and protein expression which is divergent from the results of Ren X P et al (2009) and indicated that miRNA regulation in the brain is different from that in the heart. The involvement of muscle and/or cardiac-specific miRNAs miR-1, miR-133a/b and miR-208 in remodeling after human MI, as compared to their regulation in fetal hearts, have been shown [Bostjancic E. et al. 2010, He B, et al. (2011)]

Godwin J G, et al. (2010) provided a miRNA signature of renal ischemia-reperfusion injury in a kidney ischemia-reperfusion model. They found a significant down-regulation of miR-192. MiRNA signatures in total peripheral blood as novel biomarkers for acute myocardial infarction have also been identified and a significantly elevation of plasma miR-30c level reported [Meder B et al. 2010].

Dong S et al (2009) studied the role of miRNA-21 and suggested that it shows a protective effect against ischemic-induced cardiac myocyte damage. However, the authors applied a permanent occlusion of the coronary artery with no reperfusion and pre- and postconditioning was not studied. Cheng Y (2010) also suggested that ischaemic preconditioning-regulated miR-21 protects the heart against ischaemia/reperfusion injury. Both authors examined the miRNA expression only after 6 hours of the start of ischemic state, at which time-point infarction is fully developed in the rat heart. The present inventors came to a different result based on a specific study in pre- and postconditioning and a narrower, clinically more important time-window for obtaining sample.

Yin K J et al. (2010) have found a significant up-regulation of miR-497 after cerebral ischemic and suggest that this miRNA promotes ischemic neuronal death by negatively regulating anti-apoptotic proteins, bcl-2 and bcl-w and that this pathway may contribute to the pathogenesis of the ischemic brain injury in stroke.

Xu, Ch et al (2009) have suggested a potential role of mmu-miR-23a, mmu-miR-326, mmu-miR-346_MM1 and mmu-miR-370 in the protective mechanism of IPC against hepatic I/R injury in liver. However, expression pattern of miRNAs in the liver appears to be significantly different from that in the heart. In this study infarct size was not measured.

Lusardi T A et al., (2010) suggest that ischemic preconditioning regulates expression of miRNAs and their predicted targets in mouse brain cortex. No indication on treatment of acute myocardial infarction is implied.

He B, et al. (2011) studied expression of miRNAs in hearts exposed to ischemia/reperfusion and found that arbitrarily selected miRNA-1 and miRNA-133 are up-regulated in post-conditioning. The authors tried to find the target of these miRNAs. No proposal for treatment with these or other miRNAs is made.

A number of miRNA has been mentioned in the art as having effect in heart diseases or ischemic conditions. For example, in US2010/0010073 [Thum T., Bauersachs J. 2010] a large number of miRNA sequences are proposed as potential active substances in the prophylaxis or treatment of heart diseases, among others miR-134, miR-212, miR-214, miR-21, miR-129, miR-182, and miR-290.

Wang X. et al. (2010) have found that MiRNA-494 targeting both proapoptotic and antiapoptotic proteins protects against ischemic-reperfusion-induced cardiac injury.

In WO2009/062169 (2009) and in US2010/0317713 (2010) Olson E. and Van Rooij, E. suggest that inhibition of miR-15 family (miR-15a, mir-15b, miR-16, miR-195, miR-424 and miR-497) should be useful in the treatment of cardiac hypertrophy, heart failure or myocardial infarction and for the diagnosis of these conditions. Experimental data relate mainly to the morphological study of the heart and no conclusion for the cytoprotective effect of these molecules in acute ischemia-reperfusion injury can be drawn.

WO2010/103015 [Engelhardt S. and Jentzsch C. (2010)] reports on an experiment in cardiomyocytes were transfected with a library of 471 human precursor miRNAs and their effect on cardiomyocyte cell size and morphology was studied. While an indirect hint as to the effect of these miRNA on cardiomyocytes may be made, no clear conclusion as to their cardioprotective effect can be drawn.

In WO2010/135570 [Olson E. and Van Rooij, E. 2010] in an effort to identify miRNAs involved in post-myocardial infarction (MI), MI was experimentally induced in mouse hearts and miRNA expression profiles were compared in mouse hearts 3 and 14 days after MI. No indication of miRNA regulation shortly after MI or an acute ischemia-reperfusion is disclosed.

In WO 2010/091204 [Olson E. and Van Rooij, E. 2010] co-administration of an inhibitor of miR-208a or miR-208b and an inhibitor of miR-499 is proposed for the treatment of cardiac hypertrophy, heart failure or MI, as it was found that knockdown of these miRNAs inhibit cardiac stress response. No direct evidence is provided.

In EP2275545A1 [Thum T. and Fiedler, J. 2011] miR-24 up-regulation was detected in endothelial cells 14 days after myocardial infarction, whereas miR-24 levels were unchanged in cardiomyocytes post-myocardial infarction (FIG. 1d). Next, cardiac endothelial cells were targeted by antagomirs and miR-24 expression repressed. In mice, immediate treatment after myocardial infarction with an antagomir against miR-24 resulted in improved cardiac function and attenuation of left ventricular dilatation.

In WO2010/120969 [Olson E. et al. 2010] it is disclosed that miR-30 family member are down-regulated in cardiac tissue 3 and 14 days following myocardial infarction. No data on the miR30 family regulation immediately or soon after MI are provided.

In CN101643791A [Wang N. et al. 2010] use of an antisense nucleotide of miRNA-328 is proposed in diagnosing, preventing and treating heart disease, including myocardial infarction.

In WO2011/084460 [Olson Eric N.; Rooij Eva Van; Quiat Daniel 2011] up and down-regulation of miRNAs 6, 24 and 48 hours after myocardial infarction and/or after reperfusion is studied. It has been found that a number of the miRNAs are up-regulated and a number of miRNAs are downregulated after MI, whereas the level of regulation is different in various points of time. The authors provide a suggestion as to which miRNAs should be antagonized (miR-15 family, miR-30 family, miR-92a, miR-320, miR-20, miR-199a, miR-499a) or whether an agonist thereof should be administered (miR-126, miR-143, miR-210 and miR-29a-c) under the conditions studied. No data on miRNA regulation in pre- or post-conditioning are reported, however, and there are no information on during or immediately after ischemia-reperfusion.

These publications consider typically the late upregulation of miRNAs after infarction, usually days after the ischemic attack or experimental simulation thereof, and are not related to cytoprotective effect of miRNA in acute ischemia-reperfusion injury and the authors did not examine the potential role of miRNA in cardioprotection. Moreover, in case of a large number of miRNAs the present inventors have found a different regulation of the miRNA species in an experimental setting wherein specific cytoprotective effect has been studied in pre- and post-conditioning protocols.

In the prior art, experiments wherein the miRNAs or agonists or antagonist thereof assayed are disclosed only in a very few cases; most often, merely observation on regulation of said miRNAs in disease conditions or in an experimental model thereof are described.

The art appears to be silent about a method for obtaining miRNAs and related compounds (miRNA compounds, e.g. miRNA mimics and/or miRNA inhibitors) specifically involved in cytoprotection in ischemia-reperfusion of a tissue or an organ and in particular in acute ischemia and/or reperfusion. The present inventors found that cytoprotective miRNA compounds can be obtained provided that regulation of miRNA species in preconditioning and/or postconditioning is considered. Said compounds are particularly useful in cytoprotection during, before or after acute ischemia and/or reperfusion injury.

BRIEF DESCRIPTION OF THE INVENTION

The invention relates to a method for obtaining a microRNA (miRNA) compound for use in a treatment to protect cells or tissues against consequences of acute ischemic injury and/or acute reperfusion injury in the heart of a patient predisposed to or attacked by ischemia, i) providing a set of biological samples comprising expressed miRNA species, said set of samples comprising
  a control sample,
  a first sample and
  a second sample and/or
  a third sample
  wherein the samples can be subjected to ischemia, ii) exposing each of the samples to aerobic perfusion for a time-period, and within this time period
  the control sample is exposed neither to ischemia nor to preconditioning nor to postconditioning, thereby obtaining a non-ischemic control sample, and
  exposing the first sample to ischemia thereby obtaining an ischemic sample, and
  preconditioning the second sample by exposing it to a preconditioning protocol and then to ischemia thereby obtaining a preconditioned sample, and/or
  postconditioning the third sample by exposing it to ischemia and to a postconditioning protocol thereby obtaining a postconditioned sample, iii) assessing the expression level of miRNA species
  in the non-ischemic control sample
  in the ischemic sample as compared to the non-ischemic control sample and
    in the preconditioned sample as compared to the non-ischemic control sample and/or
    in the postconditioned sample as compared to the non-ischemic control sample, and iv) calculating the ratio of the expression levels of said miRNA species
  in the preconditioned sample as compared to the ischemic sample and/or
  in the postconditioned sample as compared to the ischemic sample, v) identifying an miRNA species the expression level of which is up-regulated by at least 1.3 fold, preferably by at least 1.5 fold, or by at least 1.8 fold or by at least 2.0 fold, or down-regulated by at least 1.3 fold, preferably 1.5 fold or by at least 1.8 fold or by at least 2.0 fold in the preconditioned sample and/or in the postconditioned sample relative to the ischemic/reperfused sample, vi) obtaining the nucleotide sequence of said miRNA species, vii) synthesizing an miRNA compound,
  said miRNA compound being a miRNA agonist of said miRNA species, termed a pre-ischemic cytoprotective miRNA species, provided that the miRNA species is up-regulated in the preconditioned sample relative to the ischemic sample and/or
  said miRNA compound being a miRNA agonist of said miRNA species, termed a post-ischemic cytoprotective miRNA species, provided that the miRNA species is up-regulated in the postconditioned sample relative to the ischemic sample
  and/or
  the miRNA compound being a miRNA antagonist of the miRNA species, termed a pre-ischemic cytopathic miRNA species, provided that the miRNA species is down-regulated in the preconditioned sample relative to the ischemic sample and/or
  the miRNA compound being a miRNA antagonist of the miRNA species, termed a post-ischemic cytopathic miRNA species, provided that the miRNA species is down-regulated in the postconditioned sample relative to the ischemic sample.

In the present invention preferably the samples are collected for expression level assessment after at most 1 h, 1.5 h, 2 h, 2.5 h or 3 h after the end of ischemia. Preferably, reperfusion is carried out for at most 1 h, 1.5 h, 2 h, 2.5 h or 3 h after the end of ischemia. Preferably, reperfusion is carried out for at least 0.5 h or 1 h or 1.5 h after the end of ischemia.

In a preferred embodiment ischemia includes ischemia and reperfusion.

In a further preferred embodiment ischemia can be considered as hypoxia. In a preferred embodiment hypoxia includes hypoxia and reoxygenation.

A significant up or down-regulation of a miRNA species is termed herein as an alteration or change of the level of miRNA species by at least 1.3 fold or preferably by at least 1.5 fold or by at least 1.8 fold or by at least 2.0 fold or possibly higher at an acceptable p value, preferably at a p value of not larger than 0.05 (or at p<0.05) at statistical significance testing. It is to be understood that the question of significance may depend on the measurement method as well as measurement accuracy or correctness. Therefore, what is important that the level of up or down-regulation be significant under the conditions used whereas the level given in numbers may vary, as clearly understood by a person skilled in the art. Preferably, in any embodiment of the invention the expression level of the miRNA species is
  up-regulated by at least 1.5 fold, highly preferably by at least 1.8 fold, or by at least 2 fold and/or
  down-regulated by at least 1.5 fold, highly preferably by at least 1.8 fold, or by ate least 2 fold.

In a preferred embodiment the down-regulation is assessed by log scale, preferably by a log 2 scale or assessed by a linear scale.

In an embodiment of the invention acute myocardial infarction is treated or prevented.

In a preferred embodiment said miRNA compound is selected from a group consisting of miRNA agonists of any of the following miRNA species: miR-333, miR-188, miR-125b*, miR-139-3p, miR-320, miR-532-3p, miR-451, miR-212, miR-192, miR-139-5p, miR-503, miR-33, miR-328, miR-181a, miR-7b, let7e, let7i, miR-1 and miRNA antagonists of any of the following miRNA species: miR-487b, miR-208, miR-19b, miR-19a, miR-352, miR-93, miR-494, miR-106b, and any combination thereof.

In a more preferred embodiment said miRNA compound is selected from a group consisting of miRNA agonists of any of the following miRNA species: miR-125b*, miR-139-3p, miR-532-3p, miR-212, miR-139-5p, miR-33, miR-let7b and miRNA antagonists of any of the following miRNA species: miR-494, miR-487b, and any combination thereof.

In a preferred embodiment the miRNA species identified is a pre-ischemic cytoprotective miRNA species, wherein the pre-ischemic cytoprotective miRNA species is selected from the group consisting of miR-320, miR-139-3p, miR-139-5p, miR-188, miR-192, miR-532-3p, miR-125b*, mir-451, miR-212 a precursor thereof, a miRNA species having a seed region identical therewith, and a miRNA species which is a family member thereof wherein the miRNA compound is for use in a treatment to protect cells or tissues against consequences of ischemic injury and/or reperfusion injury in a patient predisposed to ischemia.

In a preferred embodiment, the pre-ischemic cytoprotective miRNA species is up-regulated significantly in the preconditioned sample as compared to the non-ischemic control sample, and/or said miRNA species are down-regulated significantly in the ischemic sample as compared to the non-ischemic control sample.

So as to provide an explanation, a pre-ischemic cytoprotective miRNA species which is significantly up-regulated in the preconditioned sample as compared to the non-ischemic control sample, potentially has a role in the adaptation of the tissues to ischemia and/or to reperfusion. In a preferred embodiment the miRNA species identified is a post-ischemic cytoprotective miRNA species, wherein said post-ischemic cytoprotective miRNA species is selected from the group consisting of miR-125b* miR-33, miR-139-3p miR-320, miR-532-3p, miR-188, miR-let7e, miR-let7i, miR-1, miR-503, miR-335, miR-328, miR-181a and miR-let7b a precursor thereof, a miRNA species having a seed region identical therewith, and a miRNA species which is a family member thereof wherein the miRNA compound is for use in a treatment to protect cells or tissues against consequences of acute ischemic injury in a patient attacked by ischemia.

In a preferred embodiment, the post-ischemic cytoprotective miRNA species is up-regulated significantly in the postconditioned sample as compared to the non-ischemic control sample, and/or said miRNA species being down-regulated significantly in the ischemic sample as compared to the non-ischemic control sample.

So as to provide an explanation, a post-ischemic cytoprotective miRNA species which is also significantly up-regulated in the postconditioned sample as compared to the non-ischemic control sample, probably has a role in the adaptation of the tissues to ischemia and/or to reperfusion.

If the level of a pre-ischemic or a post-ischemic cytoprotective miRNA species is not changed significantly in the ischemic sample as compared to the non-ischemic control it suggests that said miRNA does not take part in the ischemic injury.

If a pre-ischemic or a post-ischemic cytoprotective miRNA species is significantly down-regulated in the ischemic sample, i.e. an opposite regulation is observed in ischemia and in pre-conditioning or post-conditioning, respectively, it is suggested that said miRNA has a particularly strong protective effect.

In a preferred embodiment the miRNA species identified is a pre-ischemic cytopathic miRNA species, wherein the pre-ischemic cytopathic miRNA species is selected from the group consisting of mir-487b, miR-494, miR-352, miR-93, and miR-106b, a precursor thereof, a miRNA species having a seed region identical therewith, and a miRNA species which is a family member thereof, wherein the miRNA compound is for use in a treatment to protect cells or tissues against consequences of ischemic injury and/or reperfusion injury in a patient predisposed to ischemia.

In a preferred embodiment the pre-ischemic cytopathic miRNA species is down-regulated significantly in the pre-conditioned sample as compared to the non-ischemic control sample.

The pre-ischemic cytopathic miRNA species, down-regulated in the preconditioned sample relative to the ischemic sample, is termed a pre-ischemic cytotoxic miRNA species provided that said miRNA species is also up-regulated by at least 1.3 fold, preferably by at least 1.5 fold in the ischemic sample relative to non-ischemic control sample.

In a preferred embodiment the miRNA species identified is a post-ischemic cytopathic miRNA species, wherein the post-ischemic cytopathic miRNA species is selected from the group consisting of miR-208, miR-19b, miR-19a, miR-130a, miR-16, miR-21, miR-22*, miR-26b, miR-30b-5p, miR-30c, miR-30c-1*, miR-30e, miR-339-3p, miR-450a, miR-499, miR-760-5p, miR-99a, miR-99a* a precursor thereof, a miRNA species having a seed region identical therewith, and a miRNA species which is a family member thereof, wherein the miRNA compound is for use in a treatment to protect cells or tissues against consequences of ischemic injury and/or reperfusion injury in a patient attacked by ischemia.

In a preferred embodiment the post-ischemic cytopathic miRNA species is down-regulated significantly in the post-conditioned sample as compared to the ischemic sample.

The post-ischemic cytopathic miRNA species, down-regulated in the postconditioned sample relative to the ischemic sample, is termed a post-ischemic cytotoxic miRNA species provided that said miRNA species is also up-regulated by at least 1.3, preferably by at least 1.5 fold in the ischemic sample relative to non-ischemic control sample.

The invention also relates to a miRNA compound for use in a treatment to protect cells, tissues and/or organs against consequences of ischemic injury and/or reperfusion injury in a patient predisposed to or affected by ischemia, wherein said miRNA compound is selected from i) a miRNA compound obtainable by a method of the invention as disclosed herein, ii) a miRNA agonist of a pre-ischemic cytoprotective miRNA species up-regulated by at least 1.5 fold or at least 1.8 fold or at least 2 fold in a mammalian cell or tissue during preconditioning of said cell or tissue, and/or of a post-ischemic cytoprotective miRNA species up-regulated by at least 1.5 fold or at least 1.8 fold or at least 2 fold in a mammalian cell or tissue during postconditioning of said cell or tissue, iii) a miRNA antagonist of a pre-ischemic cytopathic miRNA species down-regulated by at least 1.5 fold or at least 1.8 fold or at least 2 fold in mammalian cell or tissue due to preconditioning of said cell or tissue, and/or of a post-ischemic cytopathic miRNA species down-regulated by at least 1.5 fold or at least 1.8 fold or at least 2 fold in mammalian cell or tissue due to postconditioning of said cell or tissue.

The invention also relates to a miRNA compound for use in a treatment to protect cells, tissues and/or organs against short term and/or direct consequences of acute ischemic and reperfusion injury in a patient predisposed to or affected by ischemia, in the heart of said patient, wherein said miRNA compound is for administration to the patient within 5, 4, 3, 2 or 1.5 hours after the ischemic attack or simultaneously with reperfusion and/or less than one day or less than 12, 8, 6, 5, 4, 3, 2 or 1 hour(s) before surgery or intervention associated with a risk of ischemia, wherein said miRNA compound is selected from ii) a miRNA agonist of a miRNA species, which is up-regulated by at least 1.5 fold, preferably 1.8 fold or 2 fold in a mammalian heart tissue sample during preconditioning of said cell or tissue exposed to ischemia and reperfusion, in comparison with a control heart tissue sample exposed to ischemia and reperfusion, and which is a pre-ischemic cytoprotective miRNA species and/or of a miRNA species, which is up-regulated by at least 1.5 fold, preferably 1.8 fold or 2 fold in a mammalian heart tissue sample during postconditioning of said cell or tissue exposed to ischemia and reperfusion, in comparison with a control heart tissue sample exposed to ischemia and reperfusion and which is a post-ischemic cytoprotective mirRNA species, iii) a miRNA antagonist of a miRNA species, which is down-regulated by at least 1.5 fold, preferably 1.8 fold or 2 fold in mammalian heart tissue sample due to preconditioning of said cell or tissue exposed to ischemia and reperfusion, in comparison with a control heart tissue sample exposed to ischemia and reperfusion and which is a pre-ischemic cytopathic mirRNA species, and/or of miRNA species, which is down-regulated by at least 1.5 fold, preferably 1.8 fold or 2 fold in mammalian heart tissue sample due to postconditioning of said cell or tissue exposed to ischemia and reperfusion, in comparison with a control heart tissue sample exposed to ischemia and reperfusion and which is a post-ischemic cytopathic miRNA species, wherein the miRNA agonist or antagonist is a nucleic acid moiety comprising a nucleotide sequence identical with or complementer to the seed region of the corresponding miRNA species and/or which comprises a 17 to 27 nucleotides long nucleic acid segment the sequence of which is identical to the sequence of a mature miRNA species or to a complementer thereof, or is different at most in 1, 2, 3, 4, 5 or 6 nucleotide(s) therefrom or from said complementer, respectively.

Preferably, the miRNA agonist is the agonist of a miRNA species which is simultaneously a pre-ischemic cytoprotective miRNA species and a post-ischemic cytoprotective miRNA species, wherein preferably the miRNA species is selected from the group of miR-188, miR-125b*, miR-139-3p, miR-320 and miR-532-3p.

Preferably, the miRNA antagonist is the antagonist of a miRNA species which is simultaneously a pre-ischemic cytopathic miRNA species and a post-ischemic cytopathic miRNA species, wherein preferably the miRNA species is selected from the group of miR-352, miR-93 and miR-487b.

An agonist and/or antagonist miRNA compound of a miRNA species, which is pre-ischemic cytopathic and simultaneously a post-ischemic cytoprotective miRNA species (e.g. miR-335) or pre-ischemic cytoprotective and simultaneously a post-ischemic cytopathic is not preferred according to the present invention. Thus, these miRNA species are regulated differently in pre- and postconditioned samples in a method described herein.

Preferably, said miRNA compound is a miRNA agonist of a miRNA species selected from the group of miR-333, miR-188, miR-125b*, miR-139-3p, miR-320, miR-532-3p, miR-451, miR-212, miR-192, miR-139-5p, miR-503, miR-33, miR-328, miR-181a, miR-7b, let7e, let7i, miR-1 and any combination thereof and/or a miRNA antagonist of a miRNA species selected from the group of miR-487b, miR-208, miR-19b, miR-19a, miR-352, miR-93, miR-494, miR-106b or any combination thereof.

More preferably, said miRNA compound is a miRNA agonists of a miRNA species selected from the group of miR-125b*, miR-139-3p, miR-532-3p, miR-212, miR-139-5p, miR-33, miR-let7b and/or a miRNA antagonists of a miRNA species selected from the group of miR-494, miR-487b and any combination thereof.

More preferably, said miRNA compound is selected in itself or as a combination from the group consisting of an agonist of miRNA species miR-139-5p, miR-33, miR-125b*, let-7b, an antagonist of miRNA species miR-494 and miR-487b, and miRNA agonists or antagonists comprising a nucleotide sequence identical with or complementer to the seed region of said miRNA species and/or which comprises a 17 to 27 nucleotides long nucleic acid segment the sequence of which is identical to the sequence of said miRNA species or to a complementer thereof, or is different at most in 1, 2, 3, 4, 5 or 6 nucleotide(s) therefrom or from said complementer, wherein said miRNA compound shows a cell protective effect in a cardiomyocyte cell viability assay.

Preferably, said pre-ischemic cytoprotective miRNA species is selected from the group consisting of miR-320, miR-139-3p, miR-139-5p, miR-188, miR-192, miR-532-3p, miR-125b*, mir-451, miR-212 a precursor thereof, a miRNA species having a seed region identical therewith, and a miRNA species which is a family member thereof, and/or said post-ischemic cytoprotective miRNA species is selected from the group consisting of miR-125b* miR-33, miR-139-3p miR-320, miR-532-3p, miR-let7e, miR-let7i, miR-1, miR-503, miR-328, miR-181a and miR-7b a precursor thereof, a miRNA species having a seed region identical therewith, and a miRNA species which is a family member thereof, and/or the pre-ischemic cytopathic miRNA species is selected from the group consisting of mir-487b, miR-352, miR-93, a precursor thereof, a miRNA species having a seed region identical therewith, and a miRNA species which is a family member thereof, and/or the post-ischemic cytopathic miRNA species is selected from the group consisting of miR-208, miR-19b, miR-19a, and miR-352, miR-93, miR-487b, miR-494, miR-106b and miR-130a, miR-16, miR-21, miR-22*, miR-26b, miR-30b-5p, miR-30c, miR-30c-1*, miR-30e, miR-339-3p, miR-450a, miR-499, miR-760-5p, miR-99a, miR-99a*.

In a highly preferred embodiment said miRNA compound is administered to the patient within 4 or 3 hours after the ischemic attack or simultaneously with reperfusion and/or less than 6 hour before surgery or intervention.

In a preferred embodiment the up-regulation or down-regulation of said miRNA agonist or miRNA antagonist, respectively, in said mammalian heart tissue sample during preconditioning or postconditioning is assessed by the following method:

i) providing a set of biological samples comprising expressed miRNA species, said set of samples comprising
  a control sample,
  a first sample and
  a second sample and/or
  a third sample
  wherein the samples can be subjected to ischemia, ii) exposing each of the samples to aerobic perfusion for a time-period, and within this time period
  the control sample is exposed neither to ischemia nor to preconditioning nor to postconditioning, thereby obtaining a non-ischemic control sample, and
  exposing the first sample to ischemia, preferably to ischemia and reperfusion, thereby obtaining an ischemic sample, and
  preconditioning the second sample by exposing it to a preconditioning protocol and then to ischemia thereby obtaining a preconditioned sample, and/or
  postconditioning the third sample by exposing it to ischemia and to a postconditioning protocol thereby obtaining a postconditioned sample,
  preferably miRNAs are isolated after not more than 5 hours after ischemia iii) assessing the expression level of said miRNA species
  in the non-ischemic control sample
  in the ischemic sample as compared to the non-ischemic control sample and
  in the preconditioned sample as compared to the non-ischemic control sample and/or
  in the postconditioned sample as compared to the non-ischemic control sample, and iv) calculating the ratio of the expression levels of said miRNA species
  in the preconditioned sample as compared to the ischemic sample and/or
  in the postconditioned sample as compared to the ischemic sample, v) identifying said miRNA species the expression level of which is up-regulated by at least 1.5 fold or down-regulated by at least 1.5 fold, in the preconditioned sample and/or in the postconditioned sample relative to the ischemic/reperfused sample, vi) obtaining the nucleotide sequence of said miRNA species.

In a preferred embodiment the miRNA species in the control heart tissue sample exposed to ischemia and reperfusion is significantly upregulated in comparison with a non-ischemic control sample, significantly downregulated in comparison with a non-ischemic control sample, neither upregulated nor downregulated significantly in comparison with a non-ischemic control sample.

The invention also relates to miRNA compound for use in the prevention or treatment of consequences of ischemic and/or reperfusion injury in a patient predisposed to or affected by ischemia, preferably in the heart of said patient, wherein said miRNA compound is selected from a group consisting of miRNA agonists of any of the following miRNA species: miR-333, miR-188, miR-125b*, miR-139-3p, miR-320, miR-532-3p, miR-451, miR-212, miR-192 miR-139-5p, miR-503, miR-33, miR-328, miR-181a, miR-7b, let7e, let7i, miR-1 and miRNA antagonists of any of the following miRNA species: miR-487b, miR-208, miR-19b, miR-19a, miR-352, miR-93, miR-494 and miR-106b, and miRNA agonists or antagonists comprising a nucleotide sequence identical with or complementer to the seed region of said miRNA species and/or which comprises a 17 to 27 nucleotides long nucleic acid segment the sequence of which is identical to the sequence of said miRNA species or to a complementer thereof, or is different at most in 1, 2, 3, 4, 5 or 6 nucleotide(s) therefrom or from said complementer and any combination thereof.

In the present invention preferably the samples are collected for expression level assessment after at most 1 h, 1.5 h, 2 h, 2.5 h or 3 h after ischemia. Preferably, reperfusion is carried out for at most 1 h, 1.5 h, 2 h, 2.5 h or 3 h after ischemia. Preferably, reperfusion is carried out for at least 0.5 h or 1 h or 1.5 h after ischemia.

In a preferred embodiment the invention also relates to a combination of more than one miRNA compounds according to any of claims 1 to 10, wherein preferably said combination comprises at least a miRNA antagonist and a miRNA agonist, said agonist(s) and antagonist(s) comprising a nucleotide sequence identical with or complementer to the seed region of said miRNA species and/or which comprises a 17 to 27 nucleotides long nucleic acid segment the sequence of which is identical to the sequence of said miRNA species or to a complementer thereof, or is different at most in 1, 2, 3, 4, 5 or 6 nucleotide(s) therefrom or from said complementer, wherein said miRNA compound shows a cell protective effect in a cardiomyocyte cell viability assay.

Preferably said miRNA agonist of miRNA species is selected from the group of miR-139-5p, miR-33, miR-125b*, let-7b, and said miRNA antagonist of miRNA species is selected from the group of miR-494 and miR-487b.

In a preferred embodiment, said miRNA compound is for use in cytoprotection in a tissue endangered by ischemia in a patient predisposed to ischemia, said miRNA compound being administered to said patient before or during surgery or during intervention associated with a risk of ischemia, wherein
  the miRNA compound is
  a miRNA agonists of a pre-ischemic cytoprotective miRNA species, or
  a miRNA antagonists of a pre-ischemic cytopathic miRNA species, preferably a pre-ischemic cytotoxic miRNA species.

The cells, the tissue or the organ may be endangered by ischemia e.g. due to surgery or a therapeutic intervention or due to patient condition. The surgery or intervention is preferably one wherein the ischemic event can be predicted in advance, e.g. in which blood vessels, e.g. an artery or arteries are or may be blocked or blood flow is reduced or there is a risk of occlusion thereof or a risk of sudden hypoperfusion.

The surgery or intervention may be an emergency intervention or elective intervention, cardiac surgery, e.g. percutaneous coronary intervention (PCI) or angioplasty, placement of stents, removal of ill-functioned blood vessels, e.g. varicose veins, lung surgery, transplantation of the heart, lung, kidney, liver, skin, muscle etc., surgery of the brain or nervous system, removal of tumors from the heart, brain, lung, kidney, liver, bowels, peripheral vessel diseases. Preferably the miRNA compounds are applied typically for preventive purposes.

Preferably, the miRNA compound is for use in a patient predisposed to ischemia wherein said patient is under a lingering risk of ischemia and the miRNA compound is administered to said patient regularly for a given period of time, preferably for at least one week, more preferably for at least two weeks, three weeks, one month, two months or more, for cytoprotection in a tissue endangered by ischemia.

In any embodiment of the invention, preferably, the patient predisposed to ischemia is a patient predisposed to acute ischemia and/or acute reperfusion injury. Preferably, the patient is a patient having high risk or at least medium-risk of cardiovascular disease or of ischemic heart disease, preferably of acute ischemia and/or acute reperfusion injury, or preferably ischemic heart attack. Preferably the patient is at risk of dying in one or more of these conditions within the subsequent 15, 12, 10, 8, 5, 3 or 1 year(s).

Preferably the miRNA compound is administered before less than one week, less than one day or less than 12, 8, 6, 5, 4, 3, 2 or 1 hour(s) before surgery or intervention.

In a further preferred embodiment, the miRNA compound is for use in cytoprotection in a tissue of a patient having acute ischemic injury and/or acute reperfusion injury and/or a patient receiving reperfusion therapy, and is administered
  between the ischemic attack and reperfusion, or immediately before reperfusion,
  after the ischemic attack, preferably within three days, one day or half day, more preferably within 6, 5, 4, 3, 2 or 1.5 hours, more preferably within 60, 50, 40 or 30 minutes after the ischemic attack,
  during reperfusion or
  after reperfusion, preferably within three days 60 hours, two days, one day, 24 or 12 hours, more preferably within 6, 5, 4, 3, 2 or 1.5 hours, more preferably within 60, 50, 40, 30, 20 or 10 minutes after reperfusion or simultaneously with reperfusion, wherein
  the miRNA compound is
  a miRNA agonists of a post-ischemic cytoprotective miRNA species, or
  a miRNA antagonists of a post-ischemic cytopathic miRNA species, preferably a post-ischemic cytotoxic miRNA species.
In a preferred embodiment
  the miRNA compound comprises at least 16, 17, 18 or 19 nucleotide units, preferably about 18 to about 25 nucleotide units having or corresponding to the sequence of the miRNA species or a sequence different in 1, 2 or 3 nucleotide unit(s) therefrom, or
  the miRNA compound is a complementer, inhibitor or antagonist of the miRNA species, said miRNA compound comprising at least or at least 14, 15, 16, 17, 18 or 19 nucleotide units, or about 18 to about 25 nucleotide units, having or corresponding to the complementer of the sequence of the miRNA species or at least the seed region thereof, or a sequence different in 1, 2 or 3 nucleotide unit(s) therefrom, or said miRNA compound comprising at least 7, 8, 9 nucleotide units, having or corresponding to the complementer of at least the seed region of the sequence of the miRNA species.

Preferably, the miRNA agonist is a miRNA mimic of said miRNA species.

Preferably, the miRNA antagonist is a miRNA inhibitor, preferably an antagomir of said miRNA species.

In a preferred embodiment assessing the expression level of miRNA species is carried out by RNA array or miRNA array or "chip" technology or by quantitative RT-PCR technology.

The invention also relates to a pharmaceutical composition for use in the treatment of a patient predisposed to or affected by ischemia to protect cells or tissues against consequences of ischemic injury and/or reperfusion injury in said patient, said composition comprising one or more miRNA compound as defined in any of claims 1 to 13 and pharmaceutically acceptable excipient, wherein preferably
  said composition comprises one or more miRNA compound selected from
    one or more miRNA agonists of one or more pre-ischemic cytoprotective miRNA species,
    one or more miRNA antagonists of one or more pre-ischemic cytopathic miRNA species,
    one or more miRNA agonists of one or more post-ischemic cytoprotective miRNA species, and/or
    one or more miRNA antagonists of one or more post-ischemic cytopathic miRNA species.

Preferably, said pharmaceutical composition is for use in a treatment to protect cells, tissues and/or organs against short term and/or direct consequences of acute ischemic and reperfusion injury in a patient predisposed to or affected by ischemia, in the heart of a patient predisposed to or attacked by acute ischemia, said composition comprising one or more miRNA compound as defined herein and pharmaceutically acceptable excipient.

According to the invention, preferably,
  the miRNA agonist is the agonist of a miRNA species which is simultaneously a pre-ischemic cytoprotective miRNA species and a post-ischemic cytoprotective miRNA species, and/or
  the miRNA antagonist is the antagonist of a miRNA species which is simultaneously a pre-ischemic cytopathic miRNA species and a post-ischemic cytopathic miRNA species,
  said miRNA agonist or antagonist being useful both for protecting cells and/or tissue in said patient against acute ischemic injury and against reoccurring ischemic attack.

According to the invention the ischemia-reperfusion injury comprises cardiovascular ischemia-reperfusion injury.

According to the invention, e.g. in the pharmaceutical composition or in the therapeutic method of the invention at least one miRNA agonist and at least one miRNA antagonist is applied together.

In a further preferred embodiment the one or more miRNA compound is administered together with one or more further compound for the prevention or treatment of a condition as disclosed herein. Preferably said one or more further compound is selected from compounds used in ischemic heart disease (organic nitrates, beta-blockers, calcium antagonists, angiotensin convertase enzyme inhibitors, metabolic modulators such as e.g. trimetazidine), vasodilators, fibrinolytic agents, anti-platelet agents, anti-inflammatory agents, agents that reduce heart rate such as e.g. ivabradin, as well as compounds used in alleviating risk factors for ischemic heart disease (antihyperlipidemic agents such as e.g. statins, anti-diabetic compounds, antihypertensive agents, anti obesity agents, etc)

Application or administration of multiple compounds can take place either sequentially or simultaneously.

In a preferred embodiment the pharmaceutical composition comprises multiple compounds. In a further embodiment the invention relates to a pharmaceutical kit comprising multiple compounds.

The invention also relates to a method for identifying a micro-RNA (miRNA) species as a target for treatment to protect cells or tissues against consequences of acute ischemic injury in a patient predisposed to or attacked by ischemia, i) providing a set of biological samples comprising expressed miRNA species, said set of samples comprising
a control sample,
a first sample and
a second sample and/or
a third sample
wherein the samples can be subjected to ischemia,
ii) exposing each of the samples to aerobic perfusion for a time-period, and within this time period
the control sample is exposed neither to ischemia nor to preconditioning nor to postconditioning thereby obtaining a non-ischemic control sample, and
exposing the first sample to ischemia thereby obtaining an ischemic sample, and
preconditioning the second sample by exposing it to a preconditioning protocol and then to ischemia thereby obtaining a preconditioned sample, and/or
postconditioning the third sample by exposing it to ischemia and to a postconditioning protocol thereby obtaining a postconditioned sample,
iii) assessing the expression level of miRNA species
in the non-ischemic control sample
in the ischemic sample as compared to the non-ischemic control sample and
in the preconditioned sample as compared to the non-ischemic control sample and/or
in the postconditioned sample as compared to the non-ischemic control sample, and
iv) calculating the ratio of the expression levels of said miRNA species
in the preconditioned sample as compared to the ischemic sample and/or
in the postconditioned sample as compared to the ischemic sample,
v) identifying an miRNA species the expression level of which is up-regulated by at least 1.3 fold, preferably by at least 1.5 fold or down-regulated by at least 1.3 fold, preferably by at least 1.5 fold in the preconditioned sample and/or in the postconditioned sample relative to the ischemic sample. Preferably, the miRNA species are termed as defined above dependent on their up- or down-regulation in the samples.

In a preferred method of the invention steps the calculated ratios of the expression levels are obtained by
a) assessing the expression level of miRNA species
in the non-ischemic control sample
in the ischemic/reperfused sample and
in the preconditioned sample and
in the postconditioned sample
b) calculating the ratio of the expression levels of said miRNA species
in the ischemic/reperfused sample relative to non-ischemic control sample in the preconditioned sample relative to non-ischemic control sample
in the postconditioned sample relative to non-ischemic control sample
in the preconditioned sample relative to the ischemic/reperfused sample and/or
in the postconditioned sample relative to the ischemic/reperfused sample.

According to the invention a method is also provided herein for treating ischemia-reperfusion injury, including cerebrovascular disease and ischemic heart disease, comprising administering to a subject in need of such a treatment a miRNA compound according to the invention.

The invention further relates to a method for treatment of a patient predisposed to or affected by ischemia to protect cells or tissues against consequences of ischemic injury and/or reperfusion injury in said patient, said method comprising administering to said patient an miRNA compound according to the invention.

Preferably, the ischemic injury is acute ischemic injury and the reperfusion injury is acute reperfusion injury.

In a preferred embodiment, the miRNA compound is administered to said patient before or during surgery or intervention associated with a risk of ischemia, for cytoprotection in a tissue endangered by ischemia, wherein
the miRNA compound is
a miRNA agonist of a pre-ischemic cytoprotective miRNA species as defined herein or
a miRNA antagonist of a pre-ischemic cytopathic miRNA species as defined herein.

Preferably, the miRNA compound is administered before less than one week, less than one day or less than 12, 8, 6, 5, 4, 3, 2 or 1 hour(s) before surgery or intervention.

In a further preferred embodiment, the miRNA compound is administered to a patient having acute ischemic injury and/or acute reperfusion injury or receiving reperfusion therapy,
between the ischemic attack and reperfusion, or immediately before reperfusion
during reperfusion or
after reperfusion, preferably within one day, more preferably within 5, 4, 3, 2 or 1.5 hours, more preferably within 60, 50, 40 or 30 minutes after reperfusion, wherein
the miRNA compound is
a miRNA agonist of a post-ischemic cytoprotective miRNA species as defined herein or
a miRNA antagonist of a post-ischemic cytotoxic miRNA species as defined herein.

Unless specifically indicated otherwise, in the present disclosure one or more embodiments or features described in respect of a given aspect or embodiment of the invention can be combined with any other aspect or embodiment disclosed herein provided that it is technically reasonable for a person skilled in the art and provides the contribution to the prior art according to the present invention.

DISCLAIMERS

Optionally, the invention does not relate to one or more of the following miRNA species and/or the corresponding miRNA compound(s), or uses thereof, or said miRNA species and/or compounds are not contemplated:

i) in one or more embodiments, optionally: miR-134, miR-212, miR-214, miR-21, miR-129, miR-182, and miR-290 or an agonist thereof, ii) in one or more embodiments, optionally: miR-192, miR-30c, miR-494, miR-497 or an agonist or antagonist thereof, iii) in one or more embodiments, optionally: an antagonist or inhibitor of the miR-15 family (miR-15a, mir-15b, miR-16, miR-195, miR-424 and miR-497), iv) in one or more embodiments, optionally: an antagonist of a let-7 family member, miR-15b, miR-21, miR-199a, miR-199b, miR-214, miR-10a, miR-10b, miR-16, miR-146a, miR-146b, miR-221, miR-222, a miR-30 family member, miR-497, miR-20a, and/or an agonist of miR-20b, miR-93, miR-101, miR-126, miR-143, miR-145, miR-150 and miR-29a-c, v) in one or more embodiments, optionally: antagonist or inhibitor of miR-208a or miR-208b or an inhibitor of miR-499 or a combination thereof, vi) in one or more embodiments, optionally: antagonist or inhibitor of miR-24 and/or miR-328, vii) in one or more embodiments, optionally: an antagonist of the miR-15 family (e.g. miR-15a, miR-15b, miR-16-1, miR-16-2, miR-195, miR-424 and miR-497), miR-30 family (miR-30a, miR-30b, miR-30c, miR-30d, miR-30e), miR-92a, miR-320, miR-20, miR-199a, miR-499a, and/or an agonist of miR-126, miR-143, miR-210 and miR-29a-c, viii) in one or more embodiments, optionally: one or more miRNA oligonucleotides disclosed in WO2010103015A1 ix) in one or more embodiments, optionally: agonist of miR-1 and/or miR-133 and/or miR-320

Optionally, the invention does not relate to one or more miRNA species and/or the corresponding miRNA compound(s), or uses thereof, disclosed in the prior art and being obtainable by the method of the invention wherein the method of the invention is not disclosed in the prior art in connection with said miRNA species or compound.

Optionally, the invention does not relate to one or more of the above miRNA-species and/or miRNA-compound(s) for use in any of the treatment of any of the diseases as disclosed herein.

DEFINITIONS

An "miRNA (microRNA) species" is a naturally occurring ribonucleic acid (RNA) molecule which is a small, about 18 to about 25 nucleotides long non-coding RNA molecule that is an endogenous physiological regulator of gene expression. [Bartel D P 2004]. MiRNAs play an essential role in the posttranscriptional regulation of gene expression by repression or activation of translation/transcription ("RNA interference").

An "miRNA compound" is a synthetic or artificial nucleic acid compound which is an agonist or an antagonist of a miRNA species.

A "nucleic acid compound" is an organic molecule comprising a nucleic acid consisting of nucleotide units having a specific sequence which can be determined by chemical or biochemical method and optionally comprising one or more further moieties e.g. for improved biological function, stability, targeting, reporting or detectability.

An "miRNA agonist" of a miRNA species is a nucleic acid compound which, once introduced into a biological material, e.g. cells or tissue, due to its nucleotide sequence, produces the same type of a biological effect or pattern of effects, e.g. induce the regulation of the same gene or genes as the corresponding miRNA species in the same biological material.

An "miRNA mimic" is a miRNA agonist which is an artificial (man-made) double-stranded RNA or RNA derivative which mimics mature endogenous miRNAs after transfection into cells. The miRNA mimic may be chemically synthesized or recombinantly produced and processed from a precursor. Optionally, an miRNA mimic may comprise one or more modified or artificial base(s), sugar unit(s) or internucleotide linkage(s).

An "miRNA antagonist" of a miRNA species is, in a broader sense, any compound which is capable of reducing, inhibiting or blocking the regulatory effect of an miRNA. Preferably, it is a nucleic acid compound which, once introduced into a biological material, e.g. cells or tissue, due to its nucleotide sequence, antagonizes the effect of the corresponding miRNA species in the same biological material, e.g. inhibits or silences the regulation of said miRNA species on a gene or genes.

An "miRNA inhibitor" is a any nucleic acid reducing the expression level (down-regulating) an miRNA or inhibiting its binding to its target sequence or the RISC complex.

A preferred miRNA inhibitor is an "antagomir", i.e. a chemically engineered oligonucleotide useful in silencing endogenous microRNA. Preferably, an antagomir has a sequence which is antisense to the sequence of an miRNA, or to part thereof, or to a mutant thereof which is different in 1, 2 or 3 nucleotides from the miRNA.

In a preferred embodiment, the miRNA compound has a nucleic acid moiety comprising a nucleotide sequence identical with or complementer to the seed region of the corresponding miRNA species.

In a preferred embodiment, an miRNA compound is a nucleic acid compound which comprises a 17 to 27 nucleotides long, preferably 18 to 24 or 19 to 24 or 19 to 23 nucleotides long nucleic acid segment, the sequence of which ("core sequence") is identical to the sequence of a mature miRNA species or to a complementer thereof, or is different at most in 1, 2, 3, 4, 5 or 6 nucleotide(s) therefrom or from its complementer, while maintaining the agonizing or antagonizing effect. An miRNA compound may also comprise modified bases (in this case in the sequence a modified base is to be considered as the starting base from which it is modified), or artificial bases; if it is not evident which of the four natural RNA bases correspond to the artificial base then the artificial base is to be considered in the sequence as a difference or mutation. miRNA compound may also comprise any modified internucleotide linkage or linkages Such modified linkages are well known in the art and suitable, for example for stabilizing oligonucleotides. Moreover, the miRNA compound may comprise flanking regions which flank the core sequence.

"Ischemia" is a restriction, i.e. an absolute or relative shortage in blood supply to a tissue or cells of a tissue or to a whole organ with resultant damage or dysfunction of the tissue with a consequence of reduced oxygen delivery to the tissue (hypoxia). Insufficient blood supply leads to hypoxic tissue (anoxic in case of no oxygen supply at all) with the consequence of necrosis, apoptosis or autophagy which all determine the cell-death.

Ischemia is "acute ischemia" if it is due to an ischemic attack, preferably a sudden shortage of blood supply due to e.g. embolism, thrombosis, thromboembolism (blood clots), sudden obstruction of a blood vessel, e.g. by surgery, occurrence of foreign bodies in the circulation or vascular injury. "Acute ischemia" is to be treated within 3 or 2 days, preferably within 24 or 12 hours, more preferably within 6, 5, 4, 3, 2 or 1.5 hours from the onset of symptoms. Short term consequences of acute ischemia are directly the consequences of cell death. In case of cardiac ischemia cell death results in pumping failure of the heart, causing hypotension/hypoperfusion of other organs (brain, kidney, bowels, etc.), this is known as cardiogenic shock. The cell death also results in altered electrical activity of myocardial cells, very often resulting in life threatening arrhythmias (tachycardia, fibrillation, bundle branch block), causing sudden cardiac death. Death of papillary muscles often results in cardiac valve dysfunction, thereby causing regurgitation of blood and ineffective pump function. Death of the cardiac cell may cause aneurysm formation and rupture of the myocardial wall.

Acute ischemia of the brain is "stroke".

In "chronic ischemia" the shortage in blood supply is developed gradually and is partial, due to e.g. atherosclerosis (lipid-laden plaques obstructing the lumen of arteries), hypotension (e.g. in sepsis or heart failure) etc.

Ischemia may be cardiac ischemia, e.g. ischemia of the myocardium.

In a "transient ischemic attack" (TIA) the ischemic symptoms disappear within a few minutes. TIAs are usually caused by a blood clot blocking one of the blood vessels leading to the given tissue (e.g. brain, heart, liver or kidney).

A "patient predisposed to ischemia" is a patient who is inclined to, susceptible to, is endangered by an ischemic attack, for example a patient who
- has experienced an ischemic attack [e.g. a patient at risk for postoperative myocardial infarction (PMI)],
- shows any genetic or metabolic risk factor of metabolic syndrome, diabetes, obesity, hypertension, atherosclerosis, high level of low density lipoprotein cholesterol, elevated serum homocysteine, increased platelet function or deteriorated platelet function, smoking, low level of daily physical exercise, in particular aerobic exercise, or multiple risk factors,
- is or is to be subjected to a therapeutic intervention increasing the risk of ischemia, e.g. an intervention resulting in a hypoxic state, e.g. a surgical intervention, in particular a surgery in which the cardiovascular system is involved etc. For example, the intervention can be an elective cardiac interventions, such as elective PCI, heart surgery, coronary artery bypass graft surgery (CABG) or (early) surgical revascularization e.g. after an acute myocardial infarction (AMI).

"Reperfusion" is the restoration of blood supply to a tissue which is ischemic due to decrease in normal blood supply. The decrease may result from any source including atherosclerotic obstruction, narrowing of the artery, or surgical clamping. Reperfusion may occur spontaneously or may be effected as a part of a treatment. It is primarily a procedure for treating infarction or other ischemia, by enabling viable ischemic tissue to recover, thus limiting further necrosis and therefore infarct size. However, reperfusion can itself further damage the ischemic tissue, causing reperfusion injury.

"Ischemic and reperfusion injury" or "reperfusion injury" or "ischemic-reperfusion injury" (I/R injury) is understood herein as any functional, metabolic and/or structural changes, including necrosis, apopotosis, and autophagy, in ischemic tissues which are consequences of reperfusion, or ischemia and reperfusion together, to any area of the tissue affected by ischemia.

"Acute ischemic-reperfusion injury" or "acute reperfusion injury" refers to ischemic-reperfusion injury, i.e. any consequences, preferably short term and/or direct consequences of reperfusion, or ischemia and reperfusion together. In a sense in acute reperfusion injury as a consequence cell death occurs, at least pre-eminently, via a necrotic and/or apoptotic mechanism and/or via autophagy.

In a sense acute reperfusion injury is insensitive to anti-inflammatory treatment. In a sense any consequence, optionally cell death occurs during or soon after or immediately after reperfusion, preferably within one day, more preferably within 5, 4, 3, 2 or 1.5 hours, more preferably within 60, 50, 40 or 30 minutes after reperfusion.

Much of the consequences and damage that occur after an acute ischemia-reperfusion injury is caused by acute inflammatory responses during reperfusion, the restoration of blood flow to the affected organ.

"Acute myocardial infarction" (AMI) is myocardial infarction occurring during the period when circulation to a region of the heart is obstructed and myocardial cell death due to necrosis, apoptosis or autophagy is occurring. AMI is to be treated within 3 or 2 day(s), preferably within 12 hours or 6 hours, more preferably within 5, 4, 3, 2 or 1.5 hours from the onset of symptoms. AMI is characterized by acute ischemia and acute reperfusion injury.

"Ischemic heart disease" (IHD) or myocardial ischemia is a disease characterized by ischemia of the heart muscle. IHD includes acute myocardial infarction that causes death of myocardial tissue thereby acute heart failure and arrhythmias, as well as chronic myocardial infarction causing cardiac tissue remodeling and heart failure.

"Ischemic preconditioning" is the exposure of the tissue (e.g. myocardium, kidney or nervous tissue) endangered by ischemia to brief, repeated periods of hypoxia, preferably ischemia (e.g. by vascular occlusion).

In an embodiment ischemic preconditioning includes exposure of the tissue by an external effect having the same result in the tissue as said repeated periods of hypoxia; this can be achieved e.g. by treatment with pharmaceutical, physical, and chemical agents mimicking the preconditioning effect. Preconditioning has a cardioprotective effect, renders the tissue resistant to the deleterious effects of ischemia or reperfusion and lessens myocardial infarct size and dysfunction and arrhythmias after ischemia.

A "preconditioning protocol" is the sequence of a given number of time-periods of hypoxia, preferably with a given time-period of normal oxygen supply, e.g. by reperfusion between them. For example, the time-period of pre-exposure may be e.g. 1 to 10, minutes, 2 to 8, 7 or 6 minutes, more preferably about 3 to 6 or 5 minutes and the number of times the tissue is exposed to ischemia and reperfusion may vary.

"Ischemic postconditioning" is the exposure of the tissue (e.g. myocardium, kidney or nervous tissue) attacked by ischemia to brief, repeated periods of hypoxia, preferably ischemia (e.g. by vascular occlusion) briefly after ischemia. In an embodiment ischemic preconditioning includes exposure of the same tissue or any remote tissue in the body by an external effect having the same result in the tissue as said repeated periods of hypoxia; this can be achieved e.g. by treatment with pharmaceutical, physical, and chemical agents mimicking the preconditioning effect. Postconditioning has a cardioprotective effect, renders the tissue resistant to the deleterious effects of ischemia-reperfusion injury and lessens myocardial infarct size and dysfunction and arrhythmias after ischemia.

A "postconditioning protocol" is the sequence of a given number of time-periods of hypoxia, preferably with a given time-period of normal oxygen supply, e.g. by reperfusion between them after an ischemic attack. For example, the time-period of pre-exposure may be e.g. half minute to 10 minutes, more preferably about 1-2 minutes and the number of times the tissue is exposed to ischemia and reperfusion may vary from 1 to 10, or preferably from 1 to 6.

A "cytopathic" effect is understood herein as an effect pertaining to, relating to or characterized by any adverse change or effect at least at the cellular level either detectable or not. A cytopathic effect may be the consequence of an intracellular or extracellular effect, e.g. contacting the cells by a cytopathic agent or hypoxia, ischemia, e.g. acute myocardial infarction or stroke, or ischemia-reperfusion injury, e.g. acute ischemia-reperfusion injury.

A "cytotoxic" effect is understood herein as an effect pertaining to, relating to or characterized by detectable damaging, degenerative or pathologic changes at the cellular level or the effect of a disease or disorder having an effect at the cellular level.

A "cytoprotective" effect is understood herein as an effect of a miRNA species or miRNA compound which reduces or inhibits the cellular damage, caused by an external or internal e.g. biological effect, e.g. a cytotoxic effect.

A "biological sample" is to be understood herein as any biological material which comprises biological material in which miRNAs can be up- and/or down-regulated due to an external effect and the biological sample can be subjected experimentally (i.e. in a test to any condition selected from a test ischemia-reperfusion, hypoxia, preconditioning, postconditioning).

The biological sample can be a cell, a group or aggregate of cells, a cell culture, a tissue sample, organ, or a model animal body.

A "tissue sample" is a biological sample which is a tissue culture, a sample taken by biopsy, or an isolated organ. In a preferred embodiment of the invention an isolated organ is applied.

"Administration of" an effective amount of miRNA compound to a mammal is understood herein to include any way of administration of a compound which results in the presence of said miRNA compound in said mammal even if not the miRNA compound itself is introduced into said mammal. In particular, this term covers administration of a precursor miRNA or of a composition from which said miRNA compound is released or administration of a vector e.g. an expression vector resulting in the presence of said miRNA at a level providing an effective amount. Route of administration included oral, intravenous, intracutaneous, subcutaneous, intramuscular, topical, inhaling.

"Percutaneous Coronary Intervention" (PCI), also known as angioplasty involves the insertion of a balloon-type device into a patient's artery to widen and open the blocked artery.

Hearts isolated from male Wistar rats were subjected to either time-matched aerobic perfusion (i.e., non-ischemic control, C), or 30 min regional ischemia and 120 min reperfusion (IR) or to preconditioning with 3×5 min ischemia-reperfusion followed by 30 min regional ischemia and 120 min reperfusion (PRE), or to postconditioning (POST) protocol (6×10 s global ischemia-reperfusion applied immediately after 30 min regional ischemia and followed by 120 min reperfusion). Coronary flow was measured at the indicated time points in order to verify the success of coronary occlusions. Coronary effluent was collected upon the first 5 min of reperfusion after regional ischemia for LDH release detection. Infarct size was measured at the 120th min of reperfusion. For miRNA isolation, in separate experiments, left ventricles were frozen in liquid nitrogen at the end of the perfusion protocol.

Figure 2:
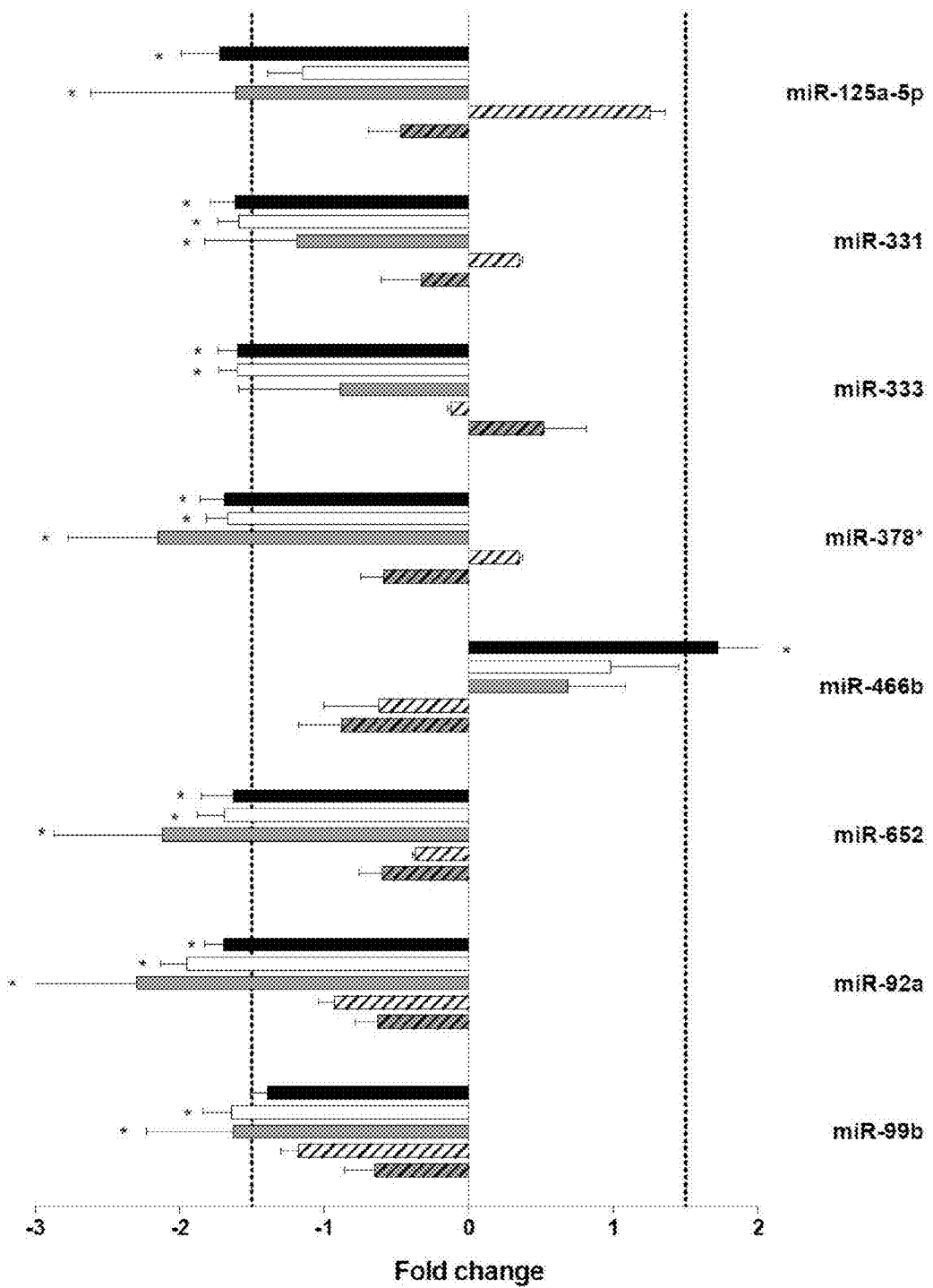

FIG. 2 Cardiac MiRNAs Associated with ischemia-reperfusion Injury.

This graph shows miRNAs that were significantly changed by ischemia-reperfusion as compared to non-ischemic controls but neither pre- nor postconditioning influenced their changes significantly due to ischemia-reperfusion. These results suggest that these miRNAs are probably unaffected by cardioprotective mechanisms. Bars show alterations in miRNA expression in ischemia-reperfusion vs. non-ischemic control (IR/C, black bars); preconditioning vs. non-ischemic control (PRE/C, white bars); postconditioning vs. non-ischemic control (POST/C, grey bars) or to preconditioning vs. ischemia-reperfusion (PRE/IR, white hatched bars); postconditioning vs. ischemia-reperfusion (POST/IR, grey hatched bars). Values are fold expression changes±standard deviation. * represents $p<0.05$ and a fold change of $\geq \pm 1.5$.

Figure 3:
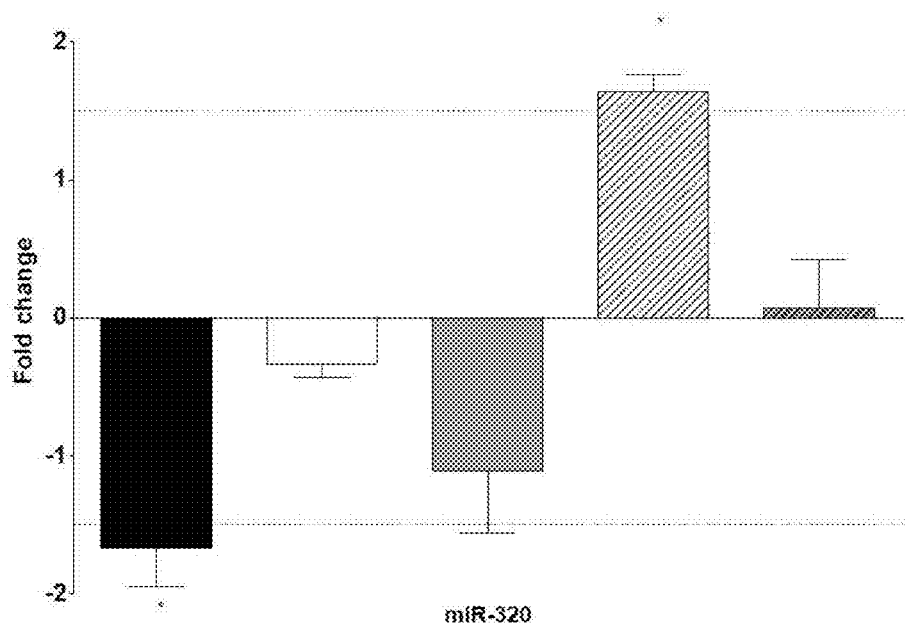
Figure 3:
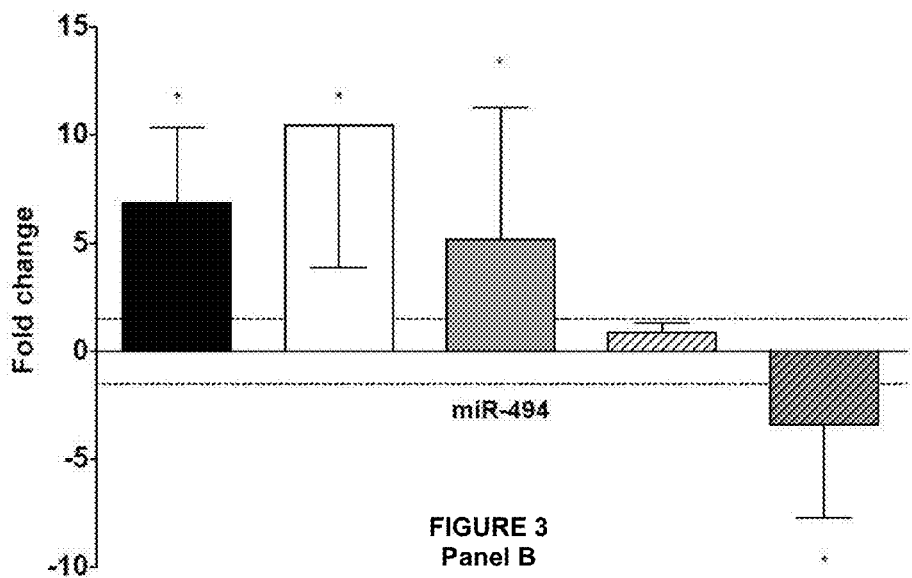
Figure 3:
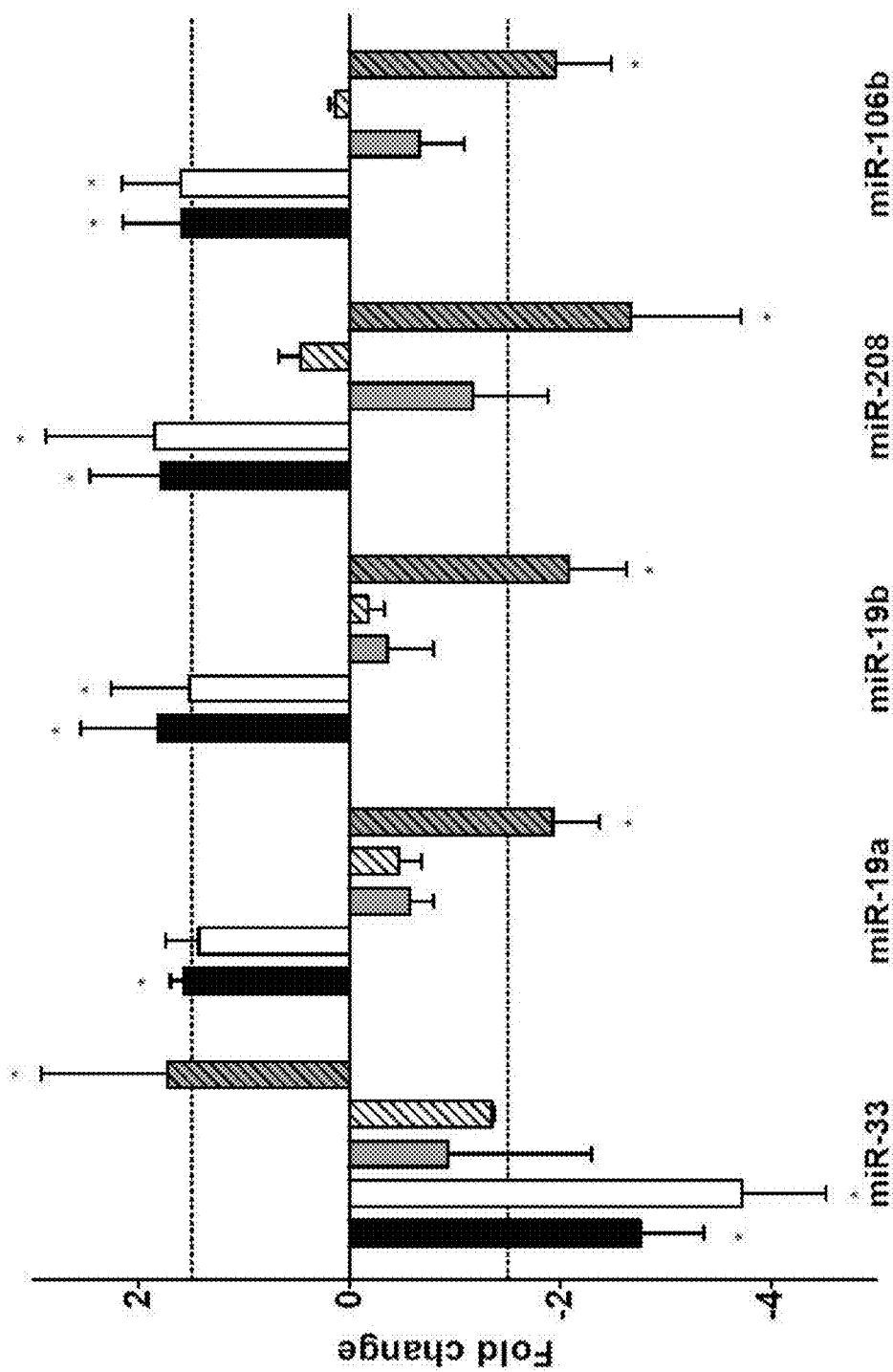

FIG. 3 MiRNAs involved in Cardioprotection by Either Preconditioning (Panel A) or Postconditioning (Panels B and C) on the Basis of Counter Regulation of ischemia-reperfusion Injury This graph shows miRNAs that were significantly changed by ischemia-reperfusion as compared to non-ischemic controls, however, either preconditioning (A) or postconditioning (B and C) significantly reversed their expression changes due to ischemia-reperfusion. This shows that these miRNAs are involved in cardioprotection by either pre- or postconditioning via a reversal of the deleterious mechanisms of ischemia-reperfusion whereas the miRNAs themselves may have either cardioprotective (miR-33, miR-320) or cytotoxic (miR-497, miR-19a, miR-19b, miR-208 and miR-106) effect.

Bars show alterations in miRNA expression in ischemia-reperfusion vs. non-ischemic control (IR/C, black bars); preconditioning vs. non-ischemic control (PRE/C, white bars); postconditioning vs. non-ischemic control (POST/C, grey bars) or to preconditioning vs. ischemia-reperfusion (PRE/IR, white hatched bars); postconditioning vs. ischemia-reperfusion (POST/IR, grey hatched bars). Values are fold expression changes±standard deviation. * represents $p<0.05$ and a fold change of $\geq \pm 1.5$.

Figure 4:
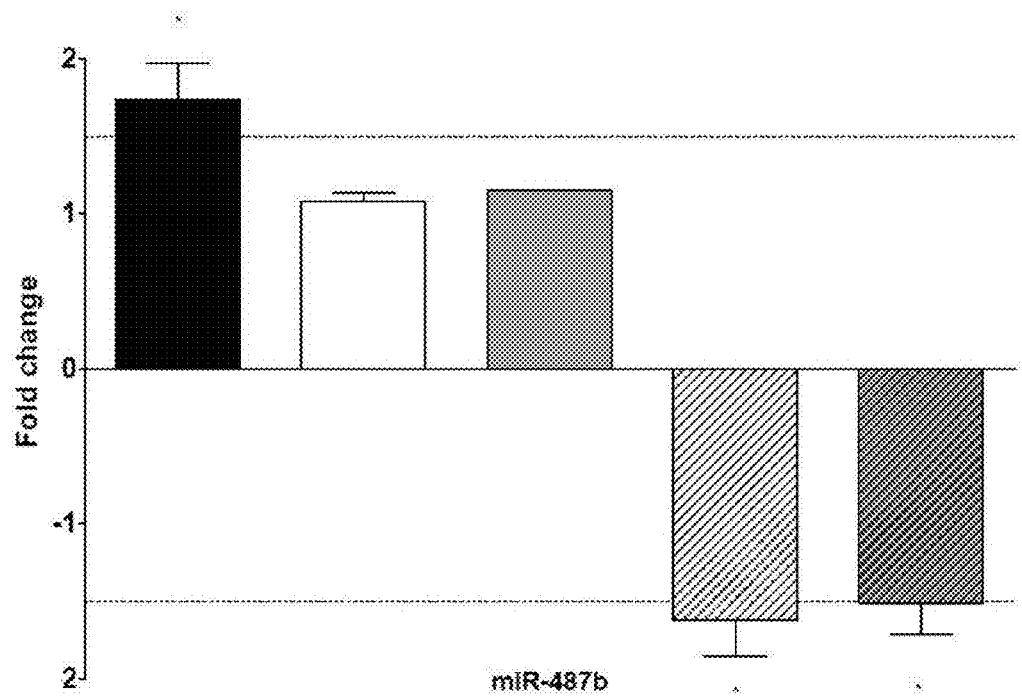
Figure 4:
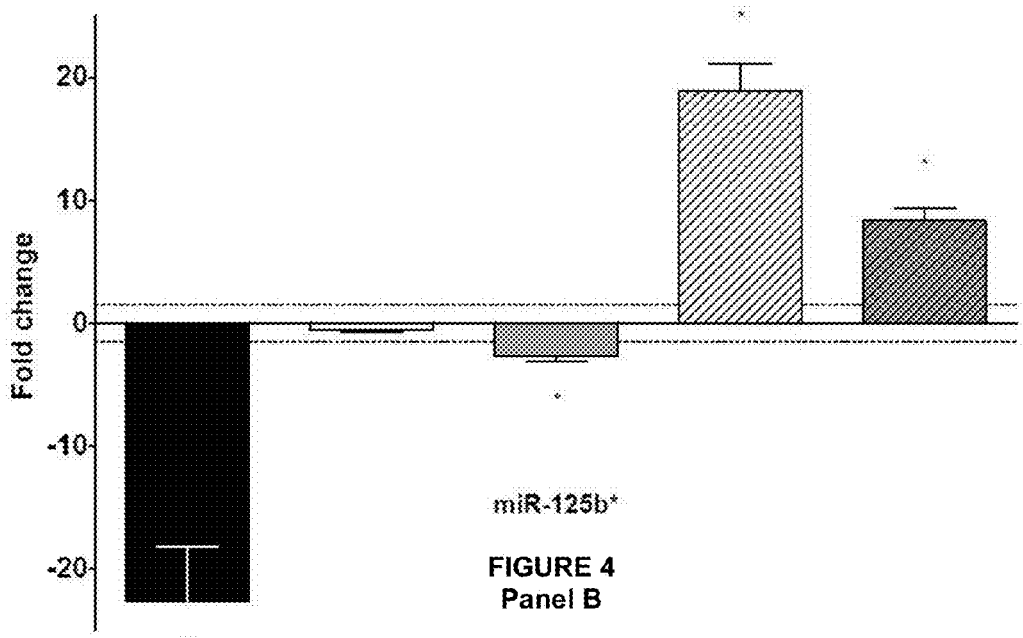

FIG. 4 MiRNAs involved in Cardioprotection by both Preconditioning and Postconditioning on the Basis of Counter Regulation of ischemia-reperfusion Injury (Panels A and B) or on the basis of common cardioprotection-induced mechanisms (Panel C)

This graph shows miRNAs that were significantly changed by ischemia-reperfusion as compared to non-ischemic controls (panels A and B), however, both preconditioning and postconditioning significantly reversed their expression changes due to ischemia-reperfusion. This shows that these miRNAs are involved in cardioprotection by both pre- and postconditioning, possibly (in particular in case of miRNAs shown on panels A and B) via a reversal of the deleterious mechanisms of ischemia-reperfusion. In case of miRNAs in panel C the up-regulation or down-regulation as compared to the non-ischemic control is not significant, but a significant down-regulation (miR-352, miR-93) or up-regulation miR-532-3p), respectively, in both preconditioning and postconditioning occurs indicating that the mechanism is probably the same. Bars show alterations in miRNA expression in ischemia-reperfusion vs. non-ischemic control (IR/C, black bars); preconditioning vs. non-ischemic control (PRE/C, white bars); postconditioning vs. non-ischemic control (POST/C, grey bars) or to preconditioning vs. ischemia-reperfusion (PRE/IR, white hatched bars); postconditioning vs. ischemia-reperfusion (POST/IR, grey hatched bars). Values are fold expression changes±standard deviation. * represents p<0.05 and a fold change of ≥±1.5.

FIG. 5 MiRNAs involved in Cardioprotection On the Basis of Preconditioning-Induced Mechanisms This graph shows miRNAs that were significantly induced by preconditioning as compared both to ischemia-reperfusion and to non-ischemic controls, demonstrating that these miRNAs are specifically induced by preconditioning and have a role in cardioprotective adaptation (can be termed as Protectomirs). Thus, these miRNA have a cardioprotective effect by a mechanism also activated in preconditioning. Bars show alterations in miRNA expression in ischemia-reperfusion vs. non-ischemic control (IR/C, black bars); preconditioning vs. non-ischemic control (PRE/C, white bars); postconditioning vs. non-ischemic control (POST/C, grey bars) or to preconditioning vs. ischemia-reperfusion (PRE/IR, white hatched bars); postconditioning vs. ischemia-reperfusion (POST/IR, grey hatched bars). Values are fold expression changes±standard deviation. * represents p<0.05 and a fold change of ≥±1.5.

Figure 6:
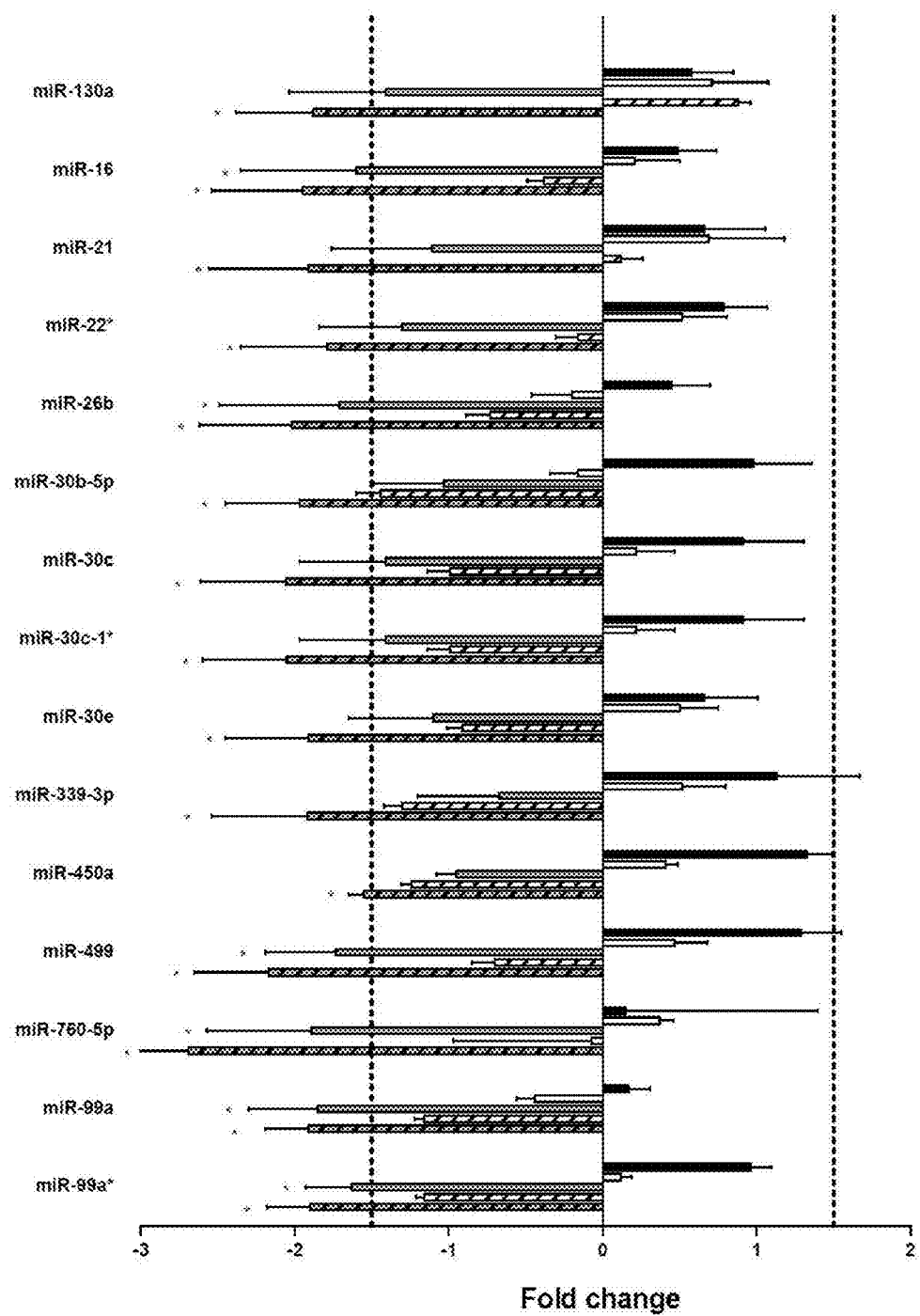

FIG. 6 MiRNAs involved in Cardioprotection On the Basis of Postconditioning-Induced Mechanisms (Panels A and B)

This graph shows miRNAs that were significantly altered by postconditioning as compared to ischemia-reperfusion, demonstrating that these miRNAs are specifically altered by postconditioning. These miRNAs have to be down-regulated so that a postconditioning induced cardioprotection may occur and therefore the microRNAs themselves can be termed as Pathomirs. Bars show alterations in miRNA expression in ischemia-reperfusion vs. non-ischemic control (IR/C, black bars); preconditioning vs. non-ischemic control (PRE/C, white bars); postconditioning vs. non-ischemic control (POST/C, grey bars) or to preconditioning vs. ischemia-reperfusion (PRE/IR, white hatched bars); postconditioning vs. ischemia-reperfusion (POST/IR, grey hatched bars). Values are fold expression changes±standard deviation. * represents p<0.05 and a fold change of ≥±1.5. Thus, cardioprotection may be available via inhibitors against these miRNAs.

Figure 7:
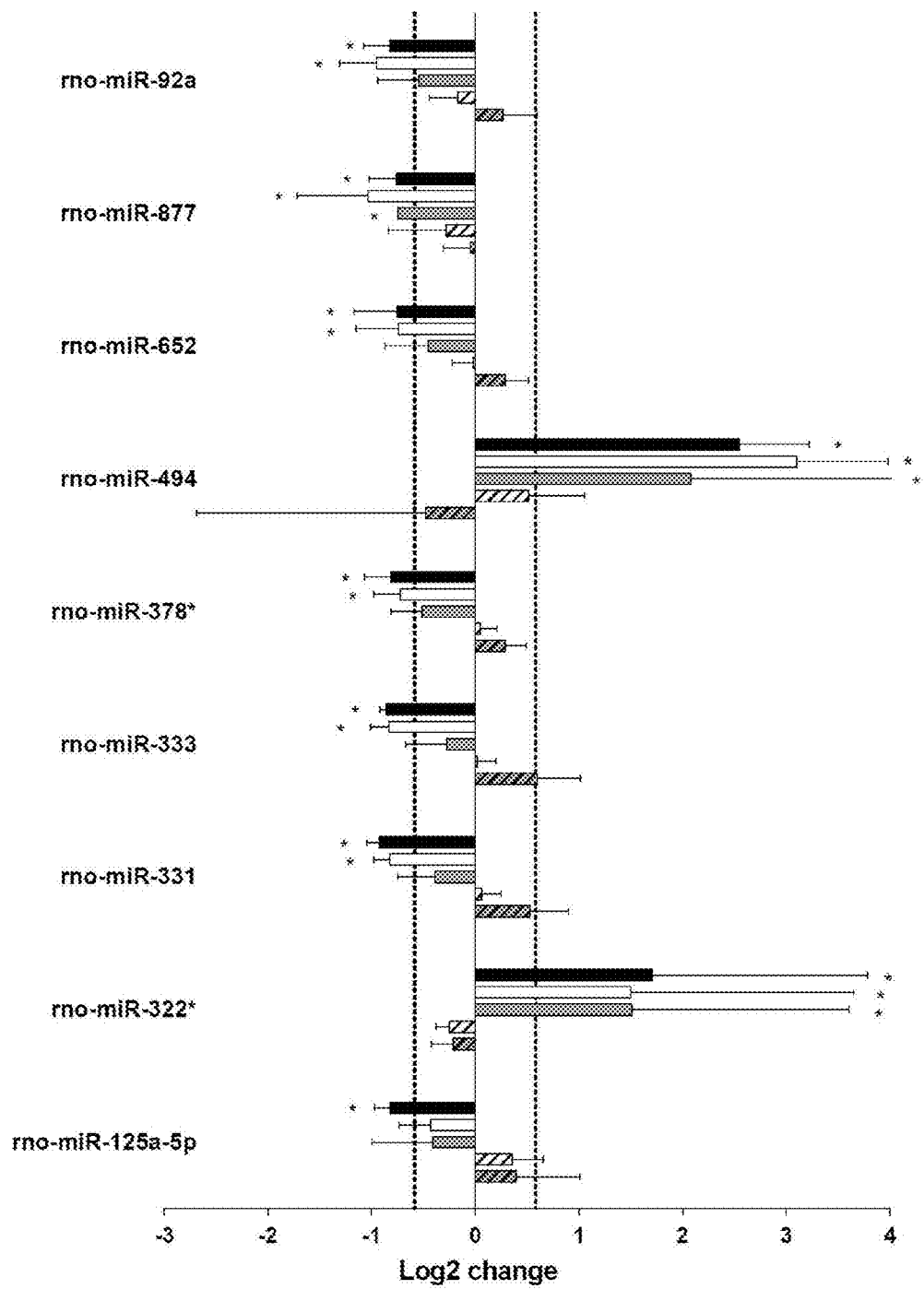

FIG. 7 Cardiac MiRNAs Associated with ischemia-reperfusion Injury.

This graph shows miRNAs that were significantly changed by ischemia-reperfusion as compared to non-ischemic controls but neither pre- nor postconditioning influenced their changes significantly due to ischemia-reperfusion. These results suggest that these miRNAs are probably unaffected by cardioprotective mechanisms. Bars show alterations in miRNA expression in ischemia-reperfusion vs. non-ischemic control (IR/C, black bars); preconditioning vs. non-ischemic control (PRE/C, white bars); postconditioning vs. non-ischemic control (POST/C, grey bars) or to preconditioning vs. ischemia-reperfusion (PRE/IR, white hatched bars); postconditioning vs. ischemia-reperfusion (POST/IR, grey hatched bars). Values are log 2 of the fold expression changes±standard deviation. * represents p<0.05 and a log 2 fold change of <−0.585 or >0.585.

Figure 8:
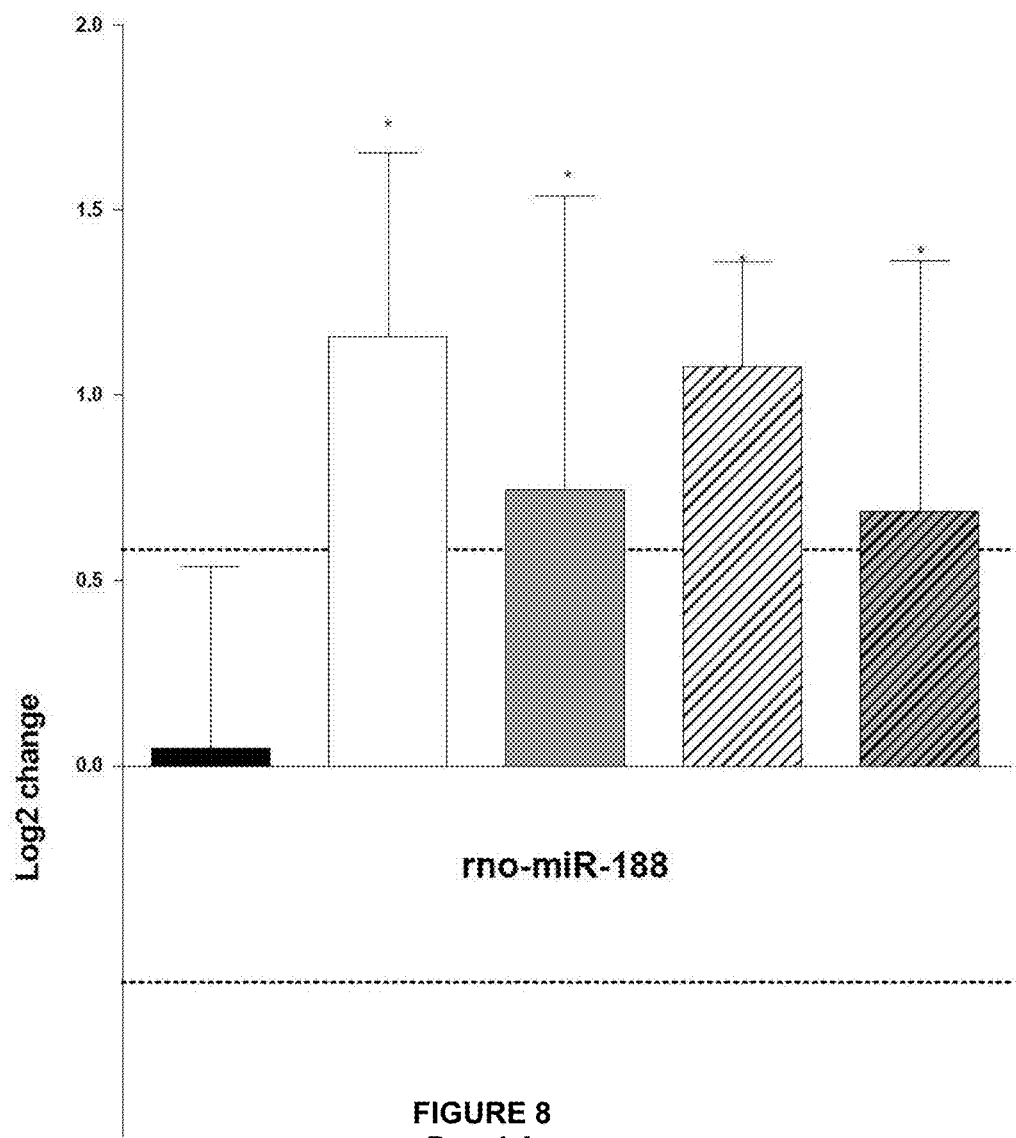
Figure 8:
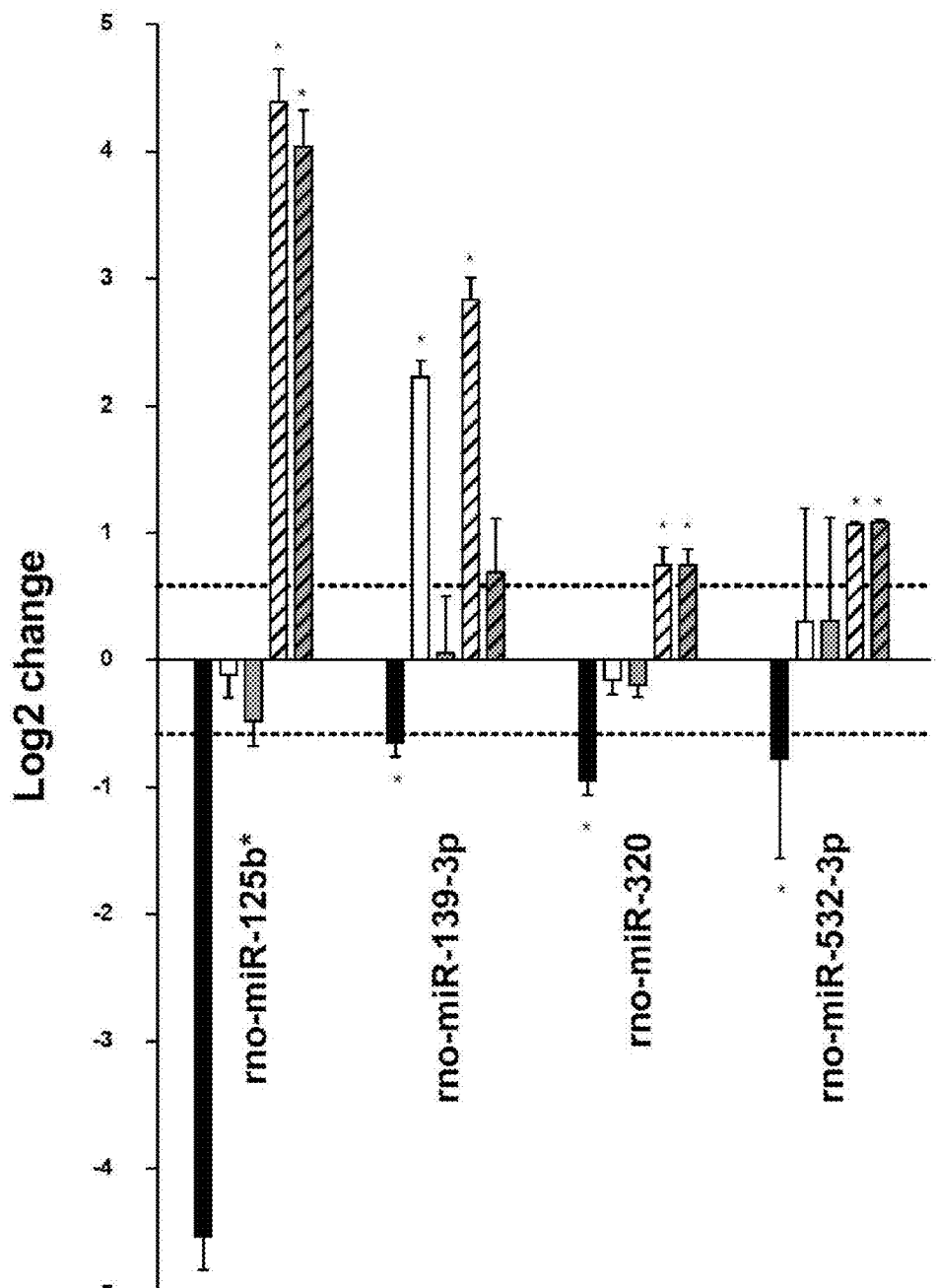

FIG. 8 MiRNAs involved in Cardioprotection by Both Preconditioning- and Postconditioning-Induced Mechanisms Panel A shows miRNA-188 the expression of which was significantly increased both in preconditioning and postconditioning as compared to non-ischemic controls and this alteration remained if compared with changes in ischemia-reperfusion, Panel B shows miRNAs (miR-125b*, miR-139-3p, miR-320 and miR-532-3p) that were significantly changed by ischemia-reperfusion as compared to non-ischemic controls, however, both preconditioning and postconditioning significantly reversed their expression changes due to ischemia-reperfusion.

These results show that these miRNAs are involved in cardioprotection both in pre- or postconditioning. In case of miRNAs shown on panel B cardioprotection occurs via a reversal of the deleterious mechanisms of ischemia-reperfusion. Whereas in case of miRNA-188 shown on Panel A the induction of this microRNA results in cardioprotection.

Bars show alterations in miRNA expression in ischemia-reperfusion vs. non-ischemic control (IR/C, black bars); preconditioning vs. non-ischemic control (PRE/C, white bars); postconditioning vs. non-ischemic control (POST/C, grey bars) or to preconditioning vs. ischemia-reperfusion (PRE/IR, white hatched bars); postconditioning vs. ischemia-reperfusion (POST/IR, grey hatched bars). Values are log 2 of fold expression changes±standard deviation. * represents p<0.05 and a log 2 fold change of <−0.585 or >0.585.

Figure 9:
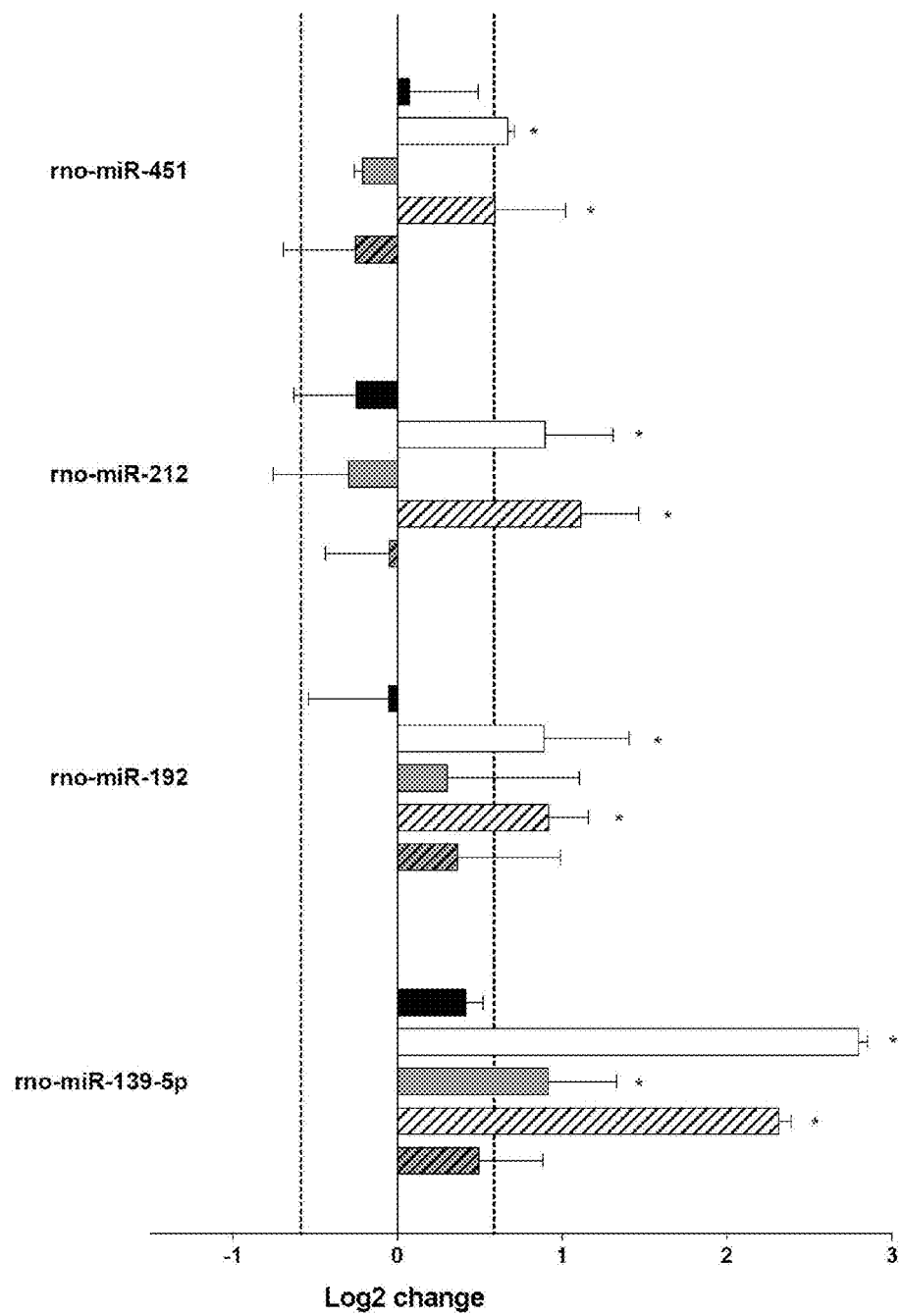
Figure 9:
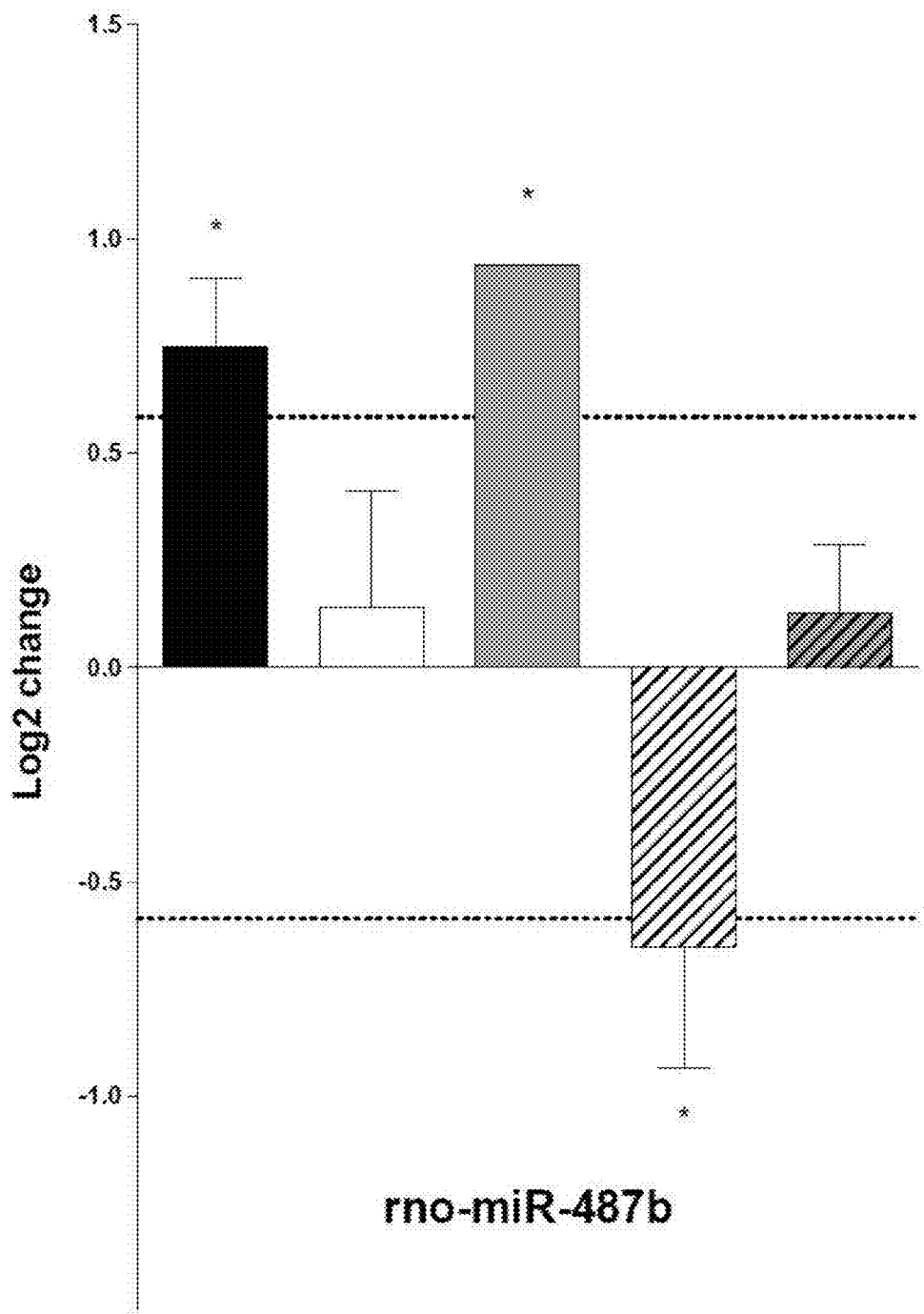

FIG. 9 MiRNAs involved in Cardioprotection On the Basis of Preconditioning-Induced Mechanisms This graph shows miRNAs that were significantly altered by preconditioning as compared both to ischemia-reperfusion and to non-ischemic controls, demonstrating that these miRNAs are specifically induced by preconditioning and have a role in cardioprotective adaptation (can be termed as Protectomirs). Thus, these miRNA have a cardioprotective effect by a mechanism also activated in preconditioning. Panel A shows miRNAs the expression of which did not change significantly in ischemia reperfusion in comparison with the control, however, pre-conditioning significantly elevated their level, typically both in comparison with the control and with the ischemic sample. Panel B shows miR-487b which experiences a significantly elevated level in ischemia reperfusion whereas its expression is reversed in preconditioning indicating its cytotoxic feature.

Bars show alterations in miRNA expression in ischemia-reperfusion vs. non-ischemic control (IR/C, black bars); preconditioning vs. non-ischemic control (PRE/C, white bars); postconditioning vs. non-ischemic control (POST/C, grey bars) or to preconditioning vs. ischemia-reperfusion (PRE/IR, white hatched bars); postconditioning vs. ischemia-reperfusion (POST/IR, grey hatched bars). Values are log 2 of fold expression changes±standard deviation. * represents p<0.05 and a log 2 fold change of <−0.585 or >0.585.

Figure 10:
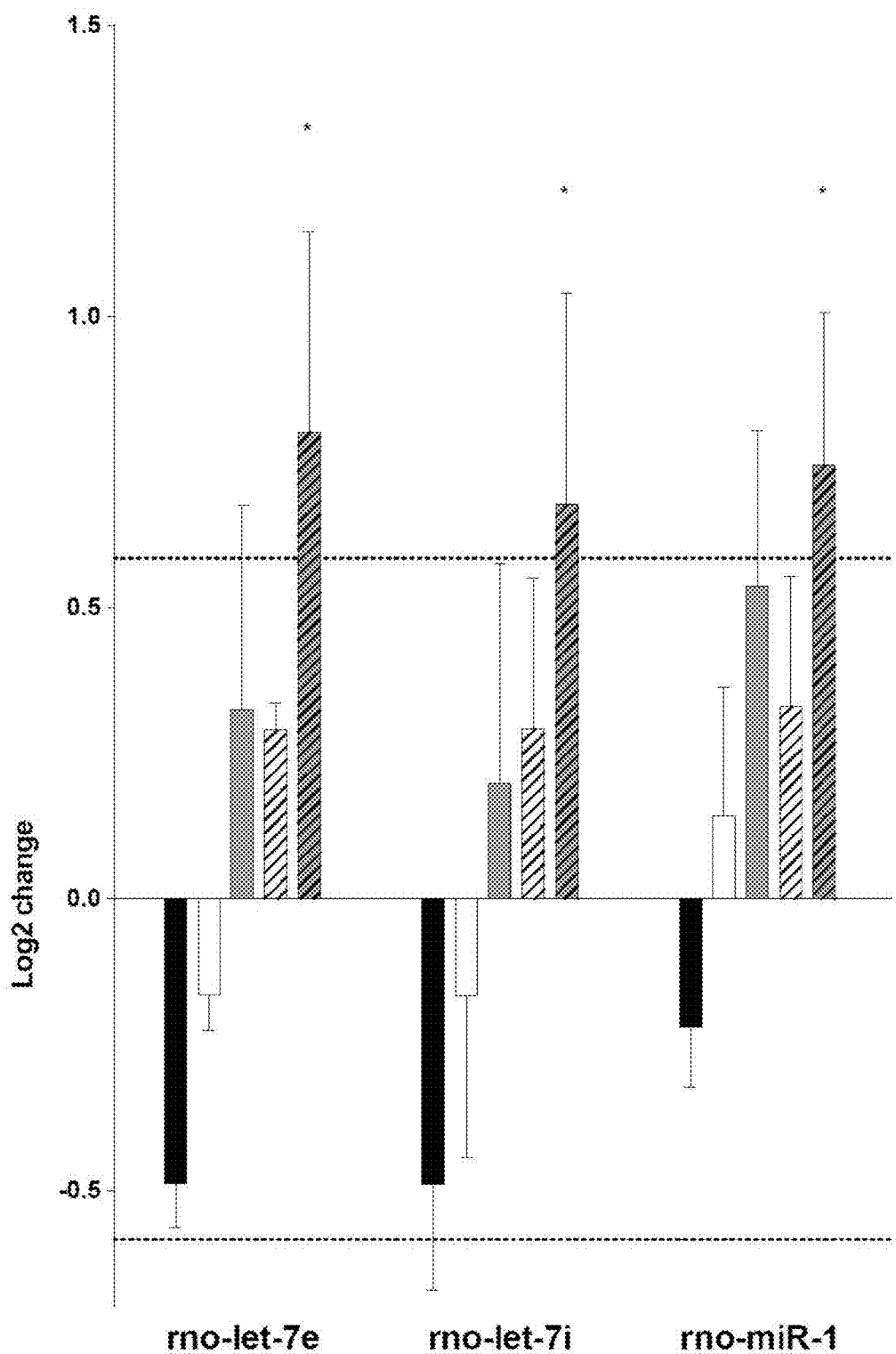
Figure 10:
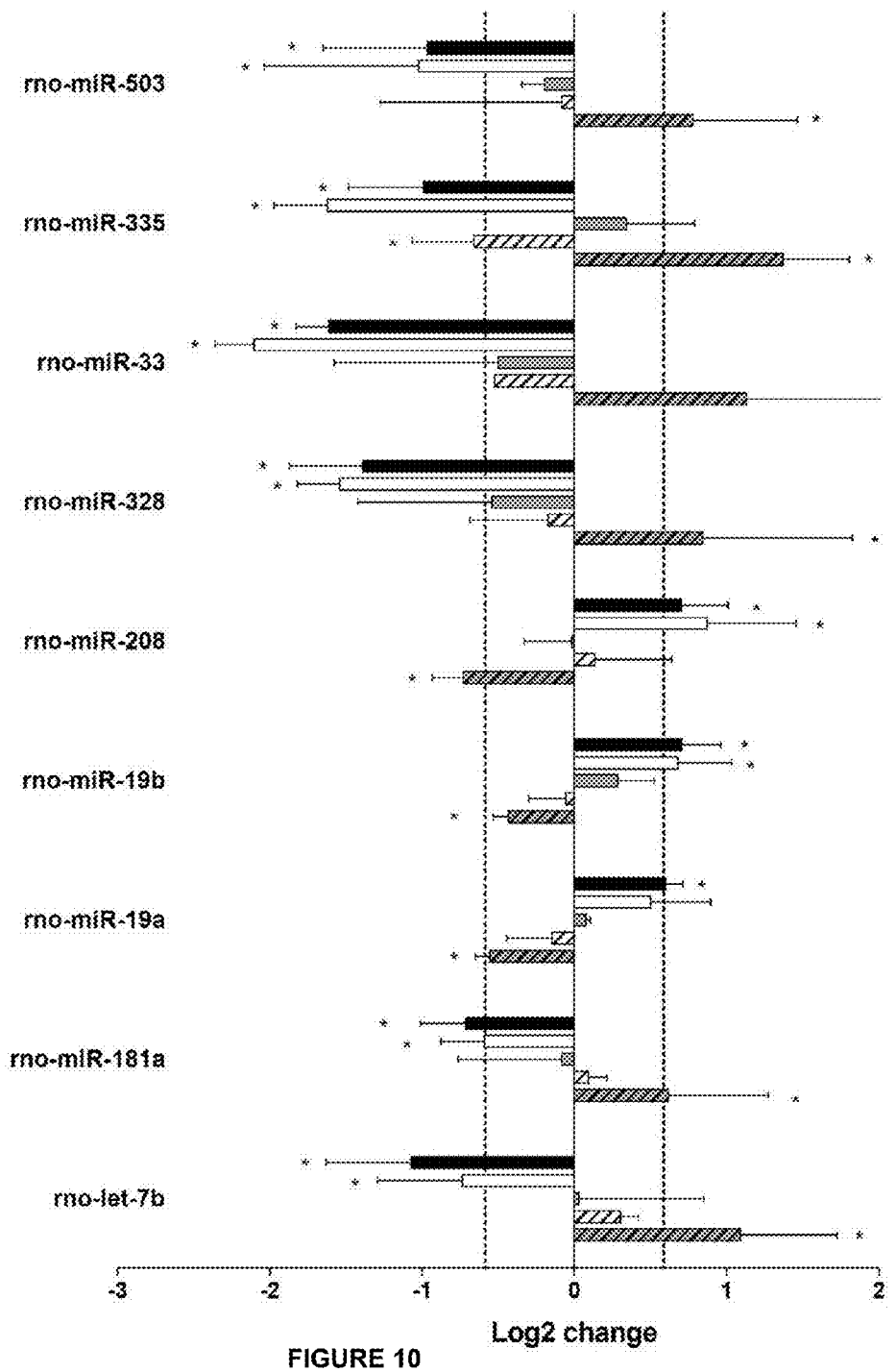

FIG. 10 MiRNAs involved in Cardioprotection On the Basis of Postconditioning-Induced Mechanisms (Panels A and B)

This graph shows miRNAs that were significantly altered by postconditioning as compared to ischemia-reperfusion, demonstrating that these miRNAs are specifically altered by postconditioning. Certain miRNAs, like miR-208, miR-19b and miR-19a have to be down-regulated so that a postconditioning-induced cardioprotection may occur and therefore the microRNAs themselves can be termed as Pathomirs, i.e. cytotoxic miRNAs (they are also significantly up-regulated in ischemia/reperfusion). Thus, cardioprotection may be available via inhibitors against these miRNAs.

Let-7e, let-7i, miR-1, let-7b, miR-181a, miR-328, miR-33, miR-503 are "Protectomirs" as they are significantly up-regulated due to ischemic postconditioning.

Bars show alterations in miRNA expression in ischemia-reperfusion vs. non-ischemic control (IR/C, black bars); preconditioning vs. non-ischemic control (PRE/C, white bars); postconditioning vs. non-ischemic control (POST/C, grey bars) or to preconditioning vs. ischemia-reperfusion (PRE/IR, white hatched bars); postconditioning vs. ischemia-reperfusion (POST/IR, grey hatched bars). Values are log 2 fold expression changes±standard deviation. * represents $p<0.05$ and a log 2 fold change of $<-0.585$ or $>0.585$.

Figure 11:
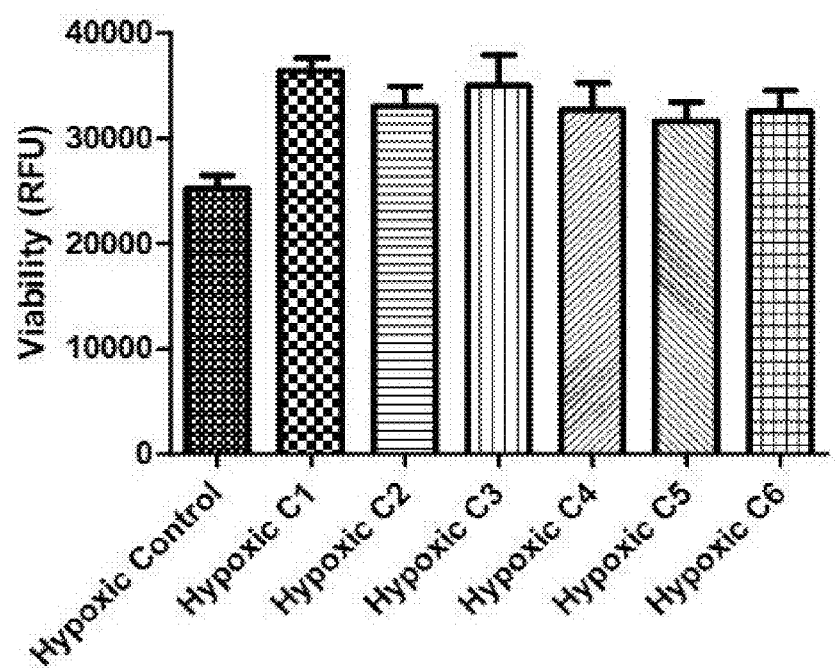

FIG. 11. This figure shows cytoprotection against simulated ischemia by randomly selected combinations of the randomly selected cardioprotective microRNAs and/or inhibitors of cytopathic microRNAs (see Table 3b) in cell viability tests. The applied combinations were all effective against simulated ischemia/reperfusion injury.

DETAILED DESCRIPTION OF THE INVENTION

Recently the heart has been shown to possess a remarkable ability to adapt to ischemia-reperfusion stress and this molecular plasticity of the heart in ischemia-reperfusion has been the focus of intense research in the hope that the underlying mechanisms may be amenable to therapeutic exploitation. Ischemic preconditioning is a well-described adaptive response in which brief exposure to ischemia markedly enhances the ability of the heart to withstand a subsequent ischemic injury. Moreover, brief cycles of ischemia-reperfusion applied following a longer period of ischemia also confer cardioprotection against the consequences of myocardial ischemia-reperfusion, a phenomenon called ischemic postconditioning.

The discovery of these two major forms of endogenous anti-ischemic, cardioprotective mechanisms has encouraged the exploration of new ways to protect the ischemic and/or reperfused myocardium and has amplified our knowledge of the molecular basis of injury and survival during ischemia and/or subsequent reperfusion [Ferdinandy P et al. 2007]. It is important to note that both pre- and postconditioning can be induced in several reversible stress stimuli, such as e.g. hypoxia, specific drugs mimicking the protective effect of either pre- or postconditioning, and also by remote conditioning i.e. stress stimuli of other than the target organ [Ferdinandy P et al. 2007].

Cardioprotective interventions, mimicking these innate adaptation protective mechanisms, especially ischemic postconditioning has emerged as a theoretically possible, clinically applicable approach for limiting myocardial injury in humans [Ovize M et al. 2010]. However, despite of intensive research in the last decades, the exact biological mechanisms underlying the cardioprotective effect of pre- and postconditioning remained unclear due to the complexity of the cellular events and the interference of other co-morbidities and risk factors of ischemic heart diseases [Ferdinandy P et al. 2007]. Therefore, the use of systems biological approaches seems necessary to reveal the complex molecular events.

Ischemia and therefore acute ischemic and/or reperfusion injury is not limited to the heart, and analogous adaptive and protective mechanisms should work in stroke, ischemia of kidneys, the liver and other organs.

However, it is not obvious how to utilize or mimic these endogenous mechanisms in the prevention or treatment of ischemia-reperfusion injury as evidently a surgical intervention for that purpose is undesired in most cases and would present additional risk for a patient possibly in critical state. Instead of pre- or post-conditioning effected by a surgical intervention administration of specific therapeutic agents having the same effect would be desired, however, not only such compounds but the underlying regulatory mechanism are largely unknown.

In the herein disclosed series of studies illustrating the present invention, the present Inventors aimed at identifying miRNAs related to ischemia and/or reperfusion injury and to preconditioning or postconditioning using a systematic comparison of the miRNA expression patterns.

In the prior art, even if miRNA regulation in ischemia was studied expression levels were compared typically with a non-ischemic control.

As a novel approach, the inventors used expression patterns of miRNAs in the test ischemic (and reperfused) sample and samples subjected to tissue or cytoprotective treatment (pre- and/or postconditioning), and obtained data by comparison of these expression patterns not only with a non-ischemic control but also by comparing the expression levels in the pre- and/or postconditioned samples to the levels under ischemia-reperfusion treatment.

In their experimental design, to study expression patterns in the various samples the present inventors used both miRNA microarray and RT-PCR, so that by the latter method the microarray data could be evaluated. The relevant microarray data are shown in the figures and the RT-PCR data in Tables below in the Examples. It will be understood by a skilled person that as new miRNAs are continuously identified in the art, by repeating Inventors' experiments on a larger miRNA set or using the same principles further miRNA species regulated analogously to those found by the present Inventors shall be found later.

There is a standard nomenclature system for miRNAs [Griffiths-Jones S, 2006] which is used in the present description, too. Based on these nomenclature sequences of miRNA, together with further data, can be unambiguously found in the miRBase database (earlier Sanger database). Names are assigned to experimentally confirmed miRNAs before publication of their discovery. The name comprises a prefix "mir" or "miR" wherein "mir-" refers to the unmatured pre-miRNA, while a capitalized "miR-" refers to the mature form. The number in the name normally indicates the order of naming, i.e. usually the order of discovery. Related miRNA sequences which differ only in one or two nucleotides are annotated with an additional lower case letter. For example, miR-19a would be closely related to miR-19b. Pre-miRNAs that lead to 100% identical mature miRNAs but that are located at different places in the genome are indicated with an additional dash-number suffix. For example, the pre-miRNAs hsa-mir-194-1 and hsa-mir-194-2 lead to an identical mature miRNA (hsa-miR-194) but are located in different regions of the genome. Species of origin is designated with a three-letter prefix, e.g., hasa stands for human (*Homo sapiens*) and mo for *Rattus norvegicus*. When two mature miRNAs originate from opposite arms of the same pre-miRNA, they are denoted with a –3p or –5p suffix. When relative expression levels are known, an asterisk following the name indicates an miRNA expressed at low levels relative to the miRNA in the opposite arm of a hairpin. For example, miR-123 and miR-123* would share a pre-miRNA hairpin, but more miR-123 would be found in the cell.

Quite surprisingly the present inventors have recognized that an appropriate comparison of the miRNA expression patterns in samples exposed to ischemia and a subsequent reperfusion, preconditioning and a subsequent ischemia-reperfusion as well as ischemia-reperfusion and a subsequent postconditioning protocol leads to the identification of miRNA species differently regulated in these conditions and being useful to prepare cardioprotective miRNA compounds which are either agonists or antagonists of said miRNA species which are useful in the treatment of a patient predisposed to or affected by heart ischemia, eg. acute myocardial infarction, wherein cells, tissues and/or organs are protected against short term and/or direct consequences of acute ischemic and reperfusion injury in, in the heart of said patient. Preferably, it has been found that said miRNA compounds are to be administered to the patient within 5, 4, 3, 2 or 1.5 hours after the ischemic attack or simultaneously with reperfusion and/or less than one day or less than 12, 8, 6, 5, 4, 3, 2 or 1 hour(s) before surgery or intervention associated with a risk of ischemia.

Even more so, it has been surprisingly found that miRNAs significantly up-regulated in pre- and/or postconditioning as compared to a tissue exposed to ischemia-reperfusion without these protective mechanisms, have cytoprotective effect. Similarly, down-regulation of miRNA species in pre- and/or postconditioning allows cytoprotective mechanism to occur under these conditions; thus these miRNA shall advisably be antagonized so as to induce cytoprotection. It has been found that antagonists of these miRNAs have a cytoprotective effect, too.

Specifically, by using miRNA microarrays of 350 known rat miRNA genes, several miRNAs involved in the early phase of myocardial ischemia-reperfusion injury and in cardioprotection by ischemic pre- and postconditioning has been identified and cardioprotective miRNA compounds, i.e. miRNA mimics (rno-miR-139, rno-miR-125b*, rno-miR-33) and miRNA inhibitors (rno-miR-494, rno-miR-487b) have been prepared.

More closely, according to the invention a set of samples are provided, comprising a control sample, a first sample and a second sample and/or a third sample, each of the samples are exposed to aerobic perfusion for a time-period, and within this time period
- the control sample is exposed neither to ischemia-reperfusion nor to preconditioning nor to postconditioning thereby obtaining a non-ischemic control sample, and
- exposing the first sample to at least ischemia thereby obtaining an ischemic sample, and
- preconditioning the second sample by exposing it to a preconditioning protocol and then at least to ischemia thereby obtaining a preconditioned sample, and/or
- postconditioning the third sample by exposing it at least to ischemia and to a postconditioning protocol thereby obtaining a postconditioned sample.

Samples subjected to ischemia typically are exposed to reperfusion thereafter so as to obtain an ischemic-reperfused sample. This is particularly so in case of postconditioning.

Thereafter measurement is performed to experimentally determine the expression levels of miRNA species, preferably a multiplicity thereof is.

Preferably, at least one of the following data set is obtained:
i) expression level of miRNA species
in the ischemic/reperfused sample as compared to the non-ischemic control sample
in the preconditioned sample as compared to the non-ischemic control sample and
in the preconditioned sample as compared to the ischemic/reperfused sample,
and/or
ii) expression level of miRNA species
in the ischemic/reperfused sample as compared to the non-ischemic control sample
in the postconditioned sample as compared to the non-ischemic control sample, and
in the postconditioned sample relative to the ischemic/reperfused sample.

In a preferred embodiment the following data set is obtained: expression level of miRNA species
in the ischemic/reperfused sample as compared to the non-ischemic control sample
in the preconditioned sample as compared to the non-ischemic control sample and
in the postconditioned sample as compared to the non-ischemic control sample, and
in the preconditioned sample as compared to the ischemic/reperfused sample,
in the postconditioned sample relative to the ischemic/reperfused sample.

At least expression level of miRNA species
in the preconditioned sample as compared to the ischemic/reperfused sample, and/or
in the postconditioned sample relative to the ischemic/reperfused sample is calculated from the other respective data sets which are assessed by direct measurement.

In a preferred embodiment raw data on expression levels of said miRNA species are obtained
in the non-ischemic control sample
in the ischemic/reperfused sample and
in the preconditioned sample and/or
in the postconditioned sample
the ratio of the expression levels of said miRNA species is calculated
in the ischemic sample relative to non-ischemic control sample
in the preconditioned sample relative to non-ischemic control sample
in the postconditioned sample relative to non-ischemic control sample
in the preconditioned sample relative to the ischemic/reperfused sample and/or
in the postconditioned sample relative to the ischemic/reperfused sample.

Based on these assessments and calculations the following two basic types of miRNA species can be identified:
Protectomir:
a miRNA species, termed a pre-ischemic cytoprotective miRNA species, provided that the miRNA species is significantly up-regulated in the preconditioned sample relative to the ischemic/reperfused sample
a miRNA species, termed a post-ischemic cytoprotective miRNA species, provided that the miRNA species is up-regulated in the postconditioned sample relative to the ischemic/reperfused sample
Pathomir:
a miRNA species, termed a pre-ischemic cytopathic miRNA, provided that the miRNA species is down-regulated in the preconditioned sample relative to the ischemic/reperfused sample
a miRNA species, termed a post-ischemic cytopathic miRNA species, provided that the miRNA species is down-regulated in the postconditioned sample relative to the ischemic/reperfused sample.
Toxicomir:
Cytopathic miRNAs are termed cytotoxic if they are significantly up-regulated in the ischemic sample as compared to the non-ischemic control and if they are down-regulated either by preconditioning and/or postconditioning indicating that they have a harmful effect in ischemia. These miRNAs may be called Toxicomirs.

It is understood herein that a miRNA species may belong to multiple categories at the same time but there are categories which exclude each other.

For example, an agonist designed against a miRNA species which is simultaneously a pre-ischemic cytoprotective miRNA species and a post-ischemic cytoprotective miRNA species and vica versa, is preferred.

For example, an antagonist designed against a miRNA species which is simultaneously a pre-ischemic cytotoxic miRNA species and a post-ischemic cytotoxic miRNA species and vica versa, is preferred.

The situation that a pre-ischemic cytotoxic miRNA species is at the same time a pre-ischemic cytoprotective miRNA species is obviously impossible and excluded, and the same is true for post-ischemic miRNA species.

In rare events it was found that a pre-ischemic cytotoxic miRNA species is simultaneously a post-ischemic cytoprotective miRNA species and a pre-ischemic cytoprotective miRNA species is simultaneously a post-ischemic cytotoxic miRNA species, which reflects the fact that the adaptive protective gene regulation mechanism in preconditioning and in postconditioning might be different. Thus, the patient conditions before a predisposed ischemia and after an ischemic attack is to be carefully assessed and handled or treated differently and specifically.

The question of which type of miRNA compound is to be administered to a patient depends on patient status or condition. Thus, assessment of patient status may provide a valuable information on the treatment to be applied so as to improve protection of patient tissue against an acute ischemia-reperfusion injury.

Specifically, if assessment of patient status indicates that said patient is vulnerable to a prospective ischemic attack or there is a lack of indication of any inherent protection in a patient against such an attack, this provides an information to the medical personnel that an intervention is advisable.

Typically, an antagonist of a pre-ischemic cytopathic miRNA (i.e. the antagonist of a Pathomir) or an agonist of a pre-ischemic cytoprotective miRNA (i.e. of a Protectomir) is to be added to a patient which is predisposed to ischemia. In this case one or more tissues or organs of the patient are endangered by an ischemic affect. The ischemic event may or may not be predictable. If a therapeutic intervention which involves a step causing ischemia, including hypoxia of certain tissues is scheduled, the timing of the expectable ischemic affect can be determined in advance and the appropriate Protectomir administered in due time before the possible ischemic event.

However, in a case when the occurrence of ischemia, including hypoxia of a tissue is due to the disease status of the patient the time of said occurrence cannot be predicted. In this case assessing or monitoring of the patient's status is of importance. In this aspect, risk factors for myocardial infarction, preferably the acute variant thereof should be considered. If the patient is at significant risk of ischemia, an appropriate Protectomir or a cocktail or combination of Protectomirs should be added to her/him. By doing so a similar condition can probably be achieved in the endangered tissue as by preconditioning providing a safe, pharmacological and patient-friendly treatment option. The expectably better patient compliance underlines the importance of this kind of treatment.

The methodology of risk factor assessment has been significantly improved in later years.

Risk factors for atherosclerosis are generally risk factors both for myocardial infarction and infarction of other organs (brain, kidney, lower and upper limbs, retina, etc). Such risk factors are for example:

Diabetes (with or without insulin resistance)—the single most important risk factor for ischaemic heart disease (IHD);

Tobacco smoking;

Hypercholesterolemia or elevated blood cholesterol level (more accurately hyperlipoproteinemia, especially high low density lipoprotein and low high density lipoprotein level);

High Triglyceride level;

High blood pressure;

Family history of ischaemic heart disease (IHD);

Obesity (defined by a body mass index of more than 30 $kg/m^2$, or alternatively by waist circumference or waist-hip ratio);

Age—Men acquire an independent risk factor at age 45, Women acquire an independent risk factor at age 55; in addition individuals acquire another independent risk factor if they have a first-degree male relative (brother, father) who suffered a coronary vascular event at or before age 55; Another independent risk factor is acquired if one has a first-degree female relative (mother, sister) who suffered a coronary vascular event at age 65 or younger;

Hyperhomocysteinemia (high homocysteine level in the blood, a toxic blood amino acid that is elevated when e.g. intakes of vitamins B2, B6, B12 and folic acid are insufficient);

Stress—Occupations with high stress index are known to have susceptibility for atherosclerosis and consequently to ischemic diseases;

Alcohol—Studies show that prolonged exposure to high quantities of alcohol can increase the risk of heart attack;

Males are more at risk than females.

Many of these risk factors are modifiable, so many heart attacks can be prevented by maintaining a healthier lifestyle. The individuals susceptibility to develop myocardial infarction can be predicted e.g. by using the SCORE table [Conroy R M et al. 2003; www.heartscore.org], prepared by the European Society of Cardiology.

Patients with high risk or possibly even at medium risk of cardiovascular disease or ischemic heart disease advisably should seek medical advice and a treatment by Protectomirs (Protectomir therapy) should be considered. Preferably, a patient with a high risk of death due to an ischemic attack or acute myocardial infarction should be contemplated. A possible indication is a CVD (cardiovascular disease) score of higher than 3%, more preferably higher than 5%, 7%, 10%, 15% or 20% [Conroy R M et al., 2003]. Other risk assessment methods are also applicable.

In an other embodiment of the invention an antagonist of a post-ischemic cytopathic miRNA (i.e. the antagonist of a Pathomir) or an agonist of a post-ischemic cytoprotective miRNA (i.e. of a Protectomir) is to be added to a patient who experience to ischemia, preferably acute ischemia and possibly a subsequent reperfusion.

In this case it may be crucial that the patient may receive an appropriate treatment, possibly including administration of the cytoprotective miRNA compounds (including Protectomirs) to the patient, as soon as possible after the ischemic event or, if occurs, during or soon after reperfusion.

A quick assessment of patient status after hospitalization is also important. If necessary, a surgical intervention (e.g. PCI) may be necessary so as to achieve reperfusion or a reperfusion therapy is to be applied.

According to a recently published ESC/EACTS Guidelines [Wijns W et al. 2010] essentially the following advice is given in respect of reperfusion strategies in revascularization.

It is essential to make every effort to minimize all time delays, especially within the first 2 h after onset of symptoms. Patients admitted to hospitals without PCI facilities should be transferred to a PCI-capable center and no fibrinolytics should be administered if the expected time delay between first medical contact (FMC) and balloon inflation is less than 2 h. If the expected delay is more than 2 h (or more than 90 min in certain patients more than 75 years old), patients admitted to a non-PCI center should immediately receive fibrinolysis and then be transferred to a PCI-capable center where angiography and PCI should be performed in a time window of 3-24 h.

Delayed PCI may be performed up to 60 h or 3 days from symptom onset. For example, this may be necessary after an unsuccessful fibrinolysis or if the first medical contact occurs lately, e.g. later than 12 or 24 hours after symptom onset. The authors found, however, that patients presenting between 3 and 28 days with persistent coronary artery occlusion, did not benefit from PCI.

It is noted that no time limit should be set between onset of symptoms and invasive diagnosis and re-vascularization in patients with cardiogenic shock.

It has been found that primary PCI (i.e. PCI without fibrinolytic therapy) within 6-12 h after symptom onset treated in high-volume, experienced centers have shown more effective restoration of vessel patency, less re-occlusion, improved residual LV function, and better clinical outcome than with in-hospital fibrinolytic therapy under comparable conditions.

Before PCI, the administration of an antagonist of a pre-ischemic cytopathic miRNA compound and/or of the agonist of a pre-ischemic cytoprotective miRNA compound should have the effect of providing protection during surgery and a possible ischemic attack, or during a spontaneous (further) ischemic-reperfusion injury.

An antagonist of the post-ischemic cytopathic miRNA and/or agonist of a post-ischemic cytoprotective miRNA should be applied before, during and immediately after the therapeutic intervention. The rationale is that preferably said compound should be present when reperfusion occurs or soon thereafter to fortify or provide the affect of a post-conditioning.

The time-frame of administration of these miRNA are outlined above and depends on the intervention applied.

It may be advisable, nevertheless, to administer these miRNA compounds thereafter, too, so as to prevent or diminish long-term effect of ischemic.

Whether the miRNA species have the effect sought is tested whether they are significantly up- or down-regulated in the sample at issue as compared to either the non-ischemic control or as compared to an other sample. Significantly up-regulated or down-regulated is understood herein as up-regulated or down-regulated, respectively, as compared to the expression level in an other sample used as a reference, by at least 1.3 fold, preferably by at least 1.5 fold, more preferably by at least 1.8 fold, in a statistically significant setting, wherein the p value is less than a significance level of 0.1, preferably of 0.05 or of 0.01.

It is to be mentioned that this level of significance, in particular the 1.5 fold level, pertains to the present sensitivity of assays and especially the miRNA microarray method. The skilled person will understand that this may change if a more sensitive method is applied. Furthermore, sensitivity of methods for assessing expression levels could and probably would increase in the future as it happened in the past. Therefore, further miRNAs may be found as significantly up- or down-regulated without departing the inventive concept. A 1.3 fold change in the expression level is a realistic threshold even in the case of a more sensitive method.

It has been found in the art both by experimental and bioinformatics methods that target sites of miRNA on the mRNA are predominantly determined by the 6 or 7 nucleotides "seed" region at the 5' end of the miRNA, i.e. nucleotide positions 2 to 7, 3 to 9, 3 to 8 or 2 to 8 of the mature miRNA. An additional region to determine target site ("3'-compensatory site") is found at the 3' part of the miRNAs, typically at or within positions 13 to 18 [Robertson B., 2010; Small E M 2010]. These two sites define miRNA families of the same or related target sites and consequently target genes. Based on identical seed region and target sites miRNAs are grouped into families which are likely to target identical or similar sets of target genes. Moreover, miRNA target genes can now be predicted by several methods [Griffiths-Jones, S., et al. 2006].

It is also found by several authors that members of miRNA families are regulated similarly in cardiac diseases [Olson E. and Van Rooij, E. WO2009/062169 2009; Olson Eric N.; Rooij Eva Van; Quiat Daniel WO2011/084460 2011]. Results of the present Inventors confirm this finding in several cases.

The finding that a whole miRNA family can be specifically silenced by seed-targeting with tiny locked nucleic acids as long as 8 nucleotides, further supports this concept [Obad S. et al., 2011].

Once a miRNA species is identified with a given expression pattern in ischemic-reperfusion and in preconditioning and/or postconditioning thereto, and it is categorized according to the present invention as explained above. It is thus plausible that other members of the same family will bind to the same target sites and will regulate the same or similar pattern of genes. In fact it has been found by the present inventors that miRNAs belonging to the same family show a similar expression regulation pattern in the samples (i.e. conditions) according to the invention (see in this regard the let-7 family, miR-19a and 19b, miR-139-3p and 139-5p, miR-10a-5p and miR-10b). Taken the fact of increasing number of miRNAs in the miRBase database, it is within the skills of a skilled person to find further family members of a miRNA categorized according to the present inventive solution for identifying and preparing miRNA by the method of the present invention. It may happen that one or more family member has not exactly the same function or effect; however, this can be easily decide by a functional test disclosed herein, either by the cell viability test of Example 3 or by the method for identifying relevant miRNAs using the ischemic/reperfused, the preconditioned and the postconditioned samples.

The number of sequenced and characterized miRNAs has been exponentially increased in the past 5 to 10 years, miRNA sequences are stored at present in the miRBase database which is the primary database for all miRNAs sequenced. The number of cytoprotective and cytotoxic miRNAs found by the present inventors on a relatively small set of miRNAs clearly shows that by repeating the method of the inventors further useful miRNAs will be identified. Once such a miRNA species is identified it is well within the skills of a person skilled in the art to prepare a miRNA agonist (e.g. a miRNA mimic) or a miRNA antagonist (e.g. antagomir) therefrom. Thus, it is clearly foreseen that based on the present invention it is well within the skills of a skilled person to prepare further miRNA compounds once the database increases, and preparation of such compounds is duly enabled herein.

Preparation of miRNA mimics and miRNA inhibitors are within the skills of a person skilled in the art. Based on the sequence one can order mimics and inhibitors from commercial sources. For example, the miRIDIAN miRNA mimics and hairpin inhibitors can be ordered from Dharmacon, a subsidiary of Thermo Fisher Scientific Inc. The miScript miRNA Mimics of Quiagen are synthetic, double-stranded RNAs which mimic naturally occurring miRNAs after transfection into cells. Quiagen also markets miScript miRNA Inhibitors, which are synthetic, single-stranded, chemically modified RNAs which specifically inhibit miRNA function after transfection into cells. Mimics and inhibitors can be transfected into the cells, followed by downstream gene expression analysis or phenotypic analysis, is performed to elucidate the targets and roles of particular miRNAs.

Sigma-Aldrich offers MISSION® Human miRNA Mimics which are small, double-stranded RNA molecules, and mimic endogenous mature miRNA molecules when transfected into cells. Sidma-Aldrich offers at least 985 individual miRNA mimics from the shelf and typically ship within one day of purchase miRNA. As a service, custom target sequence design is also available.

Ambion's Anti-miR™ miRNA Inhibitors are chemically modified, single stranded nucleic acids designed to specifically bind to and inhibit endogenous miRNA (miRNA) molecules. They are available both in ready-to-use and in custom design format. Pre-miR™ miRNA Precursor Molecules, which are small, chemically modified double-stranded RNA molecules designed to mimic endogenous mature miRNAs are also readily available from Ambion.

Exiqon offers miRCURY LNA™ miRNA Inhibitor Libraries and claims to have at present the most comprehensive miRNA inhibitor library on the market. Scientific background behind the Locked Nucleic Acid (LNA) inhibitor technology is disclosed e.g. by Kauppinen S (2007).

It has been shown that inhibitors having a sequence complementary to mature miRNA can interact with the miRNA-RISC nucleoprotein complex has an inhibiting effect. Vermeulen et al (2007) teach that incorporation of highly structured, double-stranded flanking regions around the reverse complement core significantly increases inhibitor function and allows for multi-miRNA inhibition at subnanomolar concentration.

Principles behind preparation of these miRNA compounds are known in the art.

MiRNA inhibitors or mimics are typically stabilized, e.g. by phosphorotioate backbone modifications, against degradation in the organism. Moreover, a variety of nucleotide modifications, including 2'-O-methyl (2'-O-Me) and 2'-O-methoxyethyl (2'-MOE) derivatives have been used to enhance binding affinity and stability of miRNA compounds. Locked nucleic acids have a particularly strong binding; therefore even shorter sequences like seed sequences are sufficient to efficiently block miRNA species binding [Obad S., 2011]. Methods of chemical modification and design are reviewed by Lennox K A (2011).

Thus, based on a miRNA species identified in accordance with the invention a miRNA compound, either an agonist or antagonist thereof is readily available.

Methods for targeting the miRNA compound of the invention are also available in the art. In WO2010129672A1 lipophilic polynucleotide conjugates wherein the lipophilic group is conjugated through a phosphate ester or ether linkage are disclosed. In WO2006137941A2 the authors disclose methods to introduce synthetic miRNA mimics or inhibitors into the cells and conjugation of functional groups are disclosed. The synthetic RNA molecules are of 17-125 residues in length and comprise a region with a sequence identical to a partial mature miRNA sequence.

Administration of miRNA to the patient's target tissue can be effected several ways.

Traditionally, injecting miRNA compounds is the most acceptable method; however, this is preferably suitable to target the liver, kidney or the spleen.

Encapsulation of the miRNA compound into a lipid-based formulation e.g. a liposome or cardiac catheterization may be more appropriate to introduce miRNAs into the cardiovascular system [Small E M 2010].

The miRNA compounds can be introduced into the blood stream by drug eluting devices which are placed into the endangered or injured tissue or organ. Such devices are e.g. drug-eluting devices.

In certain embodiments topical administration is possible and the pharmaceutical composition can be formulated as an ointment, drops, solution, eye-drops, injunction or lotion, etc. This kind of administration may be a preferred option e.g. in peripheral vessel disease.

Inhibitors or agonists can be introduced into the appropriate tissue and expressed therein by an expression vector comprising a double stranded DNA comprising DNA complements of two repeats of an antisense miRNA (WO2009132351A2, CA2609142A1).

Vectors suitable for introducing sequences from which antagonists, e.g. antisense miRNAs can be expressed or miRNAs antagonizing the effect of others as well as miRNAs which are agonists of others, e.g. Protectomirs, are known in the art. Such vectors include but are not limited to viral vectors, eg. retrovirus, adenovirus, lentivirus, adeno-associated virus vectors, plasmids etc. Similarly, methods for introducing DNA or vectors are known in the art and include but are not limited to electroporation, lipofection or other known transfection method. In a preferred embodiment when targeting a given tissue cells are used as vehicles to carry said expressible genetic material to the tissue to be treated. These cells may target said tissue e.g. by a homing mechanism. Such cells can be eg. stem cells, or pluripotent or multipotent cell of said tissue.

Below the invention is further illustrated by non-limiting experimental examples. The skilled person will understand that equivalent solutions exist and are at his/her hand based on the more general teaching of the invention provided herein.

Experimental Protocols to Identify Tissue Protective miRNAs

Figure 1:
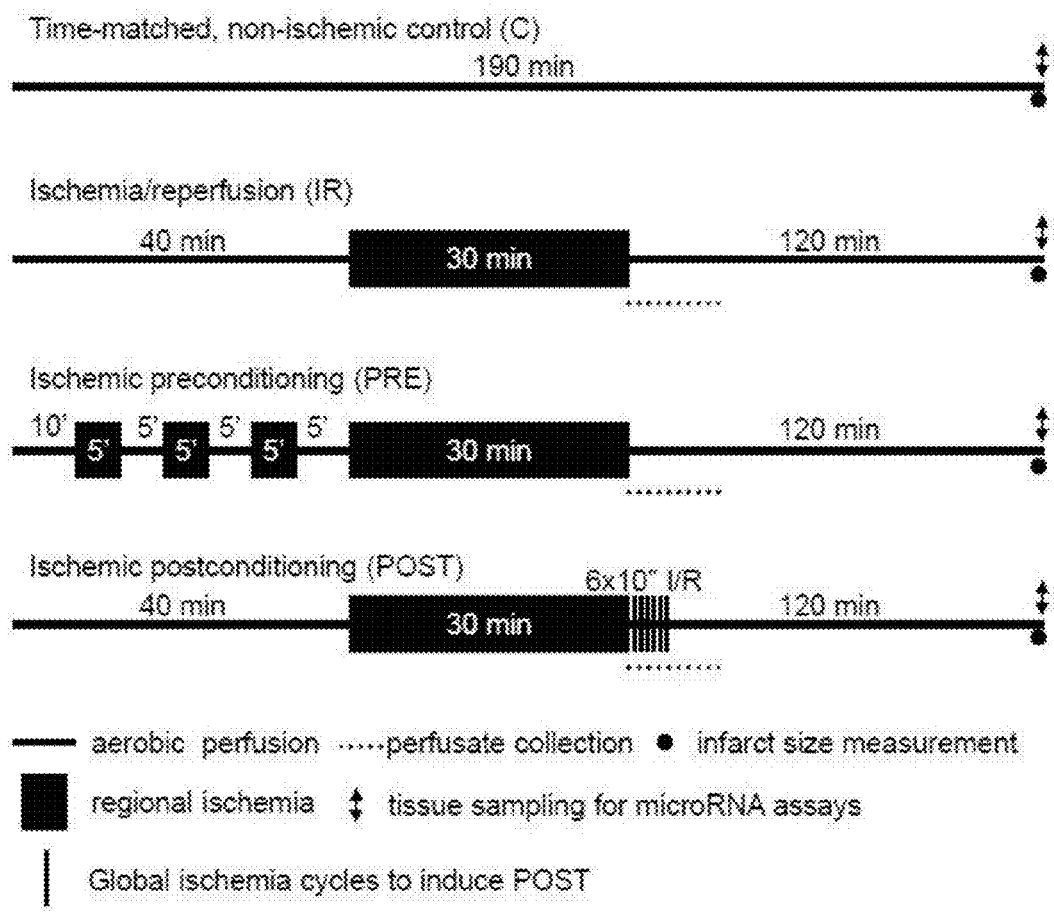
FIG. 1 Experimental Protocol

Male Wistar rats (250-300 g) were anesthetized and given 500 U/kg heparin intravenously. Hearts were then isolated and perfused according to Langendorff with an oxygenated, normothermic Krebs-Henseleit buffer as described [Csonka C et al. 1999]. Four different perfusion protocols were applied (FIG. 1). A time-matched control group was aerobically perfused for 190 min. In the second group regional ischemic was induced by 30 min left anterior descending coronary artery occlusion followed by 120 min reperfusion. In the third group, hearts were subjected to a preconditioning protocol followed by test ischemia-reperfusion. After 10 min equilibration, preconditioning was induced by three intermittent cycles of 5 min regional ischemia, separated by 5 min aerobic perfusion. In the fourth group postconditioning was induced by six consecutive cycles of 10 s coronary occlusion and 10 s reperfusion applied immediately at the onset of reperfusion. Heart rate and coronary flow were monitored throughout the perfusion protocol in all groups (FIG. 1). In order to assess the severity of tissue injury, infarct size was determined by triphenyltetrazolium chloride staining at the end of reperfusion (n=8-10), and evaluated by planimetry (Infarctsize 2.4; Pharmahungary, Szeged, Hungary). Infarct size was expressed as percentage of area at risk [Csonka C et al. 2010]. To further assess tissue injury, lactate dehydrogenase (LDH) release of hearts was measured using a LDH-P kit (Diagnosticum, Budapest, Hungary) from coronary effluents collected for 5 min upon reperfusion after test ischemia (n=12). LDH release was expressed as milliunits per minute per gram wet heart weight.

To confirm the cardioprotective effect of preconditioning and postconditioning, infarct size was measured after 30 minutes regional ischemia followed by 120 minutes of reperfusion. Both ischemic preconditioning and ischemic postconditioning significantly decreased infarct size as compared with hearts from the ischemia-reperfusion group (Table 1). LDH release was measured in the coronary effluent to further confirm the development of ischemic injury. Thirty minutes test ischemia followed by 5-min reperfusion resulted in a marked LDH release in the ischemia-reperfusion group (Table 1), that was significantly reduced both in the ischemic preconditioning and in the ischemic postconditioning groups (Table 1). Neither heart rate nor coronary flow was affected significantly by any of the interventions at the end of the perfusions (Table 1).

In separate experiments, at the end of the 120 min reperfusion myocardial samples of the anterior wall from all groups (n=6 in each group) were rapidly frozen in liquid nitrogen for miRNA isolation. After disruption of 6 heart samples in each group in liquid nitrogen, the sample was dissolved in a 20% Binding Buffer prepared from 80 µl of Binding Buffer and 320 µl of nuclease free water. All the other steps were done according to the Isolation of miRNA from Tissue protocol of the kit (Roche, Germany). RNA was eluted from the second column by adding 100 µl Elution Buffer. The quality and quantity was assessed spectrophotometrically (Nanodrop, USA) and with 2100 Bioanalyzer (Agilent, Calif., USA). Random pairs of the RNA extracted from the 6 different samples in each group were pooled, and the obtained 3 samples/group were assayed on the microarrays.

Microarray Analysis of MiRNA Expression and its Validation by QRT-PCR

A total of 50 ng purified miRNA was labeled using Agilent's miRNA Complete Labeling and Hyb kit system (Agilent Technologies Palo Alto, Calif., USA, p/n 5190-0456). The protocol was briefly the following: 25-25 ng of two parallel samples were pooled together in a final volume of 2 µl and subjected to a dephosphorylation reaction using Calf Intestinal Alkaline Phosphatase (CIP) at 37° C. for 30 minutes in the final volume of 4 In the second step, 2.8 µl of DMSO was added to each sample for denaturation at 100° C. for 5 minutes and placed on ice immediately. Following this step, a ligation reaction was carried out using T4 RNA Ligase and Cyanine3-pCp in a total volume of 11.3 µl for 2 hours at 16° C. to label the RNA samples. The labeled samples were completely vacuum dried on medium-high (45° C.) heat setting and hybridized onto the surface of Agilent 8×15k Rat miRNA Microarray (Agilent Technologies, Palo Alto, Calif., USA p/n G4473A). The microarray contained probes for the following 350 miRNAs from the Sanger database v 10.1. (miRBase recently maintained in the Faculty of Life Sciences at the University of Manchester with funding from the BBSRC, and was previously hosted and supported by the Wellcome Trust Sanger Institute.):

| | | | | | |
|---|---|---|---|---|---|
| rno-let-7a | rno-let-7b | rno-let-7b | rno-let-7c | rno-let-7d | rno-let-7d* |
| rno-let-7e | rno-let-7e* | rno-let-7f | rno-let-7i | rno-let-7i* | rno-miR-1 |
| rno-miR-1* | rno-miR-100 | rno-miR-101a | rno-miR-101a* | rno-miR-101b | rno-miR-103 |
| rno-miR-106b | rno-miR-106b* | rno-miR-107 | rno-miR-10a-3p | rno-miR-10a-5p | rno-miR-10b |
| rno-miR-122 | rno-miR-124 | rno-miR-124* | rno-miR-125a-3p | rno-miR-125a-5p | rno-miR-125b* |
| rno-miR-125b-3p | rno-miR-125b-5p | rno-miR-126 | rno-miR-126* | rno-miR-127 | rno-miR-128 |
| rno-miR-129 | rno-miR-129* | rno-miR-130a | rno-miR-130b | rno-miR-132 | rno-miR-133a |
| rno-miR-133b | rno-miR-134 | rno-miR-135a | rno-miR-135a* | rno-miR-135b | rno-miR-136 |
| rno-miR-136* | rno-miR-137 | rno-miR-138 | rno-miR-138* | rno-miR-139-3p | rno-miR-139-5p |
| rno-miR-140 | rno-miR-140* | rno-miR-141 | rno-miR-142-3p | rno-miR-142-5p | rno-miR-143 |
| rno-miR-144 | rno-miR-145 | rno-miR-146a | rno-miR-146b | rno-miR-147 | rno-miR-148b-3p |
| rno-miR-148b-5p | rno-miR-150 | rno-miR-151 | rno-miR-151* | rno-miR-152 | rno-miR-153 |
| rno-miR-154 | rno-miR-15b | rno-miR-16 | rno-miR-17 | rno-miR-17-3p | rno-miR-181a |
| rno-miR-181a* | rno-miR-181b | rno-miR-181c | rno-miR-181d | rno-miR-182 | rno-miR-183 |
| rno-miR-184 | rno-miR-185 | rno-miR-186 | rno-miR-187 | rno-miR-188 | rno-miR-18a |
| rno-miR-190 | rno-miR-190b | rno-miR-191 | rno-miR-192 | rno-miR-193 | rno-miR-193* |
| rno-miR-194 | rno-miR-195 | rno-miR-196a | rno-miR-196a* | rno-miR-196b | rno-miR-196c |
| rno-miR-199a-3p | rno-miR-199a-5p | rno-miR-19a | rno-miR-19b | rno-miR-200a | rno-miR-200b |
| rno-miR-200c | rno-miR-203 | rno-miR-204 | rno-miR-204* | rno-miR-205 | rno-miR-206 |
| rno-miR-207 | rno-miR-208 | rno-miR-20a | rno-miR-20a* | rno-miR-20b-3p | rno-miR-20b-5p |
| rno-miR-21 | rno-miR-21* | rno-miR-210 | rno-miR-211 | rno-miR-212 | rno-miR-214 |
| rno-miR-215 | rno-miR-216a | rno-miR-217 | rno-miR-218 | rno-miR-218* | rno-miR-219-1-3p |
| rno-miR-219-2-3p | rno-miR-219-5p | rno-miR-22 | rno-miR-22* | rno-miR-221 | rno-miR-222 |
| rno-miR-223 | rno-miR-224 | rno-miR-23a | rno-miR-23a* | rno-miR-23b | rno-miR-24 |
| rno-miR-24-1* | rno-miR-24-2* | rno-miR-25 | rno-miR-25* | rno-miR-26a | rno-miR-26b |
| rno-miR-26b* | rno-miR-27a | rno-miR-27a* | rno-miR-27b | rno-miR-28 | rno-miR-28* |
| rno-miR-290 | rno-miR-291a-3p | rno-miR-291a-5p | rno-miR-292-3p | rno-miR-292-5p | rno-miR-296 |
| rno-miR-296* | rno-miR-297 | rno-miR-298 | rno-miR-299 | rno-miR-29a | rno-miR-29b |
| rno-miR-29b-1* | rno-miR-29b-2* | rno-miR-29c | rno-miR-29c* | rno-miR-300-3p | rno-miR-300-5p |
| rno-miR-301a | rno-miR-301b | rno-miR-30a | rno-miR-30a* | rno-miR-30b-3p | rno-miR-30b-5p |
| rno-miR-30c | rno-miR-30c-1* | rno-miR-30c-2* | rno-miR-30d | rno-miR-30d* | rno-miR-30e |
| rno-miR-30e* | rno-miR-31 | rno-miR-32 | rno-miR-320 | rno-miR-322 | rno-miR-322* |
| rno-miR-323 | rno-miR-323* | rno-miR-324-3p | rno-miR-324-5p | rno-miR-325-3p | rno-miR-325-5p |
| rno-miR-326 | rno-miR-327 | rno-miR-328 | rno-miR-329 | rno-miR-33 | rno-miR-330 |
| rno-miR-330* | rno-miR-331 | rno-miR-333 | rno-miR-335 | rno-miR-336 | rno-miR-337 |
| rno-miR-338 | rno-miR-338* | rno-miR-339-3p | rno-miR-339-5p | rno-miR-340-3p | rno-miR-340-5p |
| rno-miR-341 | rno-miR-342-3p | rno-miR-342-5p | rno-miR-343 | rno-miR-344-3p | rno-miR-344-5p |
| rno-miR-345-3p | rno-miR-345-5p | rno-miR-346 | rno-miR-347 | rno-miR-349 | rno-miR-34a |

| | | | | | |
|---|---|---|---|---|---|
| rno-miR-34b | rno-miR-34c | rno-miR-34c* | rno-miR-350 | rno-miR-351 | rno-miR-352 |
| rno-miR-361 | rno-miR-363 | rno-miR-363* | rno-miR-365 | rno-miR-369-3p | rno-miR-369-5p |
| rno-miR-370 | rno-miR-374 | rno-miR-375 | rno-miR-376a | rno-miR-376a* | rno-miR-376b-3p |
| rno-miR-376b-5p | rno-miR-376c | rno-miR-377 | rno-miR-378 | rno-miR-378* | rno-miR-379 |
| rno-miR-379* | rno-miR-380 | rno-miR-381 | rno-miR-382* | rno-miR-383 | |
| rno-miR-384-3p | rno-miR-384-5p | rno-miR-409-3p | rno-miR-409-5p | rno-miR-410 | rno-miR-411 |
| rno-miR-412 | rno-miR-421 | rno-miR-423 | rno-miR-425 | rno-miR-429 | rno-miR-431 |
| rno-miR-433 | rno-miR-434 | rno-miR-448 | rno-miR-449a | rno-miR-450a | rno-miR-451 |
| rno-miR-455 | rno-miR-463 | rno-miR-466b | rno-miR-466c | rno-miR-471 | rno-miR-483 |
| rno-miR-484 | rno-miR-485 | rno-miR-487b | rno-miR-488 | rno-miR-489 | rno-miR-493 |
| rno-miR-494 | rno-miR-495 | rno-miR-497 | rno-miR-499 | rno-miR-500 | rno-miR-501 |
| rno-miR-503 | rno-miR-505 | rno-miR-532-3p | rno-miR-532-5p | rno-miR-539 | rno-miR-540 |
| rno-miR-541 | rno-miR-542-3p | rno-miR-542-5p | rno-miR-543 | rno-miR-543* | rno-miR-551b |
| rno-miR-598-3p | rno-miR-598-5p | rno-miR-652 | rno-miR-664 | rno-miR-671 | rno-miR-672 |
| rno-miR-673 | rno-miR-674-3p | rno-miR-674-5p | rno-miR-708 | rno-miR-708* | rno-miR-742 |
| rno-miR-743a | rno-miR-743b | rno-miR-758 | rno-miR-760-3p | rno-miR-760-5p | rno-miR-770 |
| rno-miR-7a | rno-miR-7a* | rno-miR-7b | rno-miR-871 | rno-miR-872 | rno-miR-872* |
| rno-miR-873 | rno-miR-874 | rno-miR-877 | rno-miR-878 | rno-miR-879 | rno-miR-880 |
| rno-miR-881 | rno-miR-883 | rno-miR-9 | rno-miR-9* | rno-miR-92a | rno-miR-92b |
| rno-miR-93 | rno-miR-96 | rno-miR-98 | rno-miR-99a | rno-miR-99a* | rno-miR-99b |
| rno-miR-99b* | | | SCorner3 hur_1 hur_2 hur_4 hur_6 miRNABrightCorner mr_ | | |

Dried and labeled samples were resuspended in 18 µl of nuclease-free water and denaturated at 100° C. for 5 minutes in the presence of 1× Blocking Agent and 1× Hi-RPM Hybridization Buffer in a final volume of 45 µl and immediately placed on ice. These mixes were used for the hybridization, which was done in microarray hybridization chambers (Agilent Technologies, Palo Alto, Calif.), as previously described [Farago N et al. 2008]. After hybridization the slides were washed in Gene Expression Wash buffer 1 containing Triton X-102 from Agilent Technologies at room temperature for 1 minute, then in Gene Expression Wash buffer 2 containing Triton X-102 at 37° C. for another 1 minute before scanning. Each array was scanned as described earlier [Feher L Z et al. 2005] with an Agilent Scanner with 5 µm resolution. Output image analysis and feature extraction was done using Feature Extraction software of Agilent Technologies.

To confirm microarray results, quantitative real-time PCR (QRT-PCR) was used. The reverse transcription reaction was performed with the TaqMan® MiRNA Reverse Transcription Kit (Applied Biosystems, Calif., USA). 350 ng from each sample was reverse transcribed in the presence of 5×RT TaqMan® MiRNA Assays (Applied Biosystems, Calif., USA). 8 µl reaction mixture contained 0.2 µl dNTPs, 1.5 µl MultiScribe™ Reverse Transcriptase (50 U/µL), 0.8 µl 10×RT Buffer, 0.9 µl MgCl$_2$, 0.1 µl RNase Inhibitor (20 U/µL), 1.5 µl 5×RT primer and the template in a total volume of 3 Reverse Transcription was carried out with the following cycling parameters in a thermocycler (Bioneer, Daedong, Korea): 16° C. for 2 minutes, 42° C. for 1 minutes, 50° C. for 1 second, 45 cycles, then hold the samples on 85° C. for 5 minutes. After dilution with 64 µl of water, 9 µl of the diluted reaction mix was used as template in QRT-PCR. Reactions were performed on a RotorGene 3000 instrument (Corbett Research, Sydney, Australia) with the TaqMan protocol. 20 µl reaction mixture contained 10 µl TaqMan® Universal PCR Master Mix (Applied Biosystems), 1 µl of the TaqMan® MiRNA Assays and 9 µl of the diluted cDNA.

Microarray and QRT-PCR data are presented in the text and tables as mean±SD, all other data are mean±SEM. One way analysis of variance (ANOVA) followed by Fisher's least significant difference (LSD) post-hoc test was used to evaluate differences in mean values of infarct size, LDH release and hemodynamic parameters between groups.

Statistical analysis of miRNA microarrays were done as described earlier by using the Feature Extraction software of Agilent Technologies [Punkas L G et al. 2005]. All the individual miRNAs were represented by 20 different probes on the array. A miRNA was considered as detected, if at least one probe from all the 20 probes was detected. Total gene signal is equal of the sum of the signals of the individual probes. Expressions of all the 350 miRNAs found in the Sanger miRBase (version 10.1) were checked Expressions of all the 350 miRNAs found in the Sanger miRBase (version 10.1) were checked.

Changes in gene expression can be determined by several alternative ways. On the one hand there are at least three ways to calculate expression ratios from the obtained microarray expression raw data (as e.g. expressed by fluorescent signal intensity).

1. Calculation of microRNA expression ratios from raw data pairs obtained in any compared two samples
    A. comparing randomly selected pairs of raw data of a certain microRNA in any compared two samples. (This kind of calculaton was used on FIGS. 2 to 6.)
    B. or comparing all possible combinations of raw data pairs in any compared two samples (This kind of calculation was used on FIGS. 7 to 10)
2. Calculation of a single expression ratio from the average of expression raw data in any compared two samples, respectively.

On the other hand there are several possible plotting methods to demonstrate alterations in gene expression. The generally used plotting methods are the followings:

1. Plotting average expression ratio (the ratio of compared raw data): In this case up-regulation is presented as number higher than 1 and represent fold change. However, in case of down-regulation the number is between 0 and 1, resulting in an uneven scale (up- and down-regulation is visually not comparable).
2. Plotting fold change values: In case of down-regulation, expression ratio is between 1 and 0. In this case, fold change is defined as the negative of the inverse of the expression ratio, i.e. 1/expression ratio x−1. Therefore, fold change values between −1 and 1 cannot be mathematically interpreted, and it means no change in expression. (This kind of plotting was used on FIGS. 2 to 6.)
3. Plotting log 2 of the expression ratio, which yields a comparable scale, however, interpretation of these data requires further mathematical approach. E.g. the number 2 on log 2 scale is equal to 4 fold up-regulation. The widely accepted 1.5 down- or up-regulation is 0.585 or −0.585 [log 2(1.5) or log 2(1/1.5) on this scale. A preferred 1.8 fold change corresponds to 0.848 or −0.848, respectively, whereas a 2 fold change is 1 or −1, respectively (This kind of plotting was used on FIGS. 7 to 10).

Using two tailed two sample unequal variance Student t-test, the p-value was determined to find significant gene expression changes. MiRNA expression ratios with p value<0.05 and fold change <−1.5 or fold change >1.5 were considered as repression or overexpression, respectively.

Experimental Protocol for Exogenous MiRNA Mimic or Inhibitor to Induce Cytoprotective Effect in Rat Cardiac Myocytes Subjected to Simulated Ischemia-Reperfusion Neonatal rat cardiomyocytes were prepared from newborn Wistar rats. Ventricles were minced digested in 0.25% trypsin (Gibco BRL) for 30 minutes. After digestion, the cell suspension was centrifuged (450×g for 15 minutes at 4° C.), and the cell pellet was re-suspended in culture medium (Dulbecco's modified Eagle's medium (DMEM), supplemented with 10% fetal bovine serum (FBS), L-Glutamine, and Antibiotic Antimycotic Cocktail (penicillin, streptomycin, amphotericin-B)), all obtained from Sigma. The dissociated cells were pre-plated in 6-well plates at 37° C. for 90 minutes to enrich the culture with cardiomyocytes. The non-adherent myocytes were collected and cells were counted in a Burker's chamber and then were plated at a density of $2*10^4$ cell/well in 96-wells plates $5\times10^4$ cells/well onto 48-wells plates, $10^5$ cells/well onto 24-wells plates. The culture was grown for 3 days before experimentation. Culture medium was changed the day after preparation. The cells were maintained at 37° C. in a standard $CO_2$ incubator (5% $CO_2$)

Synthesized miRNAs (Dharmacon) were transfected into rat neonatal cardiomyocytes using the transfection protocol recommended by manufacturer. Either individual miRNA Mimics and Inhibitors or cocktails thereof were applied as described in Example 3. The Miridian miRNA Mimics and Inhibitors were diluted in antibiotic-free medium, and were incubated with the cells up to—24 hours. As a transfection agent the recommended DharmaFect 1 siRNA transfection reagent was used. For negative control transfection cel-miR-67 (a *C. elegans* miRNA) was used, which shows minimal sequence identity to the known rat miRNAs.

After completion of the transfection procedure, transfected cells were subjected to a simulated ischemia-reperfusion protocol. To simulate ischemic conditions, the culture medium was replaced with a hypoxic solution containing in mM: NaCl 119, KCl 5.4, MgSO4 1.3, NaH2PO4 1.2, HEPES 5, MgCl2 0.5, CaCl2 0.9, Na-lactate 20, BSA 0.1%. To induce hypoxia the cells were then placed in a hypoxic chamber gassed through with a mixture of 95% N2 and 5% CO2 for 4 hours at 37° C. After hypoxia, the cells were reoxygenated and the hypoxic medium was replaced by completed DMEM culture medium at 37° C. in 95% air and 5% CO2 for two hours (simulated reperfusion). Cardiomyocyte viability was determined by means of calcein-AM staining. Live cells are characterized by the presence of ubiquitous intracellular esterases. Esterase activity can be determined by the enzymatic conversion of the virtually non-fluorescent cell-permeant calcein-AM to the intensely fluorescent calcein. The polyanionic dye calcein is well retained within live cells, producing an intense uniform green fluorescence in live cells. After simulated ischemia-reperfusion, the cells were washed to remove extracellular esterases and subsequently were incubated with calcein-AM (2 uM, Promokine) dissolved in D-PBS for 30 minutes. After the removal of the dye, fluorescence intensity of each EB was detected by fluorescent plate reader (FluoStar Optima, BMG Labtech) with the excitation wavelength of 495 nm and emission wavelength of 520 nm. Fluorescence intensity reflecting the cell viability was evaluated in each well. Background fluorescence intensity (dye control) was subtracted from the fluorescence intensity of each well, and the average intensity of each group was plotted. The cytoprotective effect of different miRNA mimics and inhibitors was compared to simulated ischemic control groups and to the negative control transfected simulated ischemic groups.

Example 1

Identification of MiRNAs Involved in Ischemia-Reperfusion Injury

To determine miRNAs involved in ischemia-reperfusion injury, preconditioning and postconditioning miRNAs were isolated from the anterior wall of left ventricles after two hours of reperfusion. The relative changes in miRNA expression after ischemia-reperfusion were determined using the time-matched control group as baseline. In response to ischemia-reperfusion, approximately 150 miRNAs showed expression among the total 350 rat miRNAs studied. We have confirmed the microarray data by measuring the expression of 17 randomly selected miRNAs using QRT-PCR. Expression changes of 15 miRNAs were confirmed by QRT-PCR (Table 2).

To demonstrate whether cardioprotective adaptation leads to alterations of miRNA profile in the myocardium, miRNA expression induced by ischemic preconditioning and postconditioning was compared either to the non-ischemic time-matched control group or to the non-conditioned ischemia-reperfusion group or both. Those miRNAs, which were significantly altered both by ischemia-reperfusion and by cardioprotective maneuvers in the same direction and extent, likely represent miRNAs associated with ischemia-reperfusion injury itself (FIG. 2.).

We considered miRNAs to be related to myocardial ischemia-reperfusion injury, when ischemia-reperfusion significantly altered their expression, however, cardioprotection by pre- or postconditioning did not affect these alterations. Thus, if no significant up- or down-regulation by pre- and/or postconditioning is observed in comparison with the regulation by ischemia-reperfusion, these miRNAs are merely of diagnostic value for ischemic disease, however, their tissue protective value not related to either pre- or postconditioning cannot be excluded. For example, those members of the let-7 family the up-regulation of which are close to a significant level, are potential candidates as pre-ischemic cytoprotective miRNAs (e.g. let-7a, 7b, 7c, 7d, 7d*, 7f, data not shown). Indeed, miRNAs let-7b, let-7e and let-7i proved to be actually cytoprotective in the present set of experiments (FIG. 10, panels A and B).

Such expression pattern was characteristic in case of a number of miRNAs 125a-5p, 331, 333, 378*, 466b, 652, 92a, and 99b (down-regulation of miR-99b was found non-significant therefore further confirmation is needed). Interestingly, in these samples regarding the aforementioned miRNAs all changes by ischemia-reperfusion was repression (except miR-466b) of the miRNA expressions, therefore, exogenous application of the aforementioned miRNAs to normalize the tissue miRNA content may probably protect the tissue against ischemia-reperfusion injury.

Example 2

Identification of MiRNAs Involved in Cardioprotection by Ischemic Pre and Postconditioning We considered miRNAs to be related to ischemic preconditioning when the preconditioning maneuver resulted in a significant attenuation or a significant enhancement of the effect of ischemia-reperfusion on miRNA expression. These miRNAs include the cases when preconditioning induced significant miRNA expression alterations compared both to the non-ischemic time-matched control group and to the non-conditioned ischemia-reperfusion group (miRNA-139-3p, 139-5p, 188, 192, hatched bars in the figures; see e.g. FIG. 5.). MiRNAs that were significantly altered by ischemia-reperfusion and were significantly reversed by preconditioning were also rendered to this category (miRNA-320; FIG. 3. A). Changes of this group of miRNAs likely contribute to the development of the preconditioning-induced cardioprotection. The direction of changes observed in case of preconditioning compared to ischemia-reperfusion shows if a miRNA mimic (when preconditioning increased a miRNA expression as compared to ischemia-reperfusion) or an inhibitor (when preconditioning decreased a miRNA expression as compared to ischemia-reperfusion) is applicable for therapy of ischemic disease.

To further assess miRNA expression in cardiac adaptation, the effect of ischemic postconditioning on myocardial miRNA expression was determined. Ischemic postconditioning-associated miRNAs were identified based on the attenuating or enhancing effect of postconditioning on ischemic-reperfusion-induced miRNA expression. These include miRNAs that were significantly affected by postconditioning compared to the non-conditioned ischemia-reperfusion group and preferably also to the non-ischemic time-matched control group. The following miRNAs on FIG. 6: 130a, 16, 21, 22*, 26b, 30b-5p, 30c, 30c-1*, 30e, 339-3p, 450a, 499, 760-5p, 99a, 99a*, while the effect of ischemia-reperfusion in itself appeared to be under the significance level, are to be considered as deleterious rather than cytoprotective, since postconditioning induced a significant down-regulation as compared to non-conditioned ischemia-reperfusion group, i.e. they may be considered as Pathomirs. Thus, antagonists or inhibitors against them should have cytoprotective effect against ischemia-reperfusion injury. MiRNAs that were significantly altered by ischemia-reperfusion and were significantly reversed by postconditioning, i.e. miRNA-494, 33, 19a, 19b, 208, and 106b, were also rendered to this category (FIG. 3. B and C), where the above mechanism is more pronounced. The direction of changes observed in case of postconditioning compared to ischemia-reperfusion shows if a miRNA mimic (when postconditioning increased expression of a miRNA, i.e. a Protectomir, as compared to ischemia-reperfusion) or an inhibitor (when postconditioning decreased expression a miRNA, i.e. a Pathomir as compared to ischemia-reperfusion) is applicable for therapy of ischemic disease. An inhibitor against miRNA has been tested in Example 3. This group is composed of miRNAs that are involved in the mechanism of cardioprotection by postconditioning.

We have found two miRNAs (miRNA-125b* and 487b) showing a similar expression pattern due to both ischemic preconditioning and postconditioning. Both ischemic preconditioning and ischemic postconditioning significantly attenuated ischemia-reperfusion-induced miRNA-expression, suggesting an important role of these miRNAs in cardioprotective signaling (FIGS. 4. A and B). However, the sense or direction of the alteration are the opposite in the two samples, therefore an miRNA-125b* mimic or an inhibitor against miRNA-487b should be cyto- and cardioprotective. In addition, three miRNAs (miR-352, miR-532-3p and miR-93) were similarly affected by both pre- and postconditioning, without being affected by ischemia-reperfusion injury (FIG. 4. C).

The results are also summarized in Table 4.

We have confirmed the microarray data by measuring the expression of 17 randomly selected miRNAs using QRT-PCR see also in Example 1 (Table 2).

We conclude that all miRNAs involved in cardioprotection by either pre or postconditioning, can be potential target for application of either miRNA mimic or miRNA inhibitor therapy. Based on these results, the potential effect of the miRNAs were assessed and suggestion was made as to their use.

If the given miRNA is significantly down-regulated in ischemia-reperfusion as compared to the non-ischemic control while the alteration of expression level neither in the preconditioned nor in the postconditioned sample as compared to ischemia-reperfusion is significant, a potential therapeutic, cytoprotective and anti-ischemic effect of their miRNA mimics still can not be excluded. If the given miRNA is significantly up-regulated in ischemia-reperfusion as compared to the non-ischemic control while the alteration of expression level neither in the preconditioned nor in the postconditioned sample is significant as compared to ischemia-reperfusion, preferentially an increase of these miRNAs may indicate a potential therapeutic effect of their inhibitors (see e.g. miR-466b on FIG. 2).

If the down-regulation of the miRNA level is significant either in the preconditioned or in the postconditioned sample, or both in comparison with the ischemic/reperfused sample, the effect of the miRNA itself is considered to be cell damaging, i.e. cytopathic, therefore, their miRNA inhibitors are considered to be cytoprotective and anti-ischemic in ischemic conditions. This is particularly pronounced if the miRNA is up-regulated in the ischemic/reperfused sample as compared to the non-ischemic control. In this case, an inhibitor of the miRNA should have a cytoprotective and anti-ischemic effect.

If the up-regulation of the miRNA level is significant either in the preconditioned or in the postconditioned sample, or both in comparison with the ischemic/reperfused sample, the effect of the miRNA is considered to be protective, therefore, their miRNA mimics considered to be cytoprotective and anti-ischemic in ischemic conditions.

We have found a small set of miRNAs which significantly regulated in the opposite direction in ischemic preconditioning and in ischemic postconditioning. For example, rno-miR-335 was down-regulated significantly in ischemic preconditioning vs. ischemia-reperfusion and up-regulated significantly in ischemic postconditioning vs. ischemia-reperfusion (data not shown).

The therapeutic value of miRNA-s with an expression pattern like this may be different in patients predisposed to ischemia and patients attacked (or presumably attacked) by ischemia. In case of a patient predisposed to ischemia, e.g. a patient with risk factor or one who is to be subjected to cardiac intervention the down-regulation (e.g. of miR-335) of such a miRNA, a Pathomir in this setting, may cause an endogenous protection against an ischemia-reperfusion injury, and in this stage administration of antagonist in case of a miRNA species downregulated in preconditioning may provide some protection to the patient and improve his/her prospects for recovery. However, the opposite is true after an ischemic attack has occurred and in such conditions the same miRNA may act as a Protectomir. eg. during reperfusion. MiRNA species, which act as Protectomirs before ischemia and as Pathomirs in reperfusion may be found later.

Example 3

Viability in MiRNA-Transfected Primary Cardiomyocytes after Simulated Ischemia-Reperfusion Based on the miRNA-microarray results, several miRNAs were determined as involved in cardioprotection or in ischemic injury. In order to further prove the causative relationship between the affected miRNAs and cytoprotection and to prove the applicability of certain miRNA mimics or miRNA inhibitors, some cardioprotection-associated and cytopathy associated miRNAs or combinations thereof were selected to test if their mimics or inhibitors applied exogenously are able to provide cytoprotective action in cardiac myocytes subjected to simulated ischemia-reperfusion. Four hours of simulated ischemia followed by reoxygenation caused significantly higher cell death in neonatal cardiomyocytes than in time-matched controls kept under normoxic conditions. In preliminary cell transfection experiments 3 to 5 samples were used whereas later the sample number was increased up to 8. Cell viability was significantly increased by the preconditioning-associated rno-miR-139-5p, by the post-conditioning-associated rno-miR-33 and rno-miR-494 (inhibitor). Viability was significantly increased by those two miRNAs (rno-miR-125b* and the inhibitor against −487b), which were similarly affected by both pre- and postconditioning.

As we described in Example 1, even if no statistically significant up- or down-regulation by pre- and/or postconditioning is observed in comparison with ischemia/reperfusion, it cannot be excluded that these miRNAs have tissue protective value not related to either pre- or postconditioning. For example, in preliminary cell transfection experiments carried out with 3 to 5 samples certain members of the let-7 family the up-regulation of which were close to a significant level, were considered as potential candidates as pre-ischemic cytoprotective miRNAs. Consistently with this hypothesis, we tested the applicability of microRNA Mimic of let-7b with increased sample numbers (8 samples). In these experiments, we found that microRNA Mimic of let-7b can significantly increase the viability of cardiomyocytes subjected to simulated ischemia/reperfusion (Table 3). These results suggest that a careful statistical analysis of the results is advisable according to the invention.

Randomly selected combinations of the randomly selected cardioprotective and/or cytopathic microRNAs (see Table 3b) were also effective as shown on FIG. 11. The applied combinations were also effective against simulated ischemia/reperfusion injury.

These results prove that miRNAs that we identified as cardioprotective in Example 2 are effective to treat ischemia-reperfusion injury when corresponding miRNA mimics or inhibitors as appropriate is used.

Example 4

Treatment of Patients Having an Assumed Ischemic Attack or at Risk Thereof

Case 1

A patient suffering from atherosclerosis is admitted to the hospital at night with complaints of serious unstable angina pectoris lasted for at least 15 minutes, after 1 h from the start of the symptoms. Symptoms have not ameliorated significantly upon nitroglycerine treatment in the home of the patient. Patient case history has shown that two weeks ago a less serious angina occurred treated with nitroglycerine.

A coronary angiogram shows stenotic (narrowed) coronary arteries and a decision on an emergency percutaneous coronary intervention (PCI) is made. PCI is started after 40 minutes of hospitalization.

Reperfusion is made upon a surgical intervention with a post-conditioning protocol. Before and/or during PCI a cocktail of agonists of pre-ischemic and post-ischemic cytoprotective miRNAs are administered to the patient locally into the blood flow and administration of post-ischemic cytoprotective miRNAs is repeated by infusion after 3.5 hours from reperfusion.

Case 2

A patient (a woman of age 55 with no history of CVD) visits a non-PCI center after 5 hours of symptom onset transitional symptoms of ischemic heart attack which diagnosis is confirmed and a spontaneous reperfusion is established. The patient is hospitalized and immediately receives a cocktail of agonists of post-ischemic cytoprotective and antagonists of post-ischemic cytotoxic miRNAs together with a low dose of fibrinolytic therapy and patient status is monitored. After normalization of her status she is released and asked to return to a control in two weeks.

Case 3

A patient (a man of age 60, a strong smoker, hyperlipidemic) attends regular control in a non PCI center. Based on regular blood pressure measurements at home, confirmed at the control by medical personnel the systolic blood pressure is 160±5 Hgmm. The calculated CVD risk factor is 19-24 and there is a high risk of acute ischemic attack. A preventive therapy of a cocktail of agonists of pre-ischemic cytoprotective and antagonists of pre-ischemic cytotoxic miRNAs are subscribed together with a antihyperlipidemic statins, and antihypertensive agents to ensure cytoprotection in case of an ischemic-reperfusion injury. The patient is strongly warned to abandon smoking, and walk at least half an hour a day and a diet is proposed.

In a year upon a second control the CVD risk factor of the patient is reduced to 8 due to ceasing smoking, a reduced total cholesterol-HDL ratio. On the precondition that conduct is not changed the miRNA compound therapy is abandoned.

TABLES

TABLE 1

Markers of Myocardial Tissue Injury

|  | Time-matched control | Ischemia-Reperfusion | Ischemic preconditioning | Ischemic postconditioning |
|---|---|---|---|---|
| Animal weight (g) | 284 ± 10 | 282 ± 11 | 275 ± 9 | 276 ± 4 |
| Area at risk (%) | n.a. | 37.4 ± 1.7 | 40.1 ± 4.3 | 43.3 ± 3.5 |

TABLE 1-continued

Markers of Myocardial Tissue Injury

|  | Time-matched control | Ischemia-Reperfusion | Ischemic preconditioning | Ischemic postconditioning |
|---|---|---|---|---|
| Infarct size (%) | n.a. | 48.3 ± 3.5 | 15.3 ± 3.7 * | 21.7 ± 1.5 * |
| LDH release (mU/min/g) | n.a. | 3.31 ± 0.45 | 0.82 ± 0.16 * | 1.51 ± 0.38 * |
| Heart rate (BPM) | 274 ± 8 | 283 ± 12 | 279 ± 8 | 295 ± 14 |
| Coronary flow (ml/min) | 10.1 ± 1 | 9.9 ± 1 | 10.8 ± 0.7 | 12.2 ± 1.4 |

Values are mean ± SEM. n.a. not applicable;
* $p < 0.05$ vs. ischemia-reperfusion; area at risk and infarct size were measured after 120 min of reperfusion; LDH release was measured from coronary effluent collected during the first 5 min of reperfusion, heart rate and coronary flow data presented here was measured at the end of perfusion protocols.

TABLE 2

Validation of Microarray Data with QRT-PCR ischemia-reperfusion vs. Time-matched Control

| miRNA name | Chip result | QRT-PCR result | Confirmed |
|---|---|---|---|
| rno-let-7c | −1.83 ± 0.20 | −2.30 ± 0.76 | yes |
| rno-let-7d | −1.53 ± 0.20 | −3.94 ± 1.33 | yes |
| rno-miR-19a | 1.57 ± 0.13 | 2.05 ± 0.45 | yes |
| rno-miR-19b | 1.82 ± 0.73 | 2.33 ± 0.35 | yes |
| rno-miR-208 | 1.79 ± 0.67 | 2.21 ± 0.63 | yes |
| rno-miR-30c | 0.91 ± 0.40 | −1.05 ± 0.53 | yes |
| rno-miR-125b* | −22.64 ± 4.45 | −53.22 ± 18.51 | yes |
| Ischemic Preconditioning vs. Ischemia-Reperfusion | | | |
| rno-miR-320 | 1.64 ± 0.12 | 3.89 ± 1.11 | yes |
| rno-miR-125b* | 18.90 ± 2.25 | 46.88 ± 16.43 | yes |
| Ischemic Postconditioning vs. Ischemia-Reperfusion | | | |
| rno-miR-19b | −2.08 ± 0.55 | −4.64 ± 1.86 | yes |
| rno-miR-30c | −2.06 ± 0.55 | −2.07 ± 0.44 | yes |
| rno-miR-20a | −2.01 ± 0.50 | −1.65 ± 0.25 | yes |
| rno-miR-125b* | 8.33 ± 0.99 | 1.96 ± 0.34 | yes |

Values are mean ± SD fold expression changes.

TABLE 3

Effect of pre- and/or postconditioning- associated miRNAs on cell viability after simulated ischemia-reperfusion.

|  | Myocyte Viability |
|---|---|
| miRNA Mimic | |
| Non-transfected | 100 ± 3 |
| Neg. Control | 101 ± 1 |

TABLE 3-continued

Effect of pre- and/or postconditioning- associated miRNAs on cell viability after simulated ischemia-reperfusion.

|  | Myocyte Viability |
|---|---|
| rno-let-7b | 128 ± 7 |
| rno-miR-139-5p | 119 ± 2* |
| rno-miR-125b* | 128 ± 3* |
| rno-miR-33 | 127 ± 2* |
| miRNA Inhibitor | |
| Non-transfected | 100 ± 3 |
| Neg. Control | 102 ± 2 |
| rno-miR-494 | 123 ± 2* |
| rno-miR-487b | 121 ± 2* |

Data are mean ± SEM
*$p < 0.05$ vs neg. control transfected cells; one-way ANOVA followed by Fischer LSD posthoc test, n = 8 in each group.

TABLE 3.b

| 1 | 139-5p MIMIC | 33 MIMIC | 125b* MIMIC | let-7b MIMIC |
|---|---|---|---|---|
| 2 | 139-5p MIMIC | 33 MIMIC | 125b* MIMIC | 494 INHIBITOR |
| 3 | 139-5p MIMIC | 33 MIMIC | let-7b MIMIC | 487b INHIBITOR |
| 4 | 139-5p MIMIC | 125b* MIMIC | let-7b MIMIC | 487b INHIBITOR |
| 5 | 139-5p MIMIC | let-7b MIMIC | 494 INHIBITOR | 487b INHIBITOR |
| 6 | 33 MIMIC | 125b* MIMIC | let-7b MIMIC | 494 INHIBITOR |

TABLE 4

A summary of regulation of miRNA species shown on the Figures. Certain miRNAs of uncertain category (shown in italics) were more presicely defined in later experiments shown in TABLE 5, below

| miRNA | IR/C | PRE/C | POST/C | PRE/IR ///////// | POST/IR ///////// | Effect |
|---|---|---|---|---|---|---|
| FIG. 2 | | | | | | |
| miR-125a-5p | ↓S | ns | ↓S | ns | ns | |
| miR-331 | ↓S | ↓S | ns | ns | ns | |
| miR-333 | ↓S | ↓S | ns | ns | ns | |
| miR-378* | ↓S | ↓S | ↓S | ns | ns | |
| miR-466b | ↑S | ns | ns | ns | ns | |
| miR-652 | ↓S | ↓S | ↓S | ns | ns | |
| miR-92a | ↓S | ↓S | ↓S | ns | ns | |
| miR-99b | ns | ↓S | ↓S | ns | ns | |

TABLE 4-continued

A summary of regulation of miRNA species shown on the Figures. Certain miRNAs of uncertain category (shown in italics) were more presicely defined in later experiments shown in TABLE 5, below

| miRNA | IR/C | PRE/C | POST/C | PRE/IR | POST/IR | Effect |
|---|---|---|---|---|---|---|
| FIG. 3 | | | | | | |
| *miR-320* | ↓*S* | *ns* | *ns* | ↗*S* | *ns* | *pre-isch. cytoprotective* |
| miR-494 | ↑S | ↑S | ↑S | ns | ↓S | post-isch. cytotoxic |
| miR-33 | ↓S | ↓S | ns | ns | ↑S | post-isch. cytoprotective |
| miR-19a | ↑S | ns | ns | ns | ↓S | post-isch. cytotoxic |
| miR-19b | ↑S | ↑S | ns | ns | ↓S | post-isch. cytotoxic |
| miR-208 | ↑S | ↑S | ns | ns | ↓SS | post-isch. cytotoxic |
| miR-106b | ↑S | ↑S | ns | ns | ↓S | post-isch. cytotoxic |
| FIG. 4 | | | | | | |
| *miR-487b* | ↗*S* | *ns* | *ns* | ↓*S* | ↓*S* | *pre/post isch cytotoxic-> pre isch cytotoxic* |
| miR-125b* | ↓SS | ns | ↓S | ↑SS | ↑SS | pre/post isch cytoprotective |
| miR-352 | ns | ns | ns | ↓S | ↓S | pre/post isch cytopathic |
| miR-532-3p | ns | ns | ns | ↑S | ↑S | pre/post isch cytoprotective |
| miR-93 | ns | ns | ↓S | ↓SS | ↓SS | pre/post isch cytopathic |
| FIG. 5 | | | | | | |
| *miR-139-3p* | *ns* | ↑*SS* | *ns* | ↑*SS* | *ns* | pre-isch cytoprotective -> pre/post isch cytoprotective |
| miR-139-5p | ↑S | ↑SS | ns | ↑SS | ns | pre-isch cytoprotective |
| *miR-188* | *ns* | ↑*S* | *ns* | ↑*S* | *ns* | *pre-isch cytoprotective -> pre/post isch cytoprotective* |
| miR-192 | ns | ↑S | ns | ↑S | ns | pre-isch cytoprotective |
| FIG. 6 | | | | | | |
| miR-130a | ns | ns | ns | ns | ↓S | post isch cytopathic |
| miR-16 | ns | ns | ↓S | ns | ↓S | post isch cytopathic |
| miR-21 | ns | ns | ns | ns | ↓S | post isch cytopathic |
| miR-22* | ns | ns | ns | ns | ↓S | post isch cytopathic |
| miR-26b | ns | ns | ↓S | ns | ↓S | post isch cytopathic |
| miR-30b-5p | ns | ns | ns | ns | ↓S | post isch cytopathic |
| miR-30c | ns | ns | ns | ns | ↓S | post isch cytopathic |
| miR-30c-1* | ns | ns | ns | ns | ↓S | post isch cytopathic |
| miR-30e | ns | ns | ns | ns | ↓S | post isch cytopathic |
| miR-339-3p | ns | ns | ns | ns | ↓S | post isch cytopathic |
| miR-450a | ns | ns | ns | ns | ↓S | post isch cytopathic |
| miR-499 | ns | ns | ↓S | ns | ↓S | post isch cytopathic |
| miR-760-5p | ns | ns | ↓S | ns | ↓S | post isch cytopathic |
| miR-99a | ns | ns | ↓S | ns | ↓S | post isch cytopathic |
| miR-99a* | ns | ns | ↓S | ns | ↓S | post isch cytopathic |

↑ up-regulation
↓ down-regulation
ns: non-significant regulation: below 1.5 fold (either positive or negative)
S: Significant regulation limit: 1.5 fold
SS: Very significant regulation
Bold: Preferred miRNA species.

TABLE 5

A summary of regulation of miRNA species shown on the Figures.

| miRNA | IR/C | PRE/C | POST/C | PRE/IR | POST/IR | Effect |
|---|---|---|---|---|---|---|
| FIG. 7 | | | | | | |
| miR-92a | ↓S | ↓S | ↓S? | ns | ns | |
| miR-877 | ↓S | ↓S | ↓S | ns | ns | |
| miR-652 | ↓S | ↓S | ns | ns | ns | |
| miR-494 | ↑S | ↑S | ↑S | ns | ns | post-isch. cytopathic? |
| miR-378* | ↓S | ↓S | ns | ns | ns | |
| miR-333 | ↓S | ↓S | ns | ns | ns | post-isch. cytoprotective? |
| miR-331 | ↓S | ↓S | ns | ns | ns | |
| miR-322 | ↑S | ↑S | ↑S | ns | ns | |
| miR-125a-5p | ↓S | ns | ↓S | ns | ns | |

TABLE 5-continued

A summary of regulation of miRNA species shown on the Figures.

| miRNA | IR/C | PRE/C | POST/C | PRE/IR | POST/IR | Effect |
|---|---|---|---|---|---|---|
| FIG. 8a pre/post | | | | | | |
| miR-188 | ns | ↑S | ↑S | ↑S | ↑S | pre/post isch cytoprotective |
| FIG. 8b pre/post | | | | | | |
| miR-125b* | ↓SS | ns | ns | ↑SS | ↑SS | pre/post isch cytoprotective |
| miR-139-3p | ↓S | ↑S | ns | ↑SS | ↑S | pre/post-isch cytoprotective |
| miR-320 | ↓S | ns | ns | ↑S | ↑S | pre/post-isch cytoprotective |
| miR-532-3p | ↓S | ns | ns | ↑S | ↑SS | pre/post isch cytoprotective |
| FIG. 9a pre | | | | | | |
| miR-451 | ns | ↑S | ns | ↑S | ns | pre-isch cytoprotective |
| miR-212 | ns | ↑S | ns | ↑SS | ns | pre-isch cytoprotective |
| miR-192 | ns | ↑S | ns | ↑S | ns | pre-isch cytoprotective |
| miR-139-5p | ns | ↑SS | ↑S | ↑SS | ns | pre-isch cytoprotective |
| FIG. 9b | | | | | | |
| miR-487b | ↑S | ns | ↑S | ↓S | ns | pre isch cytotoxic |
| FIG. 10.a post | | | | | | |
| miR-let7e | ns | ns | ns | ns | ↑S | post-isch. cytoprotective |
| miR-let7l | ns | ns | ns | ns | ↑S | post-isch. cytoprotective |
| miR-1 | ns | ns | ns | ns | ↑S | post-isch. cytoprotective |
| FIG. 11.b | | | | | | |
| miR-503 | ↓S | ↓S | ns | ns | ↑S | post-isch. cytoprotective |
| miR-335 | ↓S | ↓S | ns | ↓S | ↑SS | post-isch. cytoprotective |
| miR-33 | ↓S | ↓S | ns | ns | ↑SS | post-isch. cytoprotective |
| miR-328 | ↓S | ↓S | ns | ns | ↓S | post-isch. cytoprotective |
| miR-208 | ↑S | ↑S | ns | ns | ↑S | post-isch. cytotoxic |
| miR-19b | ↑S | ↑S | ns | ns | ns | post-isch. cytotoxic? |
| miR-19a | ↑S | ns | ns | ns | ns | post-isch. cytotoxic? |
| miR-181a | ↓S | ↓S | ns | ns | ↑S | post-isch. cytoprotective |
| miR-7b | ↓S | ↓S | ns | ns | ↑SS | post-isch. cytoprotective |

↑ up-regulation
↓ down-regulation
ns: non-significant regulation: below 1.5 fold (either positive or negative)
S: Significant regulation limit: 1.5 fold
SS: Very significant regulation
Bold: Preferred miRNA species.

INDUSTRIAL APPLICABILITY

The present inventors demonstrated herein that their inventive concept for analyzing miRNA levels in experimental (test) ischemia-reperfusion, preconditioning and postconditioning treatment of biological samples is appropriate for finding and preparing miRNA compounds useful in prophylaxis and treatment of ischemic associated conditions and specific compounds for cytoprotection in ischemia-reperfusion injury. It is shown that a number of miRNA compound from a limited set has such an effect and that using present inventor's method and the larger set of miRNAs further miRNA compounds can be prepared having the same effect well within the skills of a person skilled in the art.

REFERENCES

Bartel D P. MiRNAs: genomics, biogenesis, mechanism, and function Cell. 2004; 116: 281-297.

Bonauer A, Carmona G, Iwasaki M, Mione M, Koyanagi M, Fischer A, Burchfield J, Fox H, Doebele C, Ohtani K, Chavakis E, Potente M, Tjwa M, Urbich C, Zeiher A M, Dimmeler S. MiRNA-92a controls angiogenesis and functional recovery of ischemic tissues in mice Science. 2009; 324: 1710-1713.

Bostjancic E, Zidar N, Glavac D. MiRNA microarray expression profiling in human myocardial infarction Dis Markers. 2009; 27: 255-268.

Bostjancic E, Zidar N, Stajer D, Glavac D. MicroRNAs miR-1, miR-133a, miR-133b and miR-208 are dysregulated in human myocardial infarction. Cardiology. 2010 115(3) 163-9.

Buchan J R, Parker R. Molecular biology. The two faces of miRNA Science. 2007; 318: 1877-1878.

Busk P K, Cirera S. MiRNA profiling in early hypertrophic growth of the left ventricle in rats Biochem Biophys Res Commun. 2010; 396(4): 989-93.

Callis T E, Pandya K, Seok H Y, Tang R H, Tatsuguchi M, Huang Z P, Chen J F, Deng Z, Gunn B, Shumate J, Willis M S, Selzman C H, Wang D Z. MiRNA-208a is a regulator of cardiac hypertrophy and conduction in mice J Clin Invest. 2009; 119: 2772-2786.

Conroy R M, Pyorala K, Fitzgerald A P, Sans S, Menotti A, De Backer G, De Bacquer D, Ducimetiere P, Jousilahti P, Keil U, Njelstad I, Oganov R G, Thomsen T, Tunstall-Pedoe H, Tverdal A, Wedel H, Whincup P, Wilhelmsen L, Graham I M Estimation of ten-year risk of fatal cardio-vascular disease in Europe: the SCORE project. Eur Heart J. 2003 June; 24(11):987-1003.

Cheng Y, Zhu P, Yang J, Liu X, Dong S, Wang X, Chun B, Zhuang J and Zhang Ch., Ischaemic preconditioning-regulated miR-21 protects heart against ischaemia/reperfusion injury via anti-apoptosis through its target PDCD4, Cardiovascular Research (2010) 87, 431-439

Csonka C, Fekete V, Kupai K, Csont T, Puskas L, Ferdinandy P. Effect of postconditioning on the gene expression pattern of rat hearts: A DNA microarray study. J Mol Cell Cardiol. 2008; 44: 817-817.

Csonka C, Kupai K, Kocsis G F, Novak G, Fekete V, Bencsik P, Csont T, Ferdinandy P. Measurement of myocardial infarct size in preclinical studies J Pharmacol Toxicol Methods. 2010; 61: 163-170.

Csonka C, Szilvassy Z, Fulop F, Pali T, Blasig I E, Tosaki A, Schulz R, Ferdinandy P. Classic preconditioning decreases the harmful accumulation of nitric oxide during ischemia and reperfusion in rat hearts Circulation. 1999; 100: 2260-2266.

Dong S, Cheng Y, Yang J, Li J, Liu X, Wang X, Wang D, Krall T J, Delphin E S, Zhang C. MiRNA expression signature and the role of miRNA-21 in the early phase of acute myocardial infarction J Biol Chem. 2009; 284: 29514-29525.

Engelhardt S. and Jentzsch C. microRNA for diagnostic and therapeutic purposes in cardiovascular diseases WO2010/103015 (2010)

Farago N, Kocsis G F, Feher L Z, Csont T, Hackler L, Jr, Varga-Orvos Z, Csonka C, Kelemen J Z, Ferdinandy P, Puskas L G. Gene and protein expression changes in response to normoxic perfusion in mouse hearts J Pharmacol Toxicol Methods. 2008; 57: 145-154.

Fasanaro P, Greco S, Ivan M, Capogrossi M C, Martelli F. miRNA: emerging therapeutic targets in acute ischemic diseases Pharmacol Ther. 2010; 125: 92-104.

Feher L Z, Kalman J, Puskas L G, Gyulveszi G, Kitajka K, Penke B, Palotas M, Samarova E I, Molnar J, Zvara A, Matin K, Bodi N, Hugyecz M, Pakaski M, Bjelik A, Juhasz A, Bogats G, Janka Z, Palotas A. Impact of haloperidol and risperidone on gene expression profile in the rat cortex Neurochem Int. 2005; 47: 271-280.

Ferdinandy P, Schulz R, Baxter G F. Interaction of cardiovascular risk factors with myocardial ischemia-reperfusion injury, preconditioning, and postconditioning Pharmacol Rev. 2007; 59: 418-458.

Frost R J, van Rooij E. miRNAs as therapeutic targets in ischemic heart disease J Cardiovasc Transl Res. 2010; 3: 280-289.

Gene Therapy, (2011) 10 1038

Godwin J G, Ge X, Stephan K, Jurisch A, Tullius S G, Iacomini J Identification of a microRNA signature of renal ischemia reperfusion injury. Proc Natl Acad Sci USA. 2010 107(32) 14339-44.

Griffiths-Jones S, Grocock R J, van Dongen S, Bateman A, Enright A J. miRBase: miRNA sequences, targets and gene nomenclature. NAR 2006 34 (Database Issue): D140-D144

Hasseine L K, Hinault C, Lebrun P, Gautier N, Paul-Bellon R, Van Obberghen E. miR-139 impacts FoxO1 action by decreasing FoxO1 protein in mouse hepatocytes Biochem Biophys Res Commun. 2009; 390: 1278-1282.

He B, Xiao J, Ren A J, Zhang Y-F, Zhang H, Chen M, Xie B, Gao X-G, Wang Y-W, Role of miR-1 and miR-133a in myocardial ischemic postconditioning, Journal of Biomedical Science 2011, 18:22

Huang C, Yitzhaki S, Perry C N, Liu W, Giricz Z, Mentzer R M, Jr, Gottlieb R A. Autophagy induced by ischemic preconditioning is essential for cardioprotection J Cardiovasc Transl Res. 2010; 3: 365-373.

Kauppinen S, Vester B, Wenge J. Locked nucleic acid (LNA): High affinity targeting of RNA for diagnostics and therapeutics. Drug Discovery Today: Technologies (2005) 2(3) 287-290

Le M T, Teh C, Shyh-Chang N, Xie H, Zhou B, Korzh V, Lodish H F, Lim B MiRNA-125b is a novel negative regulator of p53 Genes Dev. 2009; 23: 862-876.

Lee Y S, Kim H K, Chung S, Kim K S, Dutta A. Depletion of human micro-RNA miR-125b reveals that it is critical for the proliferation of differentiated cells but not for the down-regulation of putative targets during differentiation J Biol Chem. 2005; 280: 16635-16641.

Lennox K A and Behlke M A. Chemical modification and design of anti-miRNA oligonucleotides.

Lewis B P, Burge C B, Bartel D P. Conserved seed pairing, often flanked by adenosines, indicates that thousands of human genes are miRNA targets Cell. 2005; 120: 15-20.

Lim L P, Lau N C, Garrett-Engele P, Grimson A, Schelter J M, Castle J, Bartel D P, Linsley P S, Johnson J M. Microarray analysis shows that some miRNAs downregulate large numbers of target mRNAs Nature. 2005; 433: 769-773.

Lu Y, Zhang Y, Wang N, Pan Z, Gao X, Zhang F, Zhang Y, Shan H, Luo X, Bai Y, Sun L, Song W, Xu C, Wang Z, Yang B. MiRNA-328 contributes to adverse electrical remodeling in atrial fibrillation Circulation. 2010; 122: 2378-2387.

Meder B, Keller A, Vogel B, Haas J, Sedaghat-Hamedani F, Kayvanpour E, Just S, Borries A, Rudloff J, Leidinger P, Meese E, Katus H A, Rottbauer W. MicroRNA signatures in total peripheral blood as novel biomarkers for acute myocardial infarction. Basic Res Cardiol. 2011 106(1) 13-23.

Lusardi T A. Fan C D, Faulkner C L, Pignataro G, Yang T, Lan J, Simon R P and Saugstad J A, Ischemic preconditioning regulates expression of microRNAs and a predicted target, MeCP2, in mouse cortex, Journal of Cerebral Blood Flow & Metabolism (2010) 30, 744-756

Obad Susanna, Santos Camila O dos, Petri Andreas, Heidenblad Markus, Broom Oliver, Ruse Cristian, Fu Cexiong, Lindow Morten, Stenvang Jan, Straarup Ellen Marie, Hansen Henrik Frydenlund, Koch Troels, Pappin Darryl, Hannon Gregory J and Kauppinen Sakari. Silencing of microRNA families by seed-targeting tiny LNAs. Nature Genetics 43 (2011) 371-378

Olson E. and Van Rooij, E. Dual targeting of mir-208 and mir-499 in the treatment of cardiac disorders WO 2010/091204 (2010)

Olson E. and Van Rooij, E. Identification of micro-rnas involved in post-myocardial infarction remodeling and heart failure WO2010/135570 (2010)

Olson E. and Van Rooij, E. Micro-RNAs of the MIR-15 family modulate cardiomyocyte survival and cardiac repair. WO2009/062169 (2009)

Olson E. and Van Rooij, E. Micro-RNAs of the miR-15 family modulate cardiomyocyte survival and cardiac repair US2010/0317713 (2010)

Olson E. Van Rooij, E., Frost R. Targeting of the mir-30 family and let-7 family as a treatment for heart disease WO2010/120969 (2010)

Olson Eric N.; Rooij Eva Van; Quiat D. Micro-ma regulation in ischemic and ischemic-reperfusion injury WO2011/084460 (2011)

Onody A, Zvara A, Hackler L, Jr, Vigh L, Ferdinandy P, Puskas L G. Effect of classic preconditioning on the gene expression pattern of rat hearts: a DNA microarray study FEBS Lett. 2003; 536: 35-40.

Ovize M, Baxter G F, Di Lisa F, Ferdinandy P, Garcia-Dorado D, Hausenloy D J, Heusch G, Vinten-Johansen J, Yellon D M, Schulz R. Postconditioning and protection from reperfusion injury: where do we stand?: Position Paper from the Working Group of Cellular Biology of the Heart of the European Society of Cardiology Cardiovasc Res. 2010;

Puskas L G, Juhasz F, Zarva A, Hackler L, Jr, Farid N R. Gene profiling identifies genes specific for well-differentiated epithelial thyroid tumors Cell Mol Biol. 2005; 51: 177-186.

Ren X P, Wu J, Wang X, Sartor M A, Qian J, Jones K, Nicolaou P, Pritchard T J, Fan G C. MiRNA-320 is involved in the regulation of cardiac ischemic-reperfusion injury by targeting heat-shock protein 20 Circulation. 2009; 119: 2357-2366.

Robertson B, Dalby A B., Karpilow J, Khvorova A, Leake D, Vermeulen A. Specificity and functionality of miRNA inhibitors. Silence 2010 1 10

Sen C K, Roy S. miRNA: licensed to kill the messenger. DNA Cell Biol. 2007 April; 26(4):193-4

Sengupta A, Molkentin J D, Yutzey K E. FoxO transcription factors promote autophagy in cardiomyocytes J Biol Chem. 2009; 284: 28319-28331.

Sepramaniam S, Armugam A, Lim K Y, Karolina D S, Swaminathan P, Tan J R, and Jeyaseelan K, MicroRNA 320a Functions as a Novel Endogenous Modulator of Aquaporins 1 and 4 as Well as a Potential Therapeutic Target in Cerebral Ischemia The Journal Of Biological Chemistry (2010) 285(38) 29223-29230, Shayne C. Gad, Handbook of pharmaceutical biotechnology, John Wiley and Sons, 2007 (1659 pages).

Small E M, Frost R J A, Olson E N. MiRNAs add a new dimension to cardiovascular disease Circulation 2010 121 1022-1032

Sun H Y, Wang N P, Halkos M, Kerendi F, Kin H, Guyton R A, Vinten-Johansen J, Zhao Z Q. Postconditioning attenuates cardiomyocyte apoptosis via inhibition of JNK and p38 mitogen-activated protein kinase signaling pathways Apoptosis. 2006; 11: 1583-1593.

Talukder M A, Zweier J L, Periasamy M. Targeting calcium transport in ischaemic heart disease Cardiovasc Res. 2009; 84: 345-352.

Thum T. and Fiedler, J. Use of microRNA-24 and/or its targets for the treatment and prevention of ischemic and induction of angiogenesis E P2275545A1 (2011)

Thum T., Bauersachs J. Microrna (mirna) for the diagnosis and treatment of heart diseases U S2010/0010073 (2010)

van Rooij E, Olson E N. MiRNAs: powerful new regulators of heart disease and provocative therapeutic targets J Clin Invest. 2007; 117: 2369-2376.

van Rooij E, Quiat D, Johnson B A, Sutherland L B, Qi X, Richardson J A, Kelm R J, Jr, Olson E N. A family of miRNAs encoded by myosin genes governs myosin expression and muscle performance Dev Cell. 2009; 17: 662-673.

van Rooij E, Sutherland L B, Qi X, Richardson J A, Hill J, Olson E N. Control of stress-dependent cardiac growth and gene expression by a miRNA Science. 2007; 316: 575-579.

Vermeulen A, Robertson B, Dalby A B. Double-stranded regions are essential design components of potent inhibitors RNA 2007 13: 723-730

Wang H C, Zhang H F, Guo W Y, Su H, Zhang K R, Li Q X, Yan W, Ma X L, Lopez B L, Christopher T A, Gao F. Hypoxic postconditioning enhances the survival and inhibits apoptosis of cardiomyocytes following reoxygenation: role of peroxynitrite formation Apoptosis. 2006; 11: 1453-1460.

Wang Ning; Wang Zhi-Guo; Zhang Ying; Yang Bao-Feng; Pan Zhen-Wei; Lv Yan-Jie; Chu Wen-Feng; Shan Hong-li MicroRNA-328 and use of anti-sense nucleotide thereof in diagnosing, preventing and treating heart disease C N101643791A (2010)

Wang X, Zhang X, Ren X P, Chen J, Liu H, Yang J, Medvedovic M, Hu Z, Fan G C. MiRNA-494 targeting both proapoptotic and antiapoptotic proteins protects against ischemia/reperfusion-induced cardiac injury Circulation. 2010; 122: 1308-1318.

Waspe L E, Ordahl C P, Simpson P C. The cardiac beta-myosin heavy chain isogene is induced selectively in alpha 1-adrenergic receptor-stimulated hypertrophy of cultured rat heart myocytes J Clin Invest. 1990; 85: 1206-1214.

Yan H L, Xue G, Mei Q, Wang Y Z, Ding F X, Liu M F, Lu M H, Tang Y, Yu H Y, Sun S H. Repression of the miR-17-92 cluster by p53 has an important function in hypoxia-induced apoptosis EMBO J. 2009; 28: 2719-2732.

Ye Y, Perez-Polo J R, Qian J, Birnbaum Y. The role of microRNA in modulating myocardial ischemia-reperfusion injury. Physiol Genomics. 2011 43(10): 534-42.

Yin K J, Deng Z, Huang H, Hamblin M, Xie C, Zhang J, Chen Y E. miR-497 regulates neuronal death in mouse brain after transient focal cerebral ischemic. Neurobiol Dis. 2010 38(1) 17-26.

Wijns W, Kolh P, Danchin N, Mario C, Falk V, Folliguet T, Garg S, Huber K, James S, Knuuti J, Lopez-Sendon J, Marco J, Menicanti L, Ostojic M, Piepoli M F, Pirlet C, Pomar J L, Reifart N, Ribichini F L, Schalij M J, Sergeant P, Serruys P W, Silber S, Uva M S, Taggart D, Guidelines on myocardial revascularization European Heart Journal 2010 31, 2501-2555.

Xu, Cheng-fu, Yu Chao-hui and Li, You-ming, Regulation of Hepatic MicroRNA Expression in Response to Ischemic Preconditioning following Ischemia/Reperfusion Injury in Mice, A Journal of Integrative Biology 2009 13(6) 513-520

The invention claimed is:

1. A method of treating a patient to protect cells in the heart of said patient against consequences of acute ischemic and reperfusion injury comprising administering to the heart of said patient at least one miRNA compound selected from the group consisting of a miRNA agonist of miR-139-5p, a miRNA agonist of miR-125b*, a miRNA agonist of let-7b, and a miRNA antagonist of miR-487b, wherein each miRNA agonist is an oligonucleotide of 17-27 nucleotides in length which comprises a core nucleotide sequence of at least 17 nucleotides that is identical over its length to miR-139-5p, miR-125*, or let-7b, or that differs from miR-139-5p, miR-125b*, or let-7b at no more than 6 nucleotide positions, and wherein the miRNA antagonist is an oligonucleotide of 17 to 27 nucleotides in length which comprises a core nucleotide sequence of at least 17 nucleotides that is perfectly complementary over its length to miR-487b, or that differs from perfect complementarity at no more than 6 nucleotide positions.

2. The method according to claim 1 wherein said miRNA compound is a miRNA agonist of miR-125b*.

3. The method according to claim 1 wherein said miRNA compound is a miRNA agonist of miR-139-5p.

4. The method according to claim 1 wherein said miRNA compound is a miRNA agonist of let-7b.

5. The method according to claim 1 wherein said miRNA compound is a miRNA antagonist of miR-487b.

6. The method according to claim 1 said composition comprising a combination of more than one of said miRNA compounds.

7. The method of claim 1, wherein each miRNA agonist is an oligonucleotide of 17-27 nucleotides in length which comprises a nucleotide sequence that is identical to the seed sequence of miR-139-5p, miR-125b*, or let-7b, and wherein the miRNA antagonist is an oligonucleotide of 17 to 27 nucleotides in length that comprises a sequence that is perfectly complementary to the seed sequence of miR-487b.

8. The method of claim 1 wherein each miRNA agonist comprises a core nucleotide sequence of at least 17 nucleotides that differs from miR-139-5p, miR-125b*, or let-7b at no more than 4 nucleotide positions, and wherein the miRNA antagonist comprises a core nucleotide sequence of at least 17 nucleotides that differs from perfect complementarity over its length to miR-487b at no more than 4 nucleotide positions.

9. The method according to claim 1 wherein said miRNA compound is administered to the patient within 5, 4, 3, 2 or 1.5 hour(s) after an ischemic attack or simultaneously with reperfusion and/or less than 5, 4, 3, 2 or 1 hour(s) before surgery or intervention associated with a risk of ischemia.

10. The method of treatment according to claim 9 wherein said miRNA compound is administered to the patient within 3 hours after the ischemic attack or simultaneously with reperfusion and/or less than 3 hours before surgery or intervention associated with a risk of ischemia.

* * * * *